(12) United States Patent
Shibue et al.

(10) Patent No.: US 6,615,659 B2
(45) Date of Patent: Sep. 9, 2003

(54) HUMIDITY SENSOR AND METHOD FOR MANUFACTURING THE SAME

(75) Inventors: Akira Shibue, Tokyo (JP); Kenryo Namba, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 10/095,435

(22) Filed: Mar. 13, 2002

(65) Prior Publication Data

US 2003/0056571 A1 Mar. 27, 2003

(30) Foreign Application Priority Data

| Mar. 13, 2001 | (JP) | ................................. 2001-070353 |
| Aug. 7, 2001 | (JP) | ................................. 2001-239676 |
| Mar. 7, 2002 | (JP) | ................................. 2002-062011 |
| Mar. 7, 2002 | (JP) | ................................. 2002-062012 |
| Mar. 7, 2002 | (JP) | ................................. 2002-062013 |

(51) Int. Cl.$^7$ ............................. G01N 9/00; G01N 7/00; H01C 7/00
(52) U.S. Cl. ................... 73/335.02; 73/29.01; 338/35; 324/664
(58) Field of Search .................. 422/82.02; 338/35; 73/29.01, 29.02, 29.05, 335.02, 335.03, 335.04, 335.05; 324/664, 689, 694

(56) References Cited

U.S. PATENT DOCUMENTS

| 3,689,468 | A | * | 9/1972 | Cenci et al. ................. 526/312 |
| 4,322,331 | A | * | 3/1982 | Shay ........................... 524/815 |
| 4,473,813 | A | * | 9/1984 | Kinjo et al. ............. 73/335.05 |
| 5,546,802 | A | | 8/1996 | Yoshimura et al. |
| 6,063,486 | A | * | 5/2000 | Kobayashi ................... 338/35 |
| 6,241,873 | B1 | * | 6/2001 | Namba et al. ............... 292/340 |

FOREIGN PATENT DOCUMENTS

| EP | 0 567 152 | 10/1993 | .................. 427/96 |
| EP | 0 676 636 | 10/1995 | .................. 427/96 |

(List continued on next page.)

OTHER PUBLICATIONS

Shiro Nakagawa, et al. "A Polymer Humidity Sensor Stabilized Against Oxidative Gases and its Signal Processing Circuits," Meeting Abstracts Washington, The 199th Meeting of The Electrochemical Society, vol. 2001–1, 2001, 2 pages, No Month.

*Primary Examiner*—Edward Lefkowitz
*Assistant Examiner*—Michael Cygan
(74) *Attorney, Agent, or Firm*—Oblon, Spivak, McClelland, Maier & Neustadt, P.C.

(57) ABSTRACT

In a humidity sensor device comprising a pair of opposed electrodes disposed on an insulating substrate to define a gap therebetween and a humidity sensitive thin film lying on the gap, the humidity sensitive thin film is a thin film comprising a polymer or copolymer obtained from a monomer of formula (1), and formation of the humidity sensitive thin film is optionally combined with treatment of the insulating substrate by physical means. A humidity sensor device for detecting and determining moisture in the surrounding atmosphere which has improved water resistance, solvent resistance, and gas resistance, and exhibits stable output performance in a wide humidity region without hysteresis is provided as well as a method for preparing the same.

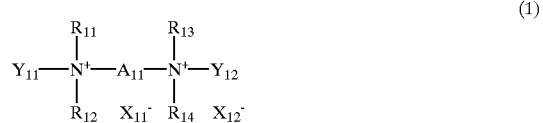

(1)

In formula (1), $A_{11}$ is a divalent group, $R_{11}$ to $R_{14}$ are alkyl, $Y_{11}$ and $Y_{12}$ are monovalent groups terminated with an ethylenically unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and $X_{11}^-$ and $X_{12}^-$ are anions.

38 Claims, 19 Drawing Sheets

FOREIGN PATENT DOCUMENTS

| | | | | |
|---|---|---|---|---|
| JP | 60-113140 | 6/1985 | ................ | 427/96 |
| JP | 61-054176 | 11/1986 | | |
| JP | 62-7976 | 2/1987 | | |
| JP | 63-86704 A * | 4/1988 | | |
| JP | 2-24465 | 5/1990 | | |
| JP | 2-140653 A * | 5/1990 | ................ | 72/29.05 |
| JP | 6-43129 | 2/1994 | ................ | 427/96 |
| JP | 7-318525 | 12/1995 | | |
| JP | 2808255 | 7/1998 | | |
| WO | WO 99/27357 | 6/1999 | ................ | 427/96 |

\* cited by examiner

HUMIDITY SENSOR AND METHOD FOR MANUFACTURING THE SAME

BACKGROUND OF THE INVENTION

1. Technical Field

This invention relates to a humidity sensor device for detecting and determining moisture in the surrounding atmosphere and a method for preparing the same.

2. Background Art

Known humidity sensors designed to detect humidity through changes of electrical properties, typically electric resistance include those using electrolytes such as lithium chloride, metal oxides, and organic polymers as the humidity sensitive material.

However, the humidity sensors using electrolytes such as lithium chloride can measure only a narrow range of humidity and are less resistant to water in that their performance can be altered by dew condensation and wetting. The humidity sensors using metal oxides are resistant to water, but low sensitive. Because of the lack of long-term stability when used alone, they undesirably require a heat cleaning circuit which would add to the operating cost and make the sensor structure complex.

Among the humidity sensitive materials, organic polymers, especially polymeric electrolytes having quaternary ammonium salt have been widely used in commercial and industrial applications and so appreciated.

For example, Japanese Patent Publication (JP-B) No. 61-54176 discloses a humidity sensitive material comprising aggregates of latex particles formed of a copolymer between a hydrophobic monomer and an ionic or non-ionic hydrophilic monomer and having a hydrophilic surface layer. There are exemplified some cationic compounds having primary to quaternary ammonium salts.

JP-B 62-7976 discloses a humidity sensitive material in the form of a polymer which is obtained by polymerizing a compound containing 2-hydroxy-3-methacryloxypropyl-trimethylammonium chloride to a degree of polymerization of 1,000 to 10,000.

JP-B 2-24465 discloses the use as a humidity sensitive polymeric thin film of a thin film of an ionene polymer having the structural formula:

wherein $R_1$ to $R_4$ are alkyl, $X^-$ is a halide ion, A and B each are $-(CH_2)_m-$ wherein $m \geq 2$, or a thin film of a mixture of the polymer with another polymer such as polyvinyl pyrrolidone for the purposes of improving substrate adhesion and water resistance.

Humidity sensors using the polymeric electrolytes exemplified above as the humidity sensitive material, however, are still low in water resistance in that the polymeric electrolytes can be partially leached in a high humidity region, especially in a dew condensing atmosphere. They also suffer from a hysteresis phenomenon that they produce different outputs at the same humidity depending on whether the humidity is increasing or decreasing. In a low humidity region having a relative humidity (RH) of less than 10%, they have so high resistance values that practical humidity measurement is impossible.

JP-A 7-318526 discloses that water resistance is improved by introducing an unsaturated bond into the ionene polymer at either end and crosslinking with ultraviolet radiation. In this case, a very thin film provides satisfactory properties and water resistance. However, the small thickness means so small an absolute amount of the polymer that the film is vulnerable to a gas which is dissolved in water to form ions (e.g., $Cl_2$, NOx, SOx). The problem is serious particularly in a commercial application.

The conductivity of a film having a thickness above a certain level is not substantially altered even when gas-origin ions are created in the surface layer. The polymer layer obtained by the above crosslinking method, however, undergoes substantial swell upon absorption of water, giving rise to serious problems of crack generation and separation from the substrate. Under such circumstances, the film must be used at a thickness of no more than 1 μm.

SUMMARY OF THE INVENTION

A primary object of the present invention is to provide a humidity sensor device having a humidity sensitive thin film which is resistant to water, maintains effective, stable performance over a long time even in a dew condensing atmosphere, is resistant to solvents and less vulnerable to gases such as nitrogen oxides, sulfur oxide and chlorine, and produces accurate outputs in a stable manner over a wide humidity region, especially in a low humidity region; and a method for preparing the same. Another object is to provide a simple method for preparing such a humidity sensor device having improved properties as mentioned above.

These and other objects are achieved by the present invention which is defined below as (1) to (38).

(1) A humidity sensor device comprising an insulating substrate, a pair of opposed electrodes disposed on the substrate to define a gap therebetween, and a humidity sensitive thin film lying on the gap, said humidity sensitive thin film comprising a copolymer of at least one monomer of the following formula (1) with at least one monomer of the following formula (2):

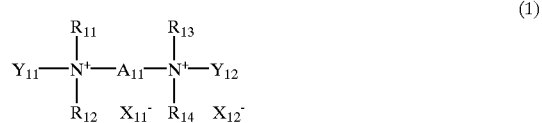

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an ethylenically unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion,

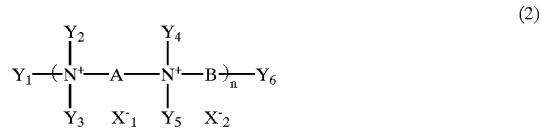

wherein each of A and B is a divalent group, each of $Y_1$, $Y_2$, $Y_3$, $Y_4$, $Y_5$ and $Y_6$ which may be the same or different is a monovalent group, at least one of Y's is a group terminated with an ethylenically unsaturated reactive group, any two or more of $Y_1$, $Y_2$, $Y_3$, $Y_4$, $Y_5$, A and portions thereof adjoining the nitrogen (N) atom or any two or more of $Y_4$, $Y_5$, $Y_6$, B and portions thereof adjoining the nitrogen (N) atom may bond together to form a ring with the nitrogen (N) atom, each of $X_1^-$ and $X_2^-$ which may be the same or different is an anion, and n is a number of 2 to 5,000.

(2) The humidity sensor device of above (1) wherein the anions represented by $X_{11}^-$ and $X_{12}^-$ in formula (2) and the anions represented by $X_{11}^-$ and $X_{12}^-$ in formula (1) are halide ions.

(3) The humidity sensor device of above (2) wherein chloride ions or bromide ions are contained as the halide ions.

(4) The humidity sensor device of above (1) wherein the divalent groups represented by A and B in formula (2) and the divalent group represented by $A_{11}$ in formula (1) each are an alkylene, alkenylene or arylene group or a mixture thereof.

(5) The humidity sensor device of above (1) wherein the monovalent groups represented by $Y_{11}$ and $Y_{12}$ in formula (1) each are an alkylene acrylate or methacrylate group or alkylene acrylate or methacrylate amide group.

(6) The humidity sensor device of above (1) wherein the monomer of formula (1) is a difunctional monomer obtained by reacting a dialkylaminoethyl acrylate or methacrylate or a dialkylaminoethyl acrylate or methacrylate amide with a dihalogen compound.

(7) The humidity sensor device of above (1) wherein the monomer of formula (1) is obtained by reacting an acrylic unsaturated compound having a dialkylamino group with a dihalogen compound of the divalent group represented by $A_{11}$ in formula (1).

(8) The humidity sensor device of above (1) wherein the copolymer further includes an acrylic monomer having an alkoxysilyl group.

(9) The humidity sensor device of above (1) wherein the insulating substrate is an insulating substrate from which contaminants and/or oxides on its uppermost surface layer have been removed by physical means.

(10) A method for preparing a humidity sensor device comprising an insulating substrate, a pair of opposed electrodes disposed on the substrate to define a gap therebetween, and a humidity sensitive thin film lying on the gap, said method comprising the steps of coating a coating solution containing a monomer of the following formula (1) and a monomer of the following formula (2) onto the insulating substrate and causing the monomers to copolymerize to form the humidity sensitive thin film,

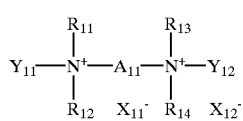
(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an ethylenically unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion,

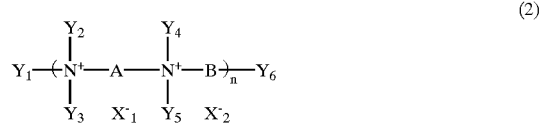
(2)

wherein each of A and B is a divalent group, each of $Y_1$, $Y_2$, $Y_3$, $Y_4$, $Y_5$ and $Y_6$ which may be the same or different is a monovalent group, at least one of Y's is a group terminated with an ethylenically unsaturated reactive group, any two or more of $Y_1$, $Y_2$, $Y_3$, $Y_4$, $Y_5$, A and portions thereof adjoining the nitrogen (N) atom or any two or more of $Y_4$, $Y_5$, $Y_6$, B and portions thereof adjoining the nitrogen (N) atom may bond together to form a ring with the nitrogen (N) atom, each of $X_{11}^-$ and $X_{12}^-$ which may be the same or different is an anion, and n is a number of 2 to 5,000.

(11) The method for preparing a humidity sensor device of above (10) wherein the humidity sensitive thin film is formed by previously treating the insulating substrate with an acrylic monomer having an alkoxysilyl group for joining acrylic functional groups to the insulating substrate, then coating said coating solution, or by previously incorporating an acrylic monomer having an alkoxysilyl group into said coating solution.

(12) The method for preparing a humidity sensor device of above (10), further comprising the step of removing contaminants and/or oxides on the uppermost surface layer of the insulating substrate by physical means, prior to the step of coating said coating solution.

(13) The method for preparing a humidity sensor device of above (12) wherein said physical means is plasma surface treatment.

(14) The method for preparing a humidity sensor device of above (10) wherein the copolymerization is carried out by irradiation of ultraviolet radiation.

(15) A humidity sensor device comprising an insulating substrate, a pair of opposed electrodes disposed on the substrate to define a gap therebetween, and a humidity sensitive thin film lying on the gap,
said humidity sensitive thin film comprising a copolymer of a monomer of the following formula (1) with an acrylic monomer having an alkoxysilyl group,

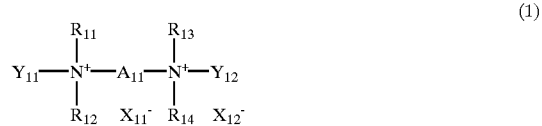
(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion.

(16) The humidity sensor device of above (15) wherein the humidity sensitive thin film is secured to the substrate through reaction of alkoxysilyl groups in the copolymer in the humidity sensitive thin film with functional groups on the surface of the insulating substrate and/or the electrodes.

(17) The humidity sensor device of above (15) wherein at least 30 mol % of the anions represented by $X_{11}^-$ and $X_{12}^-$ in the copolymer are chloride ions.

(18) The humidity sensor device of above (15) wherein the divalent group represented by $A_{11}$ in formula (1) is an alkylene, alkenylene or arylene group or a mixture thereof.

(19) The humidity sensor device of above (15) wherein the monovalent groups represented by $Y_{11}$ and $Y_{12}$ in formula (1) each are an alkylene acrylate or methacrylate group or alkylene acrylate or methacrylate amide group.

(20) The humidity sensor device of above (15) wherein the monomer of formula (1) is a difunctional monomer obtained by reacting a dialkylaminoethyl acrylate or methacrylate or a dialkylaminoethyl acrylate or methacrylate amide with a dihalogen compound.

(21) The humidity sensor device of above (15) wherein the monomer of formula (1) is obtained by reacting an acrylic unsaturated compound having a dialkylamino group with a dihalogen compound of the divalent group represented by $A_{11}$ in formula (1).

(22) A method for preparing a humidity sensor device comprising an insulating substrate, a pair of opposed electrodes disposed on the substrate to define a gap therebetween, and a humidity sensitive thin film lying on the gap, said method comprising the steps of previously treating the insulating substrate with an acrylic monomer having an alkoxysilyl group for joining acrylic functional groups to the insulating substrate, coating a monomer of the following formula (1), then causing the monomer to polymerize to form the humidity sensitive thin film,

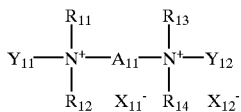

(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion.

(23) The method for preparing a humidity sensor device of above (22) wherein the polymerization is carried out by irradiation of ultraviolet radiation.

(24) A method for preparing a humidity sensor device comprising an insulating substrate, a pair of opposed electrodes disposed on the substrate to define a gap therebetween, and a humidity sensitive thin film lying on the gap, said method comprising the steps of coating a monomer of the following formula (1) and an acrylic monomer having an alkoxysilyl group onto the insulating substrate, causing the monomers to copolymerize into a copolymer, and causing the alkoxysilyl groups to react with functional groups on the surface of the insulating substrate in the presence of water vapor to secure the copolymer to the insulating substrate, for thereby forming the humidity sensitive thin film,

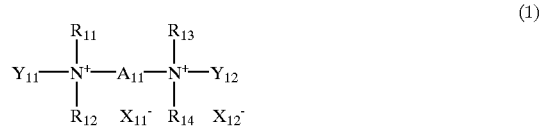

(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, each of $X_{11}^-$ and $X_{12}^-$ which may be the same or different is an anion.

(25) The method for preparing a humidity sensor device of above (24) wherein the polymerization is carried out by irradiation of ultraviolet radiation.

(26) A humidity sensor device comprising an insulating substrate, a pair of opposed electrodes disposed on the substrate to define a gap therebetween, and a humidity sensitive thin film lying on the gap, wherein said insulating substrate is an insulating substrate from which contaminants and/or oxides on its uppermost surface layer have been removed by physical means, and said humidity sensitive thin film comprises a polymer resulting from a monomer of the following formula (1):

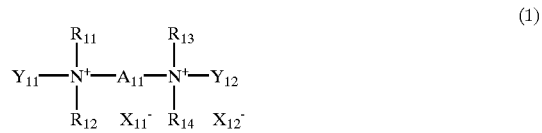

(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion.

(27) The humidity sensor device of above (26) wherein at least 30 mol % of the anions represented by $X_{11}^-$ and $X_{12}^-$ in the copolymer are chloride ions.

(28) The humidity sensor device of above (26) wherein the divalent group represented by $A_{11}$ in formula (1) is an alkylene, alkenylene or arylene group or a mixture thereof.

(29) The humidity sensor device of above (26) wherein the monovalent groups represented by $Y_{11}$ and $Y_{12}$ in formula (1) each are an alkylene acrylate or methacrylate group or alkylene acrylate or methacrylate amide group.

(30) The humidity sensor device of above (26) wherein the monomer of formula (1) is a difunctional monomer obtained by reacting a dialkylaminoethyl acrylate or methacrylate or a dialkylaminoethyl acrylate or methacrylate amide with a dihalogen compound.

(31) The humidity sensor device of above (26) wherein the monomer of formula (1) is obtained by reacting an acrylic unsaturated compound having a dialkylamino group with a dihalogen compound of the divalent group represented by $A_{11}$ in formula (1).

(32) A method for preparing a humidity sensor device comprising an insulating substrate, a pair of opposed electrodes disposed on the substrate to define a gap therebetween, and a humidity sensitive thin film lying on the gap, said method comprising the steps of removing contaminants and/or oxides on the uppermost surface layer of the insulating substrate by physical means, then coating a monomer of the following formula (1) onto the insulating substrate, and causing the monomer to copolymerize on the insulating substrate for thereby forming the humidity sensitive thin film:

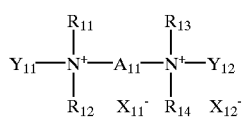

(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion.

(33) The method for preparing a humidity sensor device of above (32) wherein said physical means is plasma surface treatment.

(34) The method for preparing a humidity sensor device of above (32) wherein the polymerization is carried out by irradiation of ultraviolet radiation.

(35) A method for preparing a humidity sensor device comprising an insulating substrate, a pair of opposed electrodes disposed on the substrate to define a gap therebetween, and a humidity sensitive thin film lying on the gap, said method comprising the steps of removing contaminants and/or oxides on the uppermost surface layer of the insulating substrate by physical means, then coating a monomer having an ethylenically unsaturated reactive group onto the insulating substrate, and causing the monomer to copolymerize on the insulating substrate for thereby forming the humidity sensitive thin film.

(36) The method for preparing a humidity sensor device of above (35) wherein said physical means is plasma surface treatment.

(37) The method for preparing a humidity sensor device of above (35) wherein the monomer having an ethylenically unsaturated reactive group contains a quaternary ammonium salt.

(38) A humidity sensor device comprising an insulating substrate, a pair of opposed electrodes disposed on the substrate to define a gap therebetween, and a humidity sensitive thin film lying on the gap, wherein said the insulating substrate is an insulating substrate from which contaminants and/or oxides on its uppermost surface layer have been removed by physical means, and said humidity sensitive thin film comprises a polymer resulting from a monomer having an ethylenically unsaturated reactive group.

OPERATION

According to the invention, a humidity sensitive thin film of an electrically conductive polymer is formed so as to cover a pair of opposed electrodes on an insulating substrate.

In the first embodiment of the present invention, the humidity sensitive thin film is obtained by furnishing at least one of crosslinking monomers of formula (1) (abbreviated as monomer of formula (1), hereinafter) and at least one of crosslinking monomers of formula (2) (abbreviated as monomer of formula (2), hereinafter), that is, at least two monomers together, and causing the monomers to polymerize together by suitable means such as ultraviolet irradiation or heating. As seen from the monomers of formulae (1) and (2), the copolymer obtained therefrom is characterized by the possession of an ionene polymer structure having a quaternary ammonium salt (inclusive of cyclized one).

Since the monomers are preferably difunctional or have two acrylic unsaturated reactive groups, the crosslinking copolymer undergoes three-dimensional reaction to form a crosslinked structure which becomes insoluble in water.

In the humidity sensitive thin film using the crosslinking copolymer of ionene polymer structure, the quaternary ammonium salt moiety contained in the copolymer molecule contributes to electric conductivity and the counter ion thereto is dissociated with moisture in the surrounding atmosphere to develop ionic conduction. Humidity is detected by utilizing the phenomenon that the degree of dissociation varies as the moisture content in the atmosphere increases or decreases. In the first embodiment of the invention wherein the ionene polymer structure is included in the crosslinking copolymer, the copolymer is close to the backbone type with a less degree of freedom unlike the so-called pendant type. Its humidity response does not develop hysteresis.

The humidity sensitive film which is formed by copolymerization of monomers on the electrodes does not always have a uniform distribution of crosslinking sites within it because polymerization takes place in a dry state. This is because, when copolymerization is effected by exposure to UV radiation, for example, the difference of photon density between the surface and the interior of the film becomes large in the case of solids, with the tendency that an outer side has a higher crosslinking density. The humidity sensitive film is more likely to crack upon swelling due to water absorption as it becomes thicker. It is then necessary to make the crosslinking density uniform or to increase the number of crosslinking sites.

Therefore, the first embodiment of the invention is characterized in that the monomer of formula (1) which can assume an ionene polymer structure having improved properties when polymerized to form a humidity sensitive material is combined as the crosslinking agent with the monomer of formula (2), for thereby increasing the number of crosslinking sites while maintaining a low impedance. Since the monomer of formula (1) and the monomer of formula (2), which differ in molecular weight, are analogous monomers in that they can possess an ionene polymer structure within them, they enable to increase the number of crosslinking sites without reducing the ion density.

From the standpoint of device design, by changing the molecular weight and mixing ratio of the monomer of formula (2), the factor of greater interest can be selected among basic factors of the humidity sensor including water resistance, gas resistance and hysteresis, which enables free design. An increase of ion density improves gas resistance, and an increase of crosslinking density improves water resistance. As the molecular weight increases, the monomer of formula (2) becomes more flexible, which restrains cracking after swelling. It is noted that to ensure water resistance in this case, the content of the monomer of formula (1) must be increased to enhance the degree of crosslinking. On the other hand, extreme crosslinking increases the possibility of hysteresis, which necessitates appropriate adjustment.

Referring to formulae (1) and (2), the structural factors that dictate the conductivity of the crosslinking copolymer include the number of carbon atoms in the backbone of A and B in formula (2) and $A_{11}$ in formula (1) (i.e., the length of divalent linking group), the type of anions $X_1^-$ and $X_2^-$ in formula (2), and $X_{11}^-$ and $X_{12}^-$ in formula (1). Therefore, a sensor device having desired properties can also be designed by combining the monomers in which these parameters are suitable selected.

In contrast, with respect to crosslinking agents which are commonly added in order to increase the number of crosslinking sites, such as divinyl benzene, it is confirmed that the strength of the film and the number of crosslinking sites are increased by adding them to the monomer of formula (2). However, such a customary crosslinking agent results in a humidity sensitive film which has an increased impedance because its swelling is suppressed due to the increased number of crosslinking sites by the addition of the crosslinking agent and because the crosslinking agent itself lacks electric conductivity. It is not suitable as the humidity sensitive film for humidity sensors.

JP-B 2-24465 cited above discloses a polymer containing a quaternary ammonium salt in its backbone, which is similar to the polymer according to the first embodiment of the invention. Unlike the first embodiment of the invention, the formation of a crosslinking structure within the polymer is referred to nowhere. In this respect, the first embodiment of the present invention is clearly different in construction and features from the patent publication. Although the combined use of another polymer such as polyvinyl pyrrolidone for the purpose of improving water resistance is recommended in the patent publication, the water resistance is apparently inferior.

Likewise, in JP-A 4-309855 and JP-A 7-128271, a methacryloxypropyl trimethyl ammonium salt having a hydroxyl group and trimethylolpropane trimethacrylate are applied to form a coating, after which the coating is polymerized and insolubilized for allegedly improving water resistance. What is disclosed is a method of mixing two or more polymers, followed by polymerization. Since the ammonium group on the humidity sensitive material is the so-called pendant type, the humidity response develops substantial hysteresis.

In the second embodiment of the present invention, the humidity sensitive thin film contains a crosslinking copolymer of a monomer of formula (1) with an acrylic monomer having an alkoxysilyl group. Then the humidity sensitive thin film is joined to the insulating substrate through reaction with the silane coupling agent within the molecule. That is, the humidity sensitive thin film is obtained by coating an aqueous solution or organic solvent solution of the monomer and the silane coupling agent having an acrylic unsaturated bond, drying, and subjecting the monomer and the silane coupling agent to copolymerization and crosslinking by irradiation of UV radiation and/or heating. The copolymer is characterized by having an ionene polymer structure having a quaternary ammonium salt (including cyclized one) as seen from the monomer of formula (1) and the silane coupling agent within the molecule.

In the humidity sensitive thin film using the crosslinking copolymer of ionene polymer structure, the quaternary ammonium salt moiety contained in the copolymer molecule contributes to electric conductivity and the counter ion thereto is dissociated with moisture in the surrounding atmosphere to develop ionic conduction. Humidity is detected by utilizing the phenomenon that the degree of dissociation varies as the moisture content in the atmosphere increases or decreases. In the second embodiment of the invention wherein the ionene polymer structure is included in the crosslinking copolymer, the copolymer is close to the backbone type with a less degree of freedom unlike the so-called pendant type. Its humidity response does not develop hysteresis.

In the invention, the ion density and crosslinking degree of the humidity sensitive film can be controlled by adjusting the length of divalent linking group $A_{11}$. This leads to the design that permits the factor of greater interest to be selected among factors including water resistance, gas resistance and hysteresis, which enables free design. An increase of ion density improves gas resistance, and an increase of crosslinking density improves water resistance. On the other hand, extreme crosslinking increases the possibility of hysteresis.

Since the monomers are preferably difunctional or have two acrylic unsaturated reactive groups, the crosslinking copolymer undergoes three-dimensional reaction to form a crosslinked structure which becomes insoluble in water. Since the silane coupling agent structure is included within the molecule, the copolymer can be firmly joined to the substrate through covalent bonds by reacting with functional groups such as hydroxyl groups on the substrate surface and/or electrode surface. These bonds ensure that the humidity sensitive thin film remains water resistant without becoming loose or peeling even when it is thick. The humidity sensor has improved water resistance and gas resistance as well as improved solvent resistance.

In the embodiment wherein the counter ion to the quaternary ammonium salt group in the copolymer is a chloride ion, a low humidity region of RH 10% or lower can be measured, substantially spreading the measurable humidity region. The humidity sensor of the invention can measure humidity over the entire range from RH 0% to RH 100%, which was unmeasurable with conventional sensors.

JP-B 2-24465 cited above discloses a polymer containing a quaternary ammonium salt in its backbone, which is similar to the polymer according to the second embodiment of the invention. Unlike the present invention, the structure having the silane coupling agent incorporated within the polymer and the crosslinking structure are referred to nowhere. Therefore, the second embodiment of the present invention is clearly different in construction and features from the patent publication. Although the combined use of another polymer such as polyvinyl pyrrolidone for the purpose of improving water resistance is recommended in the patent publication, the water resistance is apparently inferior.

Also, JP-A 4-258750 intends to improve water resistance by using an acrylic polymer having a cationic radical and a hydroxyl group and a polyfunctional isocyanate compound to form a three-dimensionally crosslinked polymer. With this method, it is expected that some of isocyanate is joined to the substrate surface by reacting with hydroxyl groups on the substrate surface, but its effect is little.

Likewise, in JP-A 4-309855 and JP-A 7-128271, a methacryloxypropyl trimethyl ammonium salt having a hydroxyl group and trimethylolpropane trimethacrylate are applied to form a coating, after which the coating is polymerized and insolubilized for allegedly improving water resistance. However, this fails to achieve a substantial improvement in the adhesion to the substrate.

Furthermore, JP-A 7-318525 discloses a bonding method involving treating a substrate with silicon tetrachloride, and reacting with poly(2-hydroxy-3-methacryloxypropyl) trimethyl ammonium salt for thereby reacting the substrate surface with hydroxyl groups in the polymer. This method establishes the adhesion of the humidity sensitive film to the substrate, but encounters difficulty in reproducing substrate treating conditions because of the high reactivity and storage instability of silicon tetrachloride. Also, since the ammonium group of the humidity sensitive material is of the so-called pendant type, it is unavoidable that humidity response develops hysteresis.

In the third embodiment of the present invention wherein contaminants and/or oxides on the uppermost surface layer of the insulating substrate are removed by physical means before a humidity sensitive thin film is formed, the humidity sensitive thin film is comprised of a polymer obtained from a monomer of formula (1), obviating the use of a monomer of formula (2) and an acrylic monomer having an alkoxysilyl group.

The insulating substrate on which the humidity sensitive film is to be formed is, most often, an alumina substrate whose uppermost surface layer is covered with contaminants, adsorbed gases, organic matter and oxides of the substrate itself, which preclude the humidity sensitive film from adhering thereto. The removal of contaminants improves the adhesion of the humidity sensitive thin film to the insulating substrate.

The reason why treatment is done by physical means is that treatment by chemical means, which can remove contaminants and organic matter, is not preferable because of difficulty to remove the oxide layer and the problem of used solution at the end of chemical treatment. In contrast, the treatment by physical means can remove contaminants and oxides in a relatively simple manner while minimizing damage to the underlay. The material which is treated by physical means may be selected from a wide variety.

Among several physical means, plasma surface treatment is highly effective and preferable. The plasma surface treatment (to be referred to as "plasma treatment," hereinafter) means that active electrons, radicals, ions and molecules in a plasma interact with the insulating substrate surface to exert etching and implantation effects for thereby modifying the surface state.

The plasma to be generated varies with the plasma generating atmosphere and is generally divided into oxygen plasma and hydrogen plasma depending on the gas species used. Use of both oxygen plasma and hydrogen plasma is preferred. Oxygen plasma is effective for removal of surface organic contaminants and surface modification, and hydrogen plasma is able to reduce metal oxides.

In the third embodiment of the invention wherein contaminants and/or oxides on the uppermost surface layer of the insulating substrate are removed by plasma-assisted physical means, the adhesion between the humidity sensitive thin film and the insulating substrate is presumably enhanced by the two mechanisms described below.

First, contaminants and oxides on the uppermost surface layer serve as a weak "boundary layer" at the interface between the humidity sensitive thin film and the insulating substrate. The adhesion is strengthened by removal of this boundary layer.

Secondly, the removal of contaminants and/or oxides on the uppermost surface layer renders the insulating substrate surface more wettable so that upon application of the humidity sensitive thin film-forming monomer, the monomer can reach and penetrate into pores in the insulating substrate, and after polymerization, the humidity sensitive thin film is bound and rooted to the insulating substrate to provide the "anchor" effect of tightly bonding the humidity sensitive thin film to the insulating substrate.

In the third embodiment of the invention, it is believed that the latter effect provides a predominant contribution.

The method of the invention according to the third embodiment wherein contaminants and/or oxides on the uppermost surface layer of the insulating substrate are removed by physical means before a humidity sensitive thin film is formed is applicable to not only the humidity sensitive thin film which is comprised of a polymer obtained from a monomer of formula (1), but also the humidity sensitive thin film which is comprised of a polymer obtained from a monomer having an ethylenically unsaturated reactive group, preferably a monomer having an ethylenically unsaturated reactive group and a quaternary ammonium salt. In either case, the adhesion between the humidity sensitive thin film and the insulating substrate is improved. It is noted that the quaternary ammonium salts include, in a narrow sense, quaternary ammonium salts which are ammonium salts having four alkyl groups bonded to a nitrogen atom and, in a broad sense, ammonium type salts resulting from primary to tertiary amines.

DESCRIPTION OF THE PREFERRED EMBODIMENT

Figure 1:
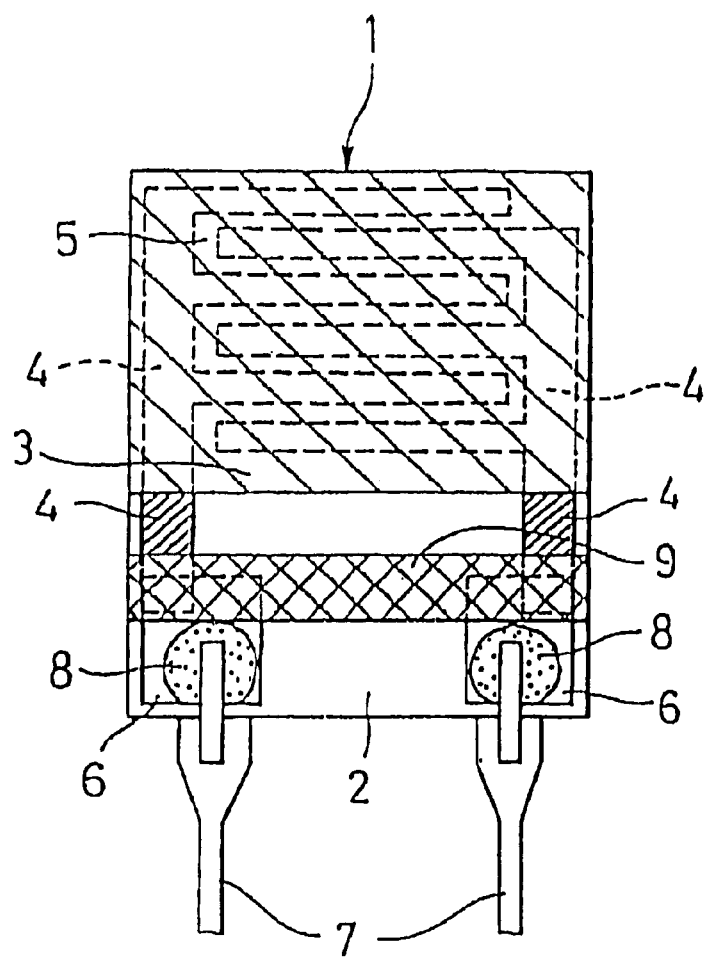
FIG. 1 is a plan view of a humidity sensor device according to one embodiment of the invention.

Now the present invention is described in detail.

The humidity sensor device of the invention includes an insulating substrate, a pair of opposed electrodes disposed on the substrate to define a gap therebetween, and a humidity sensitive thin film lying on the gap.

The humidity sensitive thin film is comprised of a copolymer of a monomer of formula (1) with a monomer of formula (2).

The monomer of formula (1) is described.

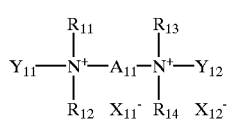
(1)

In formula (1), $A_{11}$ is a divalent group. $R_{11}$, $R_{12}$, $R_{13}$ and $R_{14}$ each are an alkyl group and they may be the same or different. $Y_{11}$ and $Y_{12}$ each are a monovalent group terminated with an ethylenically unsaturated reactive group, and they may be the same or different. Any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom. $X_{11}^-$ and $X_{12}^-$ each are an anion and they may be the same or different.

The divalent group represented by $A_{11}$ is preferably an alkylene, alkenylene or arylene group or a mixture thereof. These groups may have substituents, for example, alkyl groups such as methyl, and carbamoyl groups.

The alkylene groups preferably have 1 to 20 carbon atoms in total.

The alkenylene groups preferably have 2 to 10 carbon atoms in total.

The arylene groups preferably have 6 to 20 carbon atoms in total.

When the divalent group is a mixture of these groups, the mixture preferably has 3 to 20 carbon atoms in total.

Illustrative, preferred examples of $A_{11}$ include —$(CH_2)_m$— wherein m is an integer of 1 to 20, —$CH_2CH=CH—CH_2$—, —$CH(CH_3)$—$CH_2$—$CH_2$—, and —$C_6H_4$—$C_6H_4$—, with —$(CH_2)_m$— wherein m is an integer of 1 to 20 being especially preferred.

As indicated above, $A_{11}$ is preferably an unsubstituted straight alkylene group wherein m is preferably about 3 to about 16 although m is determined depending on $X_{11}^-$, $X_{12}^-$ or the type and copolymerization ratio of the monomer of formula (2) to be copolymerized therewith.

The monovalent groups terminated with an ethylenically unsaturated reactive group represented by $Y_{11}$ and $Y_{12}$ are preferably acrylic, for example, groups having an acryloyloxyalkyl, methacryloyloxyalkyl, acryloylaminoalkyl and methacryloylaminoalkyl group, and preferably alkylene acrylate or methacrylate groups or alkylene acrylate or methacrylate amide groups. The total number of carbon atoms in $Y_{11}$ or $Y_{12}$ is preferably 4 to 8. $Y_{11}$ and $Y_{12}$ are generally the same, but may be different from each other.

The alkyl groups represented by $R_{11}$ to $R_{14}$ are generally unsubstituted ones, but may have substituents, and preferably contain 1 to 5 carbon atoms in total. Examples include methyl, ethyl and propyl, with methyl being especially preferred. $R_{11}$ to $R_{14}$ are generally the same, but may be different from each other.

Any two or more of $R_{11}$ to $R_{14}$, $Y_{11}$, $Y_{12}$, $A_{11}$ and portions thereof adjoining the nitrogen (N) atom, taken together, may form a ring with the nitrogen (N) atom although it is preferred that they do not form a ring.

The anions represented by $X_{11}^-$ and $X_{12}^-$ are preferably halide ions, for example, chloride, bromide and iodide ions. Chloride and bromide ions are preferred, and chloride ions are most preferred. $X_{11}^-$ and $X_{12}^-$ are generally the same, but may be different from each other.

As indicated above, the monomer of formula (1) is preferably a difunctional monomer having an acrylic unsaturated reactive group at either end.

The monomer of formula (1) used herein is obtained as follows. Illustratively, the monomer of formula (1) is synthesized according to the following scheme.

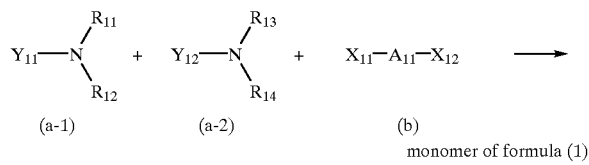

(a-1)　　　　　(a-2)　　　　　(b)

monomer of formula (1)

It is noted that $Y_{11}$, $Y_{12}$, $R_{11}$ to $R_{14}$, and $A_{11}$ in the above scheme are as defined for formula (1). Reference is made to the example in which $X_{11}$ and $X_{12}$ are halogen atoms.

First, acrylic amine compounds (a-1, a-2) are reacted with a dihalogen compound (b) to form a monomer of formula (1) containing a quaternary ammonium salt and having an acrylic unsaturated group at either end. In this stage, the amount of acrylic amine compounds added is at least 2 moles, especially 2.0 to 3.0 moles per mole of the dihalogen compound.

The reaction is carried out by stirring the reactants in an aprotic polar solvent such as acetonitrile or dioxane at about 50° C. for several days. If the reactants are subject to reflux in an alcohol such as methanol, isopropanol, methoxyethanol or 2-ethoxyethanol as the solvent, ester interchange can occur, failing to produce the desired diacrylic quaternary ammonium salt. Therefore, the alcoholic solvents which can trigger ester interchange reaction are not suitable.

At the end of reaction, acetone or the like is added to the reaction solution whereby the desired quaternary ammonium salt precipitates. The white precipitate thus obtained is filtered out. Acetone washing and drying yields the end compound.

The compounds used in introducing ethylenically unsaturated reactive groups, preferably acrylic unsaturated reactive groups into the monomer of formula (1) at both ends thereof are not critical as long as they have ethylenically unsaturated reactive groups, preferably acrylic unsaturated reactive groups such as acryloyloxy, methacryloyloxy, acryloylamino, methacryloylamino, diacryloylamino, and dimethacryloylamino groups. The preferred compounds are dialkylaminoethyl acrylates or methacrylates and dialkylaminoethyl acrylate or methacrylate amides. Illustrative examples are given below:

dimethylaminoethyl acrylate, dimethylaminopropyl acrylate amide, dimethylaminoethyl methacrylate, dimethylaminoethyl methacrylate amide, dimethylaminopropyl methacrylate, dimethylaminopropyl methacrylate amide, dimethylaminobutyl methacrylate, dimethylaminopentyl methacrylate, dimethylaminohexyl methacrylate, dimethylaminooctyl methacrylate, dimethylaminooctyl methacrylate amide, etc.

Examples of the dihalogen compounds to be reacted therewith include 1,3-dichloropropane, 1,4-dichlorobutane, 1,5-dichloropentane, 1,6-dichlorohexane, 1,8-dichlorooctane, 1,10-dichlorodecane, 1,12-dichlorododecane, 1,3-dibromopropane, 1,4-dibromobutane, 1,5-dibromopentane, 1,6-dibromohexane, 1,8-dibromooctane, 1,10-dibromodecane, and 1,12-dibromododecane.

The molecular weight of the monomer of formula (1) is not critical although it is generally 650 or lower when the preferred $A_{11}$ or the like is taken into account. The lower limit is not critical although it is generally about 370.

Described below is the monomer of formula (2) which is used along with the monomer of formula (1) to produce the copolymer contained in the humidity sensitive thin film according to the first embodiment of the invention.

Formula (2) is described.

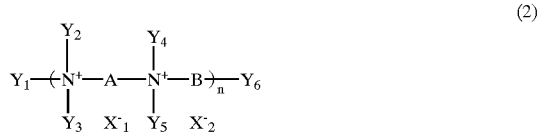

In formula (2), $Y_1$ to $Y_6$ each are a monovalent group, and at least one of $Y_1$ to $Y_6$ is a group terminated with an ethylenically unsaturated reactive group. Exemplary groups include acryloyloxy, methacryloyloxy, acryloylamino, methacryloylamino, vinyl, allyl, diallylmethyl, allyloxy, diacryloylamino and dimethacryloylamino groups as well as groups having the foregoing groups introduced therein.

Examples of the groups, other than the group terminated with an ethylenically unsaturated reactive group, represented by $Y_1$ to $Y_6$ include alkyl groups, alkenyl groups and halogen atoms. Examples of the alkyl and alkenyl groups are as exemplified for $R_1$ or the like in formulae (3) and (4) which are preferred among formula (2), and will be described later in conjunction with formulae (3) and (4). The halogen atoms include chlorine, bromine, iodine, etc. Any two or more of $Y_1$ to $Y_5$, A and portions thereof, or any two or more of $Y_4$ to $Y_6$, B and portions thereof, taken together, may form a ring with the nitrogen (N) atom. The ring thus formed is the same as the ring formed by $R_1$ or the like in formulae (3) and (4), and will be described later.

As indicated above, the monomer of formula (2) may have at least one ethylenically unsaturated reactive group and most often, preferably about two such groups.

The monovalent groups represented by $Y_2$ to $Y_5$ each may contain a chain for linking recurring units in the molecular structure represented by formula (2) and in this case, the recurring units in formula (2) may be the same or different.

It is noted that A, B, n, $X_1^-$ and $X_2^-$ in formula (2) have the same meaning as those in formulae (3) and (4) and will described all together in conjunction with formulae Among the monomers of formula (2), monomers of formulae (3) and (4) are preferred. Formulae (3) and (4) are described below.

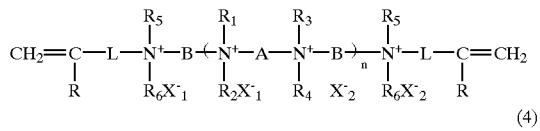

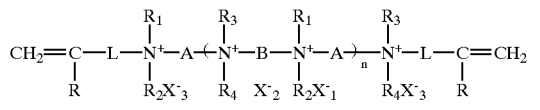

In formulae (3) and (4), A and B each are a divalent group.

The divalent group represented by A is preferably an alkylene, alkenylene or arylene group or a mixture thereof. These groups may have substituents, for example, hydroxyl groups, alkyl groups such as methyl, and carbamoyl groups.

The alkylene groups preferably have 1 to 20 carbon atoms in total and if substituted, they preferably have 1 to 5 hydroxyl groups.

The alkenylene groups preferably have 2 to 10 carbon atoms in total.

The arylene groups preferably have 6 to 20 carbon atoms in total.

When the divalent group is a mixture of these groups, the mixture preferably has 3 to 20 carbon atoms in total.

Illustrative, preferred examples of A include —$(CH_2)_m$— wherein m is an integer of 1 to 20, —$CH_2CH=CH$— $CH_2$—, —$CH_2$—CH(OH)—$CH_2$—, —CH($CH_3$)—$CH_2$— $CH_2$—, —$C_6H_4$—$C_6H_4$—, and —$C_6H_4$—CH(OH)— $C_6H_4$—.

Among others, A is preferably an unsubstituted alkylene group, especially straight —$(CH_2)_m$— wherein m is preferably about 3 to about 16 although m is determined depending on B, $X_1^-$, $X_2^-$ or the type and copolymerization ratio of the monomer of formula (1) to be copolymerized therewith.

The divalent groups represented by B include alkylene groups, alkylene groups which are separated by at least one of oxy (—O—) and carbonyl (—CO—), alkenylene groups, arylene groups, and mixtures thereof, which may be substituted with hydroxyl groups or alkenyl groups such as vinyl.

The alkylene groups preferably have 1 to 20 carbon atoms in total and if substituted, they preferably have 1 to 5 hydroxyl groups. When alkylene groups are separated by —O— and/or —CO—, the preferred number of such intervening groups is 1 to 5 in total.

The alkenylene groups preferably have 2 to 10 carbon atoms in total. The arylene groups preferably have 6 to 20 carbon atoms in total. When the divalent group is a mixture of these groups, the mixture preferably has 3 to 20 carbon atoms in total.

Illustrative, preferred examples of B include —$(CH_2)_m$— wherein m is an integer of 1 to 20, —$(CH_2)_2$—CH(OH)— $CH_2$—, —$CH_2$—CH(OH)—$CH_2$—, —$CH_2$—CH=CH— $CH_2$—, —$CH_2$—CH(CH=$CH_2$)—, —($CH_2$— $CH_2$—O)$_2$—$(CH_2)_2$—, —$CH_2$—(CO)—$CH_2$—, and —$CH_2$—$C_6H_4$—$CH_2$—, Among others, B is preferably an unsubstituted alkylene group, especially straight —$(CH_2)_m$— wherein m is preferably about 3 to about 16 although m is determined depending on A, $X_1^-$, $X_2^-$ or the type and copolymerization ratio of the monomer of formula (1) to be copolymerized therewith.

Each of $R_1$, $R_2$, $R_3$ and $R_4$ is an alkyl or alkenyl group.

The alkyl groups represented by $R_1$ to $R_4$ are preferably those of 1 to 10 carbon atoms, and may have substituents, but are preferably unsubstituted. Preferred examples include methyl, ethyl, propyl and butyl.

The alkenyl groups represented by $R_1$ to $R_4$ are preferably those of 2 to 10 carbon atoms, and may have substituents, but are preferably unsubstituted. Preferred examples include vinyl, allyl, propenyl and butenyl.

$R_1$ and $R_2$, $R_1$ and A or a portion of A, $R_2$ and A or a portion of A, $R_3$ and $R_4$, $R_3$ and A or a portion of A, $R_4$ and A or a portion of A, $R_1$ and $R_3$ or $R_4$, or $R_2$ and $R_3$ or $R_4$, taken together, may form a ring with the nitrogen (N) atom. These rings are preferably 5- or 6-membered rings, especially 6-membered nitrogenous heterocycles and may even bridged rings. Preferred examples of the nitrogenous heterocycles include pyridine, 1,4-azabicyclo[2.2.2]octane, piperidine, piperazine and pyrazine rings, which may be substituted with carbamoyl or other groups.

In formula (3), $R_5$ and $R_6$ each are an alkyl or alkenyl group. Of these, alkyl groups are preferred, with those of 1 to 10 carbon atoms being especially preferred. The alkyl groups may have substituents, but are preferably unsubstituted. Methyl and ethyl are preferred groups. Examples of the alkenyl groups represented by $R_5$ and $R_6$ are as exemplified for $R_1$ to $R_4$.

In formulae (3) and (4), L is a divalent group. Preferred examples of L in formula (3) include —COO($CH_2$)$_2$—, —CONH($CH_2$)$_3$—, and —$(CH_2)_m$— wherein m is an integer of 1 to 20. Preferred examples of L in formula (4) include —O$CH_2$$CH_2$—, —$(CH_2)_m$— wherein m is an integer of 1 to 20, —COO($CH_2$)$_2$—, —COO$CH_2$CH(OH)$CH_2$—, and —$CH_2$—$C_6H_4$—(p- or m-form).

It is noted that in formula (3), any two or three of $R_5$, $R_6$ and L, suitably taken together, may form a pyridine or analogous ring with the nitrogen (N) atom.

In formulae (3) and (4), R is hydrogen or an alkyl group, and preferably hydrogen or methyl.

In formulae (3) and (4), $X_1^-$ and $X_2^-$ are anions, preferably halide ions, for example, chloride, bromide and iodide ions, with chloride and bromide ions being preferred. $X_1^-$ and $X_2^-$ are generally the same, but may be different from each other. In formula (4), $X_3^-$ is an anion. For two $X_3^-$ in formula (4), the identical symbol is used in accordance with the synthesis scheme to be described later, and they are generally the same, but may be different from each other. Illustrative examples and preferred examples of $X_3^-$ are the same as those of $X_1^-$ and $X_2^-$. Most often, $X_1^-$, $X_2^-$ and $X_3^-$ are the same. The letter n is a number of 2 to 5,000.

The monomers of formulae (2), (3) and (4) are regarded as polymers comprising specific recurring units and having a number average molecular weight Mn of about 1,000 to about 1,000,000.

The monomer of formula (3) can be synthesized according to the scheme shown below. Reference is made to the example wherein $X_1^-$ and $X_2^-$ are halide ions. The symbols used in the scheme are as defined previously.

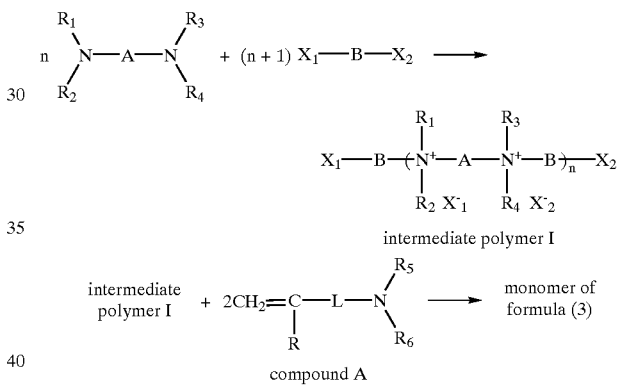

intermediate polymer I intermediate polymer I + 2$CH_2$=C—L—N $\overset{R_5}{\underset{R_6}{\diagdown}}$ ⟶ monomer of formula (3)

compound A

First, a diamine compound is reacted with a dihalogen compound to form an intermediate polymer I having a quaternary ammonium salt and terminal groups which are halogen. At this stage, reaction may be carried out under such conditions that 1.0 to 2.0 moles of the dihalogen compound is available per mole of the diamine compound. In order to ensure that the terminal groups of intermediate polymer I be halogen, the dihalogen compound may be added in two divided portions. It is recommended herein that the first portion of the dihalogen compound be 1 to 1.3 moles per mole of the diamine compound, and the balance be added as the second portion.

The reaction is carried out in a nonaqueous solvent such as methanol, isopropanol, methoxyethanol or 2-ethoxyethanol at a reflux temperature or a temperature of about 100° C. for about 5 to about 100 hours.

Next, a compound having an ethylenically unsaturated reactive group, A, is reacted with the intermediate polymer I for introducing ethylenically unsaturated reactive groups into the intermediate polymer I at both ends, to thereby form the monomer of formula (3). The reaction of this stage may be carried out subsequent to the reaction of the preceding stage. Specifically, the compound having an ethylenically unsaturated reactive group, A, in a substantially equimolar amount to the dihalogen compound, is added to the reaction solution whereupon reaction is carried out at a temperature of about 15 to about 100° C. for about 10 to about 150 hours.

Thereafter, the reaction solution is added dropwise to a solvent such as acetone or ethyl acetate whereupon a precipitate forms. The precipitate is collected by filtration and purified, obtaining the end compound.

On the other hand, the monomer of formula (4) can be synthesized according to the scheme shown below. Reference is made to the example wherein $X_1^-$ and $X_2^-$ are halide ions. The symbols used in the scheme are as defined previously. It is preferred that $X_3^-$ be a halide ion as well.

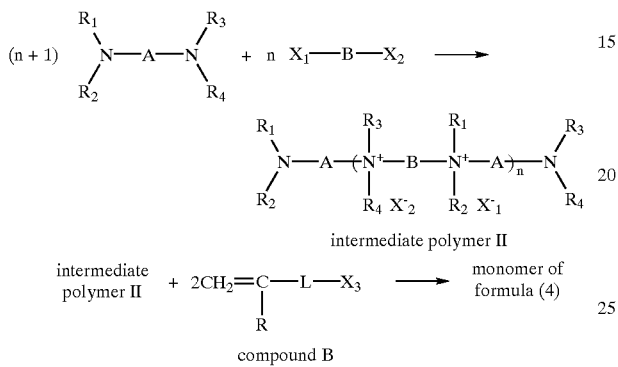

First, a diamine compound is reacted with a dihalogen compound to form an intermediate polymer II having a quaternary ammonium salt and terminal groups which are amino groups. At this stage, reaction may be carried out under such conditions that 1.1 to 2.0 moles of the diamine compound is available per mole of the dihalogen compound. Reaction conditions other than this are the same as used above in the formation of intermediate polymer I. The same means as above may be taken to ensure that the terminal groups be amino groups.

Next, a compound having an ethylenically unsaturated reactive group, B, is reacted with the intermediate polymer II for introducing ethylenically unsaturated reactive groups into the intermediate polymer II at both ends, to thereby form the monomer of formula (4). The reaction of this stage may be carried out in the same manner as used for the monomer of formula (3).

The monomer of formula (3) or (4) is obtained by reaction of a diamine compound with a dihalogen compound. Any desired diamine compound and dihalogen compound may be used herein as long as they can follow the reaction according to the above scheme. It is noted that the monomers and intermediate polymers are typically obtained as a mixture of oligomers having a degree of polymerization (n) of about 2 to 20 and polymers having a degree of polymerization (n) of more than 20.

Preferred examples of the diamine compound are given below.

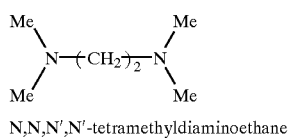

N,N,N',N'-tetramethyldiaminoethane

A-1

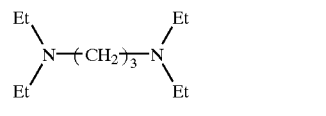

N,N,N',N'-tetraethyl-1,3-propanediamine

A-2

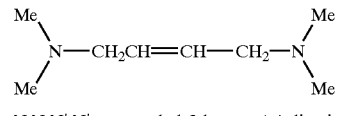

N,N,N',N'-tetramethyl-2-butene-1,4-diamine

A-3

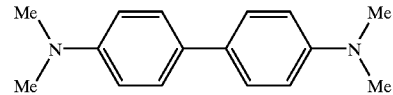

N,N,N',N'-tetramethylbenzidine

A-4

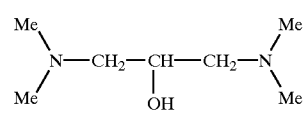

1,3-bis(dimethylamine)-2-propanol

A-5

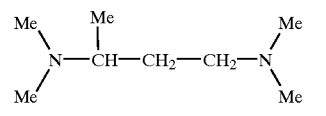

N,N,N',N'-tetramethyl-1,3-diaminobutane

A-6

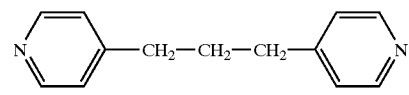

1,3-di(4-pyridyl)propane

A-7

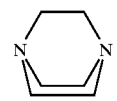

1,4-diazabicyclo[2.2.2]octane

A-8

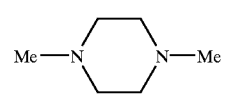

N,N'-dimethylpiperadine

A-9

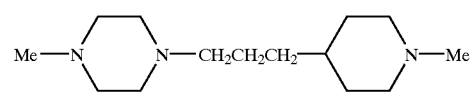

N,N'-dimethyl-1,3-di-4-piperidylpropane

A-10

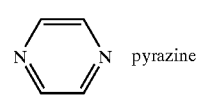 pyrazine

A-11

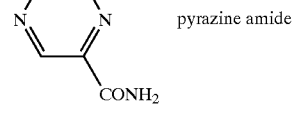 pyrazine amide

A-12

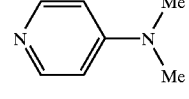 4-dimethylaminopyridine

A-13

A-14

Me₂N–C₆H₄–CH(OH)–C₆H₄–NMe₂

4,4′-bisdimethylaminobenzhydrol

A-15

Me₂N–(CH₂)₆–NMe₂

N,N,N′,N′-tetramethyl-1,6-hexanediamine

A-16

Me₂N–(CH₂)₅–NMe₂

N,N,N′,N′-tetramethyl-1,5-pentanediamine

A-17

Me₂N–(CH₂)₄–NMe₂

N,N,N′,N′-tetramethyl-1,4-butanediamine

A-18

Me₂N–(CH₂)₃–NMe₂

N,N,N′,N′-tetramethyl-1,3-propanediamine

A-19

Me₂N–(CH₂)₁₂–NMe₂

N,N,N′,N′-tetramethyl-1,12-dodecanediamine

Preferred examples of the dihalogen compound are given below.

B-1: $X-(CH_2)_2-X$

B-2: $X-CH_2-CH(OH)-CH_2-X$

B-3: $X-CH_2-CH_2-CH(OH)-CH_2-X$

B-4: $X-CH_2-CH=CH-CH_2-X$

B-5: $X-(CH_2)_4-O-(CH_3)_4-X$

B-6: $X-CH_2-CH_2-O-CH_2CH_2-O-CH_2-CH_2-X$

B-7: $X-CH_2-C(=O)-CH_2-X$

B-8: $X-CH_2-C_6H_4-CH_2-X$

B-9: $X-(CH_2)_3-X$

B-10: $X-(CH_2)_4-X$

B-11: $X-(CH_2)_5-X$

B-12: $X-(CH_2)_6-X$

B-13: $X-(CH_2)_9-X$

B-14: $X-(CH_2)_{10}-X$

B-15: $X-(CH_2)_{12}-X$

B-16: $X-(CH_2)_{16}-X$

In these examples, X is a halogen atom, with chlorine and bromine atoms being preferred.

Examples of the intermediate polymers to the monomers of formulae (3) and (4) are shown below as polymers resulting from combinations of the diamine and dihalogen compounds illustrated just above. Note that numerical values in the parentheses represent a molar ratio.

(1) Polymer resulting from a combination of A-16/B-10 (50/50)
(2) Polymer resulting from a combination of A-8/B-12/B-10 (50/48/2)
(3) Polymer resulting from a combination of A-8/B-13/B-10 (50/48/2)
(4) Polymer resulting from a combination of A-8/B-15/B-10 (50/48/2)
(5) Polymer resulting from a combination of A-16/B-2 (50/50)
(6) Polymer resulting from a combination of A-7/B-10 (50/50)
(7) Polymer resulting from a combination of A-2/B-10 (50/50)
(8) Polymer resulting from a combination of A-9/B-10 (50/50)
(9) Polymer resulting from a combination of A-16/B-9 (50/50)
(10) Polymer resulting from a combination of A-3/A-8/B-10 (2/48/50)
(11) Polymer resulting from a combination of A-14/A-16/B-17 (49/1/50)
(12) Polymer resulting from a combination of A-11/B-16 (50/50)
(13) Polymer resulting from a combination of A-6/B-4/B-15 (50/47/3)
(14) Polymer resulting from a combination of A-11/B-6 (50/50)
(15) Polymer resulting from a combination of A-13/B-3 (50/50)
(16) Polymer resulting from a combination of A-10/B-15 (50/50)
(17) Polymer resulting from a combination of A-15/B-16 (50/50)
(18) Polymer resulting from a combination of A-4/B-10 (50/50)
(19) Polymer resulting from a combination of A-10/B-12/B-10 (50/48/2)
(20) Polymer resulting from a combination of A-8/B-2 (50/50)
(21) Polymer resulting from a combination of A-7/A-16/B-10 (15/35/50)
(22) Polymer resulting from a combination of A-8/A-16/B-10 (15/35/50)
(23) Polymer resulting from a combination of A-9/A-16/B-10 (15/35/50)
(24) Polymer resulting from a combination of A-10/A-16/B-10 (15/35/50)
(25) Polymer resulting from a combination of A-8/B-13 (50/50)

(26) Polymer resulting from a combination of A-8/A-10/B-13 (15/35/50)

(27) Polymer resulting from a combination of A-8/B-13/B-10 (50/40/10)

(28) Polymer resulting from a combination of A-8/B-13/B-2 (50/40/10)

(29) Polymer resulting from a combination of A-9/B-13 (50/50)

(30) Polymer resulting from a combination of A-8/A-9/B-13 (25/25/50)

(31) Polymer resulting from a combination of A-9/A-10/B-13 (25/25/50)

(32) Polymer resulting from a combination of A-19/B-15 (50/50)

(33) Polymer resulting from a combination of A-15/B-9 (50/50)

(34) Polymer resulting from a combination of A-15/B-15 (50/50)

The compounds A and B used in introducing ethylenically unsaturated reactive groups into intermediate polymers I and II at both ends are not critical as long as they have an ethylenically unsaturated reactive group such as an acryloyloxy, methacryloyloxy, acryloylamino, methacryloylamino, vinyl, allyl, diallylmethyl, allyloxy, diacryloylamino, and dimethacryloylamino group. Where intermediate polymers I and II as produced already have an ethylenically unsaturated reactive group at an end as in the case of, for example, polymers (10), (11) and (13), they may be used as the monomer in the practice of the invention without further reaction.

Preferred examples of compound A used in combination with intermediate polymer I are given below.

E-1 $CH_2=CHCO_2C_2H_4NMe_2$
E-2 $CH_2=CHCONHC_3H_6NMe_2$

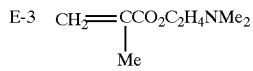

Preferred examples of compound B used in combination with intermediate polymer II are given below.

F-1 $CH_2=CHOCH_2CH_2X$

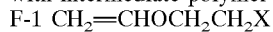

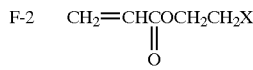

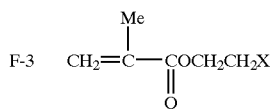

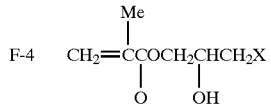

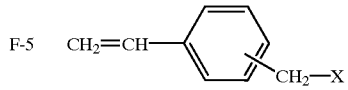

(mixture of p- and m-forms)

In the above formulae, X is a halogen atom, and preferably chlorine and bromine.

The copolymer according to the first embodiment of the invention is obtained by applying a mixed solution of the monomer of formula (1), the monomer of formula (2) and a photo-polymerization initiator onto a substrate to form a coating, drying and irradiating UV radiation for polymerization. For each monomer type, one or more monomers may be used.

The mixing ratio of the monomer of formula (1) to the monomer of formula (2) is determined in accordance with the intrinsic impedance of each monomer, the degree of crosslinking upon mixing, and the shape of electrodes on the substrate. Therefore, the mixing ratio differs case by case and is not determined within a certain range. Usually, the molar ratio of the monomer of formula (1) to the monomer of formula (2) is from about 10:1 to about 1:10.

As the polymerization initiator, any of commercially available polymerization initiators such as benzophenone derivatives may be used.

In the first embodiment of the invention, polymerization is preferably carried out by irradiation of UV radiation although polymerization may also be induced by heating and preferably by heating followed by UV irradiation.

The humidity sensitive thin film obtained by copolymerization reaction of quaternary ammonium salt monomers of formulae (1) and (2), preferably difunctional ammonium salts is not only very robust due to three-dimensional crosslinking, but also the quaternary ammonium salt has an ionene structure of the so-called backbone type and does not have a structure with a high degree of freedom like the pendant type structure. Therefore, the film maintains a humidity sensitive curve with minimal hysteresis.

While the humidity sensitive thin film according to the first embodiment of the invention contains a crosslinked product of the copolymer resulting from reaction of the monomer of formula (1) with the monomer of formula (2) as indicated above, formation of the humidity sensitive thin film is preferably carried out by the following procedure.

A coating solution containing the monomer of formula (1) and the monomer of formula (2) is prepared. In this regard, one monomer of formula (1) and one monomer of formula (2) are used in most cases although two or more different monomers may be used for each type or for either one of the two types. The monomers used herein are preferably those having a halide ion as the anion, more preferably a chloride or bromide ion. It is especially preferred to use at least one monomer having a chloride ion.

The coating solution is an aqueous solution or an alcoholic or organic solvent solution or a mixture thereof which contains the monomers in a predetermined ratio and in a concentration of 1 to 10% by weight. When the copolymer is to be later crosslinked by exposure to radiation, especially UV radiation, a photo-polymerization initiator (e.g., water-soluble benzophenone compound) is preferably added in a concentration of 0.03 to 0.7% by weight.

Although the humidity sensitive thin film obtained according to the first embodiment of the invention does not peel from the substrate because the swell of the film is reduced as compared with conventional films, the following treatment may be further carried out in order to ensure the adhesion to the substrate and provide higher water resistance.

An acrylic silane coupling agent which is an acrylic monomer having a functional group (alkoxysilyl group) capable of reacting with the substrate or electrode, such as γ-methacryloxypropyltrimethoxysilane is copolymerized. In an alternative procedure, the substrate (usually electrode-bearing substrate) is treated with an acrylic silane coupling agent and heated, then a solution containing the monomer of formula (1) and the monomer of formula (2) is applied, dried, and copolymerized. In the former procedure, after the humidity sensitive thin film is formed by copolymerization, it is preferably held at a high humidity (i.e., in the presence of water vapor) for improving adhesion.

Convenient examples of the acrylic silane coupling agent include γ-methacryloxypropylmethyldimethoxysilane, γ-methacryloxypropyltrimethoxysilane, γ-methacryloxypropylmethyldiethoxysilane and γ-methacryloxypropyltriethoxysilane, which are commercially available as KBM502, KBM503, KBE502 and KBE503, respectively, from Shin-Etsu Chemical Co., Ltd.

The insulating substrate used herein may be formed of any desired material which has on the surface functional groups such as hydroxyl groups to ensure adhesion to the humidity sensitive thin film and is electrically insulating. Use may be made of glass, plastics such as phenolic resins and epoxy resins, ceramics and metals coated with resins having hydroxyl or similar groups. The electrodes may be made of any conventional electrode material. For example, they are formed by screen printing low resistance paste containing Au or $RuO_2$ and optionally glass frit, followed by high temperature firing. It is noted that in the case of oxide electrodes such as $RuO_2$, hydroxyl or similar functional groups on their surface contribute to an improvement in adhesion to the humidity sensitive thin film.

In the first embodiment of the invention, instead of the above-mentioned method using the acrylic monomer having an alkoxysilyl group, it is acceptable to use a method involving removing contaminants and/or oxides on the uppermost surface layer of the insulating substrate by physical means, then forming a humidity sensitive thin film for thereby improving the adhesion between the humidity sensitive thin film and the substrate. The detail of this method will be described later.

Where treatment resorts to physical means, the treatment alone is sufficient because it is possible to provide satisfactory adhesion to the humidity sensitive thin film. However, a combined method is acceptable in which the interdigital electrode-bearing substrate after the treatment is further treated with the aforementioned acrylic monomer having an alkoxysilyl group (e.g., acrylic silane coupling agent).

In the first embodiment of the invention, using the coating solution, preferably by coating, a humidity sensitive thin film is formed on the insulating substrate having electrodes borne thereon as indicated above. Any desired coating technique may be used as long as a predetermined amount can be applied to the insulating substrate. Various techniques such as dipping, dispensing, brush coating, gravure coating, screen printing, and spin coating techniques are useful. A choice may be made depending on the overall procedure and the type and application of a final product.

After the coating is formed in this way, it is dried and/or thermally crosslinked at a temperature of about 15 to 100° C. for about 3 to 15 minutes and then crosslinked with radiation. Crosslinking by exposure to radiation is preferably by exposure to UV radiation. It is noted that crosslinking progresses along with copolymerization.

Crosslinking by exposure to UV radiation may be carried out by any well-known technique. Often UV radiation having an intensity of at least about 80 mW/cm$^2$ is irradiated in an exposure of about 200 to 2,500 mJ/cm$^2$. Conventional light sources such as mercury lamps may be used as the UV source.

The humidity sensitive thin film as crosslinked preferably has a thickness of about 0.5 to 10 μm, especially about 3 to 10 μm. Film thickness outside this range is undesirable because a thicker film would be slow in response of its electric resistance to humidity whereas a thinner film would produce lower outputs in the low humidity region and be less resistant to gas.

In the second embodiment of the present invention, the humidity sensitive thin film contains a crosslinking copolymer of a monomer of formula (1) with an acrylic monomer having an alkoxysilyl group. Due to reaction of hydroxyl or other functional groups on the substrate surface and/or electrode surface with the alkoxysilyl groups within the molecule, the humidity sensitive thin film is bound to the substrate and electrode.

The monomer of formula (1) used herein is the same as used in the humidity sensitive thin film according to the first embodiment of the invention, the divalent group represented by $A_{11}$ in formula (1) is as defined previously, and preferably —$(CH_2)_m$— wherein m is an integer of 1 to 20.

On the other hand, the acrylic monomer having an alkoxysilyl group to be copolymerized with the monomer of formula (1) is a monomer having an acrylic unsaturated reactive group, with no other particular limits being imposed thereon. Methacrylic monomers are preferred.

Any alkoxysilyl groups are useful as long as they can react with functional groups on the substrate and/or electrode surface such as hydroxyl groups on the surface of an alumina substrate or oxide electrodes. Those alkoxysilyl groups are preferred in which the alkoxy moiety has 1 to 5 carbon atoms in total, and especially the alkoxy group is methoxy or ethoxy. Further, the number of alkoxy groups bonding to Si is preferably 2 or 3, and the groups, other than the acrylic unsaturated reactive group-bearing group and alkoxy group, bonding to Si are alkyl groups or the like, preferably having 1 to 5 carbon atoms, and especially methyl.

Convenient examples of the acrylic monomer having an alkoxysilyl group include γ-methacryloxypropylmethyldimethoxysilane, γ-methacryloxypropyltrimethoxysilane, γ-methacryloxypropylmethyldiethoxysilane and γ-methacryloxypropyltriethoxysilane, which are commercially available as KBM502, KBM503, KBE502 and KBE503, respectively, from Shin-Etsu Chemical Co., Ltd.

It is possible to form a humidity sensitive thin film by dissolving the monomer of formula (1) in methanol or ethanol, applying the solution onto electrodes, and effecting polymerization by exposure to UV radiation. To ensure adhesion to the substrate and achieve high water resistance, in the second embodiment of the invention, the monomer is copolymerized with an acrylic silane coupling agent monomer having a functional group (alkoxysilyl group) capable of reacting with the substrate and electrodes, such as γ-methacryloxypropyltrimethoxysilane. Alternatively, after the substrate (often, electrode-bearing substrate) is treated with an acrylic silane coupling agent, the monomer of formula (1) is coated and polymerized. In either procedure, a copolymer of the monomer of formula (1) with the acrylic silane coupling agent monomer forms.

The ratio of the monomer of formula (1) to the silane coupling agent monomer is preferably between about 1:1 and about 1:0.01 in molar ratio. Too large an amount of the silane coupling agent monomer may degrade the humidity sensing function and impede low-humidity response. Too small an amount may lead to insufficient adhesion to the substrate and poor water resistance.

Synthesis of the copolymer in the humidity sensitive thin film is preferably carried out simultaneous with formation of the humidity sensitive thin film as follows.

A mixed solution containing the monomer of formula (1), the silane coupling agent monomer and a photo-polymerization initiator is applied onto a substrate to form a coating, dried and irradiated with UV radiation for polymerization. As the polymerization initiator, commercially available initiators such as benzophenone derivatives may be used. Then the coating is held at a high humidity (i.e., in the presence of water vapor) to promote reaction of hydroxyl or other functional groups on the substrate surface and/or electrode surface with alkoxysilyl or silanol groups, establishing a firm bond to the substrate. The firm bond resulting from reaction with functional groups on the substrate surface or electrode surface is confirmed by the finding that neither film separation nor output drops occur after water immersion. Alternatively, after the substrate (often electrode-bearing substrate) is treated with the silane coupling agent, the monomer of formula (1) is coated and polymerized, with equivalent results.

The humidity sensitive thin film obtained by reaction of the quaternary ammonium salt monomer of formula (1), preferably difunctional ammonium salt with the acrylic silane coupling agent is not only very robust due to three-dimensional crosslinking, but also the quaternary ammonium salt has an ionene structure of the so-called backbone type and does not have a structure with a high degree of freedom like the pendant type structure. Therefore, the film maintains a humidity sensitive curve with minimal hysteresis.

It is also preferred that chloride ions account for at least 30 mol %, especially at least 50 mol % of the halide ions that constitute the quaternary ammonium salt in the crosslinking copolymer. The inclusion of chloride ions facilitates movement of ions so that a fully linear response may be developed even in a low-humidity region of RH 0 to 50%.

Further, after covalent bonds are established by reaction of the substrate and/or electrode with alkoxysilyl or silanol groups, the separation of the film from the substrate is prevented and water resistance is significantly improved. Since the separation of the film from the substrate is prevented, the film thickness can be increased so that resistance to gases such as $Cl_2$, NOx, SOx, $H_2S$, HCl and $NH_3$ is improved. Additionally, the humidity sensitive thin film according to the invention does not lose gloss in the presence of a vapor of alcohol, acetone or hexane and is thus highly solvent resistant.

While the humidity sensitive thin film in the second embodiment of the invention contains a crosslinked product of a copolymer resulting from reaction of the monomer of formula (1) with the acrylic monomer having an alkoxysilyl group as indicated above, formation of the humidity sensitive thin film is preferably carried out by the following procedure.

A coating solution containing the monomer of formula (1) and the acrylic monomer having an alkoxysilyl group is prepared. In this regard, one monomer of formula (1) and one acrylic monomer having an alkoxysilyl group are used in most cases although two or more different monomers may be used for each type or for either one of the two types.

The coating solution is an aqueous solution or an alcoholic or organic solvent solution or a mixture thereof containing the monomers in a predetermined ratio and in a concentration of 1 to 10% by weight. When the copolymer is to be later crosslinked by exposure to radiation, especially UV radiation, a photo-polymerization initiator (e.g., water-soluble benzophenone compound) is preferably added in a concentration of about 0.03 to 0.7% by weight.

In the second embodiment of the invention, using the coating solution, preferably by coating, a humidity sensitive thin film is formed on the insulating substrate having electrodes borne thereon as indicated above. Any desired coating technique may be used as long as a predetermined amount can be applied to the insulating substrate. Various techniques such as dipping, dispensing, brush coating, gravure coating, screen printing, and spin coating techniques are useful. A choice may be made depending on the overall procedure and the type and application of a final product. It is noted that a solution to which all the components have been added may be used as the coating solution, while a procedure of first applying a coating solution of the acrylic monomer having an alkoxysilyl group and then applying a coating solution of the monomer of formula (1) is also acceptable as indicated above.

After the coating is formed in this way, it is dried and/or thermally crosslinked at a temperature of about 15 to 100° C. for about 3 to 15 minutes and then crosslinked with radiation. Crosslinking by exposure to radiation is preferably by exposure to UV radiation.

Crosslinking by exposure to UV radiation may be carried out by any well-known technique. Often UV radiation having an intensity of at least about 50 $mW/cm^2$ is irradiated in an exposure of about 200 to 2,500 $mJ/cm^2$. Conventional light sources such as mercury lamps may be used as the UV source.

The insulating substrate used in the second embodiment may be formed of any desired material which has on the surface functional groups such as hydroxyl groups to ensure adhesion to the humidity sensitive thin film and is electrically insulating. Use may be made of glass, plastics such as phenolic resins and epoxy resins, ceramics and metals insulation coated with resins having hydroxyl or similar groups. The electrodes may be made of any conventional electrode material. For example, they are formed by screen printing low resistance paste containing Au or $RuO_2$ and optionally glass frit, followed by high temperature firing. It is noted that in the case of oxide electrodes such as $RuO_2$, hydroxyl or similar functional groups on their surface contribute to an improvement in adhesion to the humidity sensitive thin film.

In the second embodiment, when the insulating substrate is treated with the acrylic monomer having an alkoxysilyl group as indicated above, this treatment is carried out on the insulating substrate on which electrodes (preferably interdigital electrodes) have been arranged.

In the third embodiment of the present invention wherein contaminants and/or oxides on the uppermost surface layer of the insulating substrate are removed by physical means before a humidity sensitive thin film is formed, the humidity sensitive thin film can be comprised of a polymer obtained from the monomer of formula (1) without using the monomer of formula (2) and the acrylic monomer having an alkoxysilyl group.

In this embodiment, formation of the humidity sensitive thin film can be carried out in the same manner as formation of the humidity sensitive thin film in the foregoing embodiments, using a coating solution containing the monomer of formula (1), and without using the monomer of formula (2) and the acrylic monomer having an alkoxysilyl group.

The treatment by physical means is carried out on the insulating substrate on which electrodes, preferably interdigital electrodes have been arranged.

The insulating substrate bearing a pair of interdigital electrode to be treated by physical means may be formed of any desired material which is not chemically reactive with the humidity sensitive thin film and is electrically insulating.

Use may be made of glass, plastics, ceramics and metal plates coated with insulating material. In particular, alumina is preferred for mechanical strength, insulation and stability.

Hereinafter, reference is made to the preferred use of an alumina substrate.

The surface layer of the insulating substrate bearing a pair of interdigital electrodes (to be referred to as interdigital electrode-bearing substrate) have much contaminants, adsorbed gases and organic matter adsorbed thereto during its preparation and storage. The uppermost surface layer of the alumina substrate is covered with oxides of the substrate itself or the like.

The contaminants, adsorbed gases and organic matter, except oxides, which are taken to the interdigital electrode-bearing substrate from the exterior as mentioned above, are designated together as contaminants, whereas oxide contaminants and the material of the insulating substrate itself are designated together as oxide.

More particularly, for example, organic matter floating in the surrounding atmosphere and residues of chemicals and additives used during preparation built up on the substrate. They, combined with the oxide of the substrate itself, serve to lower the wettability of the interdigital electrode-bearing substrate so that when a solution of the monomer of formula (1) is applied thereto, the solution may not spread over, and after polymerization, the humidity sensitive thin film remains less adherent to the substrate.

Therefore, in the third embodiment of the invention, contaminants and/or oxides on the uppermost surface layer are removed by treatment by physical means prior to the application of a solution of the monomer of formula (1).

Referring to an alumina substrate as a typical example, the uppermost surface layer occupies a region extending from the surface (including the uppermost surface layer) of the substrate to a depth of about 1 nm when contaminants are present on the surface, provided that pores are neglected. The removal of contaminants and oxides from the uppermost surface layer by physical means can be confirmed in terms of surface wettability. Most often, the contact angle with water becomes close to 0°. Removal treatment is carried out on contaminants and preferably on sub-surface layers of the electrodes and the substrate themselves (a region extending from the surface of the object to a depth of about 1 nm). It is therefore preferred to remove both contaminants and oxides. It is noted that excessive removal of the sub-surface layers of the electrodes and the substrate themselves is undesirably accompanied with configuration changes.

As the treatment by physical means, plasma flame treatment, UV/ozone treatment, excimer UV treatment, corona treatment, electron beam treatment, laser treatment, sputtering treatment, and plasma treatment may be used. Of these, plasma treatment is preferred because of minimized damage to the insulating substrate and low cost. UV/ozone treatment is applicable to some interdigital electrode-bearing substrates because of low cost, but when applied to alumina substrates, coloring is often found at the end of treatment. Coloring can be prevented by selecting treatment conditions.

Described below is the plasma treatment which is preferably employed in the third embodiment of the invention.

As previously described in the 'Operation' section, the organic matter-removing effect and the surface modifying effect that oxygen plasma exerts and the metal oxide-reducing effect that hydrogen plasma exerts are effective. Preferably, oxygen plasma treatment is performed alone, or oxygen plasma treatment is followed by hydrogen plasma treatment. From the standpoint of ease of operation, a plasma treatment with the aid of an inert gas introduced is also preferred.

The plasma treatment may be carried out under any conditions such as vacuum, inert gas and atmospheric pressure, as long as such conditions are relatively low temperature plasma conditions which do not cause damages to the interdigital electrode-bearing substrate. The apparatus used may be selected in accordance with treatment conditions. Among others, conditions in an inert gas and under atmospheric pressure are appropriate because a simple apparatus can be used. However, it is customary to carry out plasma treatment in vacuum while introducing oxygen or hydrogen as indicated above.

The plasma used in either of these methods is generated at a power supply frequency of several kHz to several hundred MHz, and the power is adjusted in accordance with the plasma generating conditions. Where the interdigital electrode-bearing substrate is alumina, satisfactory results are obtained by treating it at a high-frequency power in the range of 50 to 1,000 W for a time of 2 seconds to 10 minutes.

Following the plasma treatment of the interdigital electrode-bearing substrate, a solution of the monomer of formula (1) is applied to the substrate. The duration from the plasma treatment to the monomer coating is from 24 to 96 hours when the substrate is held in vacuum, and the monomer coating is preferably performed immediately or within 24 hours after the plasma treatment when the substrate is held in atmospheric pressure. When the substrate is held under inadequate storage conditions, the duration within which the surface state is maintained sound becomes short. It is then desired to carry out coating immediately after the plasma treatment in a continuous manner.

Where treatment resorts to physical means, the treatment alone is sufficient because it is possible to provide satisfactory adhesion to the humidity sensitive thin film. However, a combined method is acceptable in which the interdigital electrode-bearing substrate after the treatment is further treated with the aforementioned acrylic monomer having an alkoxysilyl group (e.g., acrylic silane coupling agent). Likewise, the treatment by physical means is effectively applicable to the humidity sensitive thin film comprising the copolymer of the monomer of formula (2) with the monomer of formula (1) as described above.

In the second and third embodiments of the invention, the humidity sensitive thin film as crosslinked preferably has a thickness of about 0.5 to 10 $\mu$m, especially about 3 to 10 $\mu$m. Film thickness outside this range is undesirable because a thicker film would be slow in response of its electric resistance to humidity whereas a thinner film would produce lower outputs in the low humidity region and be less resistant to gas and water.

The method of the invention according to the third embodiment wherein contaminants and/or oxides on the uppermost surface layer of the insulating substrate are removed by physical means before a humidity sensitive thin film is formed is applicable to not only the humidity sensitive thin film which is comprised of a polymer obtained from a monomer of formula (1), but also the humidity sensitive thin film which is comprised of a polymer obtained from a monomer having an ethylenically unsaturated reactive group, preferably a monomer having an ethylenically unsaturated reactive group and a quaternary ammonium salt. In the latter case too, the adhesion between the humidity sensitive thin film and the insulating substrate is improved.

The polymers of which the humidity sensitive thin film is formed in the latter case include the aforementioned copolymers of the monomer of formula (1) with the monomer of formula (2) and other polymers as will be described below.

Illustrative are polymers obtained from the monomer of formula (2), preferably polymers obtained from the monomer of formula (3) and/or the monomer of formula (4).

In addition to the polymers obtained from the monomers of formula (1) wherein $R_{11}$ to $R_{14}$ are alkyl, polymers obtained from the monomers of formula (1) wherein $R_{11}$ to $R_{14}$ are hydrogen are also preferred. In these monomers, it is preferred that at least one of $R_{11}$ and $R_{12}$ be alkyl and at least one of $R_{13}$ and $R_{14}$ be alkyl. Those monomers analogous to the monomers of formula (1) can be synthesized by the same procedure as the monomers of formula (1).

The compounds used in introducing ethylenically unsaturated reactive groups, preferably acrylic unsaturated reactive groups into the foregoing monomers at both ends thereof are not critical as long as they have ethylenically unsaturated reactive groups, preferably acrylic unsaturated reactive groups such as acryloyloxy, methacryloyloxy, acryloylamino, methacryloylamino, diacryloylamino, and dimethacryloylamino groups. Illustrative examples are given below:

methylaminoethyl acrylate, methylaminopropyl acrylate amide, methylaminoethyl methacrylate, methylaminoethyl methacrylate amide, methylaminopropyl methacrylate, methylaminopropyl methacrylate amide, methylaminobutyl methacrylate, methylaminopentyl methacrylate, methylaminohexane methacrylate, methylaminooctyl methacrylate, methylaminooctyl methacrylate amide, etc.

In the embodiment wherein treatment is carried out by physical means, the humidity sensitive thin film may also be formed of a polymer obtained from a monomer of the following formula (5) because it has the advantage that a more number of quaternary ammonium salts serving as conductivity-providing sites can be introduced, despite the drawback that some hysteresis is developed.

The monomer of formula (5) is described below.

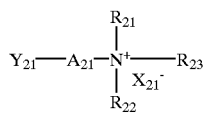

(5)

In formula (5), $A_{21}$ is a divalent group. $R_{21}$, $R_{22}$ and $R_{23}$ each are an alkyl group and they may be the same or different. $Y_{21}$ is a monovalent group terminated with an ethylenically unsaturated reactive group. $X_{21}^-$ is an anion.

The divalent group represented by $A_{21}$ is preferably an alkylene, alkenylene, arylene (e.g., phenylene), carbonyl or carbonyloxy group or a mixture thereof. These groups may have substituents, for example, alkyl groups such as methyl, and carbamoyl groups.

The alkylene groups preferably have 1 to 20 carbon atoms in total.

The alkenylene groups preferably have 2 to 10 carbon atoms in total.

The arylene groups preferably have 6 to 20 carbon atoms in total.

When the divalent group is a mixture of these groups, mixture preferably has 3 to 20 carbon atoms in total.

Illustrative, preferred examples of $A_{21}$ include $—(CH_2)_m—$ wherein m is an integer of 1 to 20, $—CH_2CH=CH—CH_2—$, $—CH(CH_3)—CH_2—CH_2—$, and $—C_6H_4—C_6H_4—$, with $—(CH_2)_m—$ wherein m is an integer of 1 to 20 being especially preferred.

The monovalent groups terminated with an ethylenically unsaturated reactive group represented by $Y_{21}$ are preferably vinyl and acrylic, especially acrylic, for example, groups having an acryloyloxy, methacryloyloxy, acryloylamino and methacryloylamino group, and preferably alkylene acrylate or methacrylate groups or alkylene acrylate or methacrylate amide groups.

The alkyl groups represented by $R_{21}$ to $R_{23}$ are generally unsubstituted ones, but may have substituents, and preferably contain 1 to 5 carbon atoms in total. Examples include methyl, ethyl, and propyl, with methyl being especially preferred. $R_{21}$ to $R_{23}$ are generally the same, but may be different from each other.

Any two or more of $R_{21}$ to $R_{23}$, $Y_{21}$, $A_{21}$ and portions thereof adjoining the N, taken together, may form a ring with the nitrogen (N) atom although it is preferred that they do not form a ring.

The anions represented by $X_{21}^-$ are preferably halide ions, for example, chloride, bromide and iodide ions. Chloride and bromide ions are preferred, and chloride ions are most preferred.

As indicated above, the monomer of formula (5) is preferably a monofunctional monomer having an acrylic unsaturated reactive group.

The monomer of formula (5) used herein is obtained as follows. Illustratively, the scheme of formula (5) is synthesized according to the following monomer.

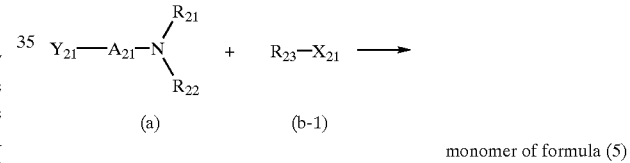

monomer of formula (5)

It is noted that $Y_{21}$, $A_{21}$, $R_{21}$ to $R_{23}$ in the above scheme are as defined for formula (5). Reference is made to the example in which $X_{21}$ is a halogen atom.

First, an acrylic amine compound (a) is reacted with a monohalogen compound (b-1) to form a monomer of formula (5) containing a quaternary ammonium salt and having an acrylic unsaturated group as one terminal group. In this stage, the amount of acrylic amine compound added may be substantially equimolar, especially 0.95 to 1 mole per mole of the monohalogen compound.

The reaction is carried out by stirring the reactants in an aprotic polar solvent such as acetonitrile or dioxane at about 50 to 70° C. for 96 hours. If the reactants are subject to reflux in an alcohol such as methanol, isopropanol, methoxyethanol or 2-ethoxyethanol as the solvent, ester interchange can occur, failing to produce the desired acrylic quaternary ammonium salt. Therefore, the alcoholic solvents which can trigger ester interchange reaction are not suitable.

At the end of reaction, acetone or the like is added to the reaction solution whereby the desired quaternary ammonium salt precipitates. The white precipitate thus obtained is filtered out. Acetone washing and drying yields the end compound.

The compounds used in introducing an ethylenically unsaturated reactive group, preferably acrylic unsaturated reactive group into the monomer of formula (5) at an end are not critical as long as they have ethylenically unsaturated reactive groups, preferably acrylic unsaturated reactive groups such as acryloyloxy, methacryloyloxy, acryloylamino, methacryloylamino, diacryloylamino, and dimethacryloylamino groups. The preferred compounds are dialkylaminoethyl acrylates or methacrylates and dialkylaminoethyl acrylate or methacrylate amides. Illustrative examples are given below:

dimethylaminoethyl acrylate,
dimethylaminopropyl acrylate amide,
dimethylaminoethyl methacrylate,
dimethylaminoethyl methacrylate amide,
dimethylaminopropyl methacrylate,
dimethylaminopropyl methacrylate amide,
dimethylaminobutyl methacrylate,
dimethylaminopentyl methacrylate,
dimethylaminohexane methacrylate,
dimethylaminooctyl methacrylate,
dimethylaminooctyl methacrylate amide, etc.

Examples of the monohalogen compounds to be reacted therewith include chloropropane, chlorobutane, chloropentane, chlorohexane, chlorooctane, chlorodecane, chlorododecane, bromopropane, dibromobutane, dibromopentane, bromohexane, bromooctane, bromodecane, and bromododecane.

The humidity sensitive thin film may be formed of a polymer of any one or more of the monomers of formulae (1) to (5) as well as the aforementioned polymers. More illustratively, depending on the desired device performance, a proper choice may be made among polymers of the backbone type and analogs or inversely, of the pendant type and analogs, and a proper choice may also be made for the number of carbon atoms in the backbone or pendant, the type of counter ion and other factors.

It is noted that in the embodiments of the invention involving treatment by physical means whereby satisfactory adhesion to the humidity sensitive thin film is achievable, the treatment may be combined with treatment with an acrylic monomer having an alkoxysilyl group (e.g., acrylic silane coupling agent), though not always necessary. In this case, the interdigital electrode-bearing substrate after the treatment may be coated with the acrylic monomer having an alkoxysilyl group before a humidity sensitive thin film is formed thereon. Alternatively, the acrylic monomer having an alkoxysilyl group is added to the coating solution of the humidity sensitive thin film-forming monomer.

In all the embodiments of the invention, a water repellent coating may be formed on the humidity sensitive thin film in order to preclude any influence of water droplets depositing thereon and to ensure rapid accurate humidity measurement. The water repellent coating should preferably have a contact angle with water of at least 90 degrees, and especially 90 to 130 degrees. To ensure sufficient penetration of moisture therethrough, the coating should desirably have a thickness of up to 5 μm, especially 0.1 to 2 μm. The preferred materials used to construct the water repellent coating are hydrophobic polymers, for example, fluoro-polymers such as polytetrafluoroethylene, olefinic polymers such as polyethylene and polypropylene, and silicone polymers. The method of forming the water repellent coating is not critical and the coating may be formed by dissolving any of the foregoing material in a suitable solvent (e.g., saturated carbon fluoride) and applying the solution.

As long as the humidity sensor device of the invention includes the above-mentioned humidity sensitive thin film on an insulating substrate having electrodes formed thereon, the remaining construction is not critical.

Referring to FIG. 1, there is illustrated one exemplary arrangement of the humidity sensor device. FIG. 1 is a plan view. As shown in FIG. 1, the humidity sensor device 1 includes a pair of interdigital electrodes 4 on an insulating substrate 2. The pair of interdigital electrodes 4 are disposed on the substrate 2 and interdigitated with each other to define a gap 5 of a certain distance therebetween. A humidity sensitive thin film 3 is formed over the insulating substrate 2 and interdigital electrodes 4. The interdigital electrodes 4 are provided at one end with electrode tabs 6 to which leads 7 are connected with solder welds 8. As seen from the figure, a resist film 9 is formed for preventing diffusion of the electrode material.

In this arrangement, preferably AC voltage is applied across the electrodes. Since the humidity sensitive thin film changes its electrical resistance or impedance in accordance with the humidity, the output voltage changes therewith, in terms of which the humidity is detectable. The applied voltage is typically up to about 12 volts.

Further referring to FIG. 1, the insulating substrate 2 and electrodes 4 used herein are as previously described. The electrode tabs 6 may be made of any conventional material which is compatible with the solder 8. For example, Ag—Pd alloy is printed in a conventional manner and baked at high temperatures to form the electrode tabs 6. Where Au is used as the electrodes 4, it is preferred that the resist film 9 of resist or glass is further provided, as shown in FIG. 1, in order to prevent diffusion of Au during soldering. No limits are imposed on the thickness and configuration of the resist film 9 as long as it is effective for preventing diffusion of Au during soldering.

The humidity sensor device of the present invention is not limited to the illustrated embodiment. Any desired shape or arrangement may be employed.

The gap between a pair of electrodes is typically about 100 to 500 μm.

EXAMPLE

Examples are given below together with Comparative Examples for illustrating the present invention.

Example 1

First, a monomer of formula (2) was synthesized.

In 20.2 g of methanol, 3.62 g (21.0 mmol) of N,N,N',N'-tetramethyl-1,12-dodecane diamine was reacted with 6.92 g (21.1 mmol) of 1,12-dibromododecane at 110° C. for 48 hours. Upon re-precipitation from acetone, 9.04 g of a white precipitate was obtained. Then, 6.92 g of the white precipitate was reacted with 3.54 g of dimethylaminopropyl methacrylamide in methanol at 90° C. for 24 hours. Upon reverse re-precipitation from acetone, 5.47 g of a pale yellow precipitate was obtained. It had a number average molecular weight of about 5,000.

Then, a monomer of formula (1) was synthesized.

In 21.04 g of acrylonitrile were dissolved 11.82 g (75.2 mmol) of dimethylaminoethyl methacrylate and 4.23 g (37.4 mmol) of 1,3-dichloropropane. After 0.27 g of 4-methoxyphenol was added as a polymerization inhibitor, reaction was effected at 60° C. for 120 hours. Upon re-prepcipitation from 1000 ml of acetone, 17.52 g of a quaternary salt was obtained. The yield was 90%.

The monomer of formula (2) and the monomer of formula (1) thus obtained were weighed in 0.5 g and 0.6 g, respectively, and 20.9 g of ethyl cellosolve was added thereto for dissolution. As a polymerization initiator, 0.2% by weight of KAYACURE ABQ (Nippon Kayaku Co., Ltd.) was added thereto, giving a solution of the humidity sensitive thin film-forming monomers (coating solution). The solution was held at 4° C. for storage.

Then a humidity sensor device as shown in FIG. 1 was fabricated. A porous ceramic substrate of alumina was used as the insulating substrate. Interdigital electrodes 4 were formed on the substrate by screen printing paste containing $RuO_2$ and glass frit and firing at high temperature. The gap between the electrodes 4 was about 225 μm.

The interdigital electrode-bearing substrate was submerged in 100 ml of isopropyl alcohol, immersed therein for cleaning for 10 minutes while applying ultrasonic waves, and allowed to stand for drying. This operation was repeated three cycles.

Immediately after drying, the humidity sensitive thin film-forming monomer solution was applied to the substrate by dispensing an aliquot of 2.75 μl per device. By holding at 25° C. for 15 minutes for drying, a coating was formed. Then the coating was exposed to UV radiation in a nitrogen atmosphere for one minute for polymerization, yielding a humidity sensitive thin film. At this point, the exposure of UV radiation was 1,000 $mJ/cm^2$. The humidity sensitive thin film had a thickness of about 5 μm.

The humidity sensor device thus fabricated was evaluated for output and examined by a water resistance test.

For evaluating the output, a divided flow humidity generating machine model SRH-1 (manufactured by Shinei K.K.) was used. The humidity sensor was incorporated in the circuit described and shown in JP-A 3-123843. The humidity sensor incorporated in the circuit was set in the humidity generating machine where the relative humidity was changed stepwise from a low level to a high level and then from the high level to the low level both at 25° C. During the humidity cycling process, the humidity sensor which was allowed to stand at a selected relative humidity for 30 minutes was measured for output voltage. The selected relative humidity levels were RH 5%, RH 10%, RH 20%, RH 30%, RH 40%, RH 50%, RH 60%, RH 70%, RH 80%, RH 90% and RH 95%. The results are plotted in FIG. 2.

Figure 3:
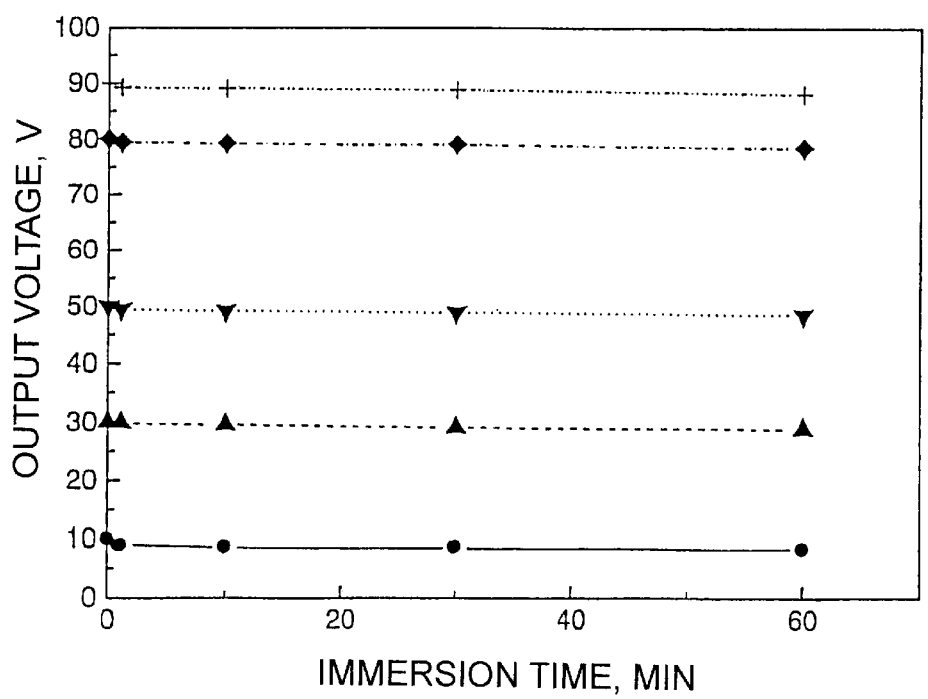
FIG. 3 is a graph showing the measured results of a water resistance test on the humidity sensor device of Example 1.

In the water resistance test, the humidity sensor having undergone output voltage monitoring as mentioned above was immersed in distilled water for 1 minute, dried in air, and measured for output voltage again. Subsequently, the time duration when the humidity sensor was immersed in distilled water was prolonged to 10 minutes, 30 minutes and 60 minutes whereupon the output voltage was similarly measured at relative humidity levels of RH 10%, RH 30%, RH 50%, RH 80% and RH 90% for comparison. The results are plotted in FIG. 3.

Figure 2:
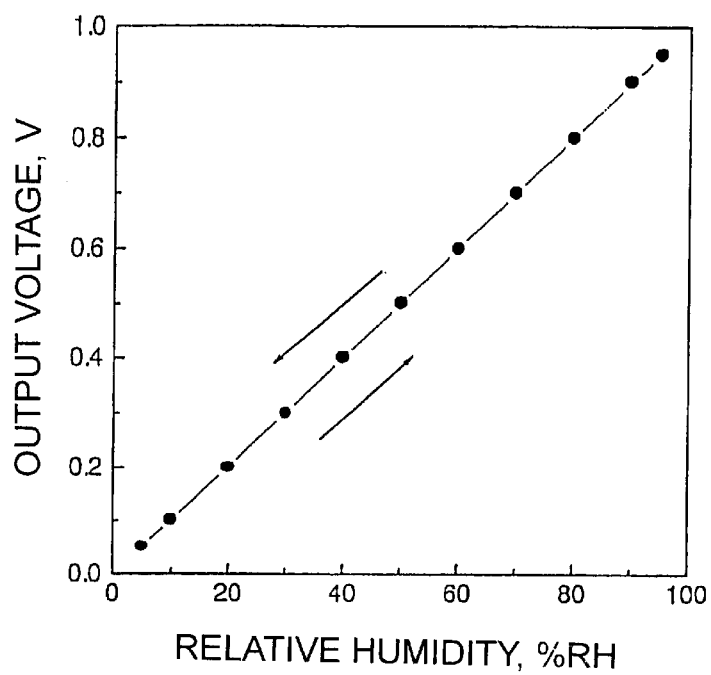
FIG. 2 is a graph showing the measured results of output of the humidity sensor device of Example 1.

It is evident from FIG. 2 that the inventive humidity sensor develops a good response curve without hysteresis. It is evident from FIG. 3 that the inventive humidity sensor is fully resistant to water.

Additionally, a gas resistance test was carried out. Gas resistance was tested by measuring outputs of the humidity sensor at different relative humidity levels, confirming a linear response thereof, then holding the sensor under conditions: temperature 40° C. and humidity RH 70 to 80% for 100 hours while flowing nitrogen dioxide gas, hydrogen chloride gas, ammonia gas, sulfur dioxide gas chlorine gas and hydrogen sulfide gas each in a concentration of 5 ppm, measuring again a humidity-representing output (HRH) of the humidity sensor at a preset relative humidity level (HRH), and determining a maximum change (HRH). The results are shown in Table 1.

TABLE 1

| | Maximum change of humidity (% RH) | | |
|---|---|---|---|
| Gas exposed | Example 1 | Example 3 | Comparative Example 2 |
| $Cl_2$ | −1.0 | −1.2 | −15.5 |
| $H_2S$ | −0.2 | −0.2 | −2.4 |
| $SO_2$ | −3.3 | −3.5 | −29.7 |
| $NO_2$ | −2.1 | −2.6 | −14.1 |
| HCl | −2.5 | −3.1 | −22.3 |
| $NH_3$ | −0.1 | 0.1 | 2.5 |

Minimal changes indicate that the inventive humidity sensor is fully resistant to gases.

The advantages of the present invention are thus demonstrated.

Example 2

An interdigital electrode-bearing alumina substrate which was prepared by the same procedure as in Example 1 was previously treated with an aqueous acetic acid solution of 1 wt % γ-methacryloxypropyltrimethoxysilane (KBM503 by Shin-Etsu Chemical Co., Ltd.), dried, and held at 120° C. for 20 minutes for thereby introducing acryloyl groups into the substrate surface. Thereafter, the substrate was dipped in the same humidity sensitive thin film-forming monomer solution as in Example 1, forming a coating. As in Example 1, UV radiation was irradiated to the coating for polymerization and crosslinking, obtaining a humidity sensor device.

The humidity sensor device thus fabricated was subjected to output evaluation and a water resistance test as in Example 1. The measured results of output are shown in FIG. 4, and the measured results of the water resistance test are shown in FIG. 5.

Figure 4:
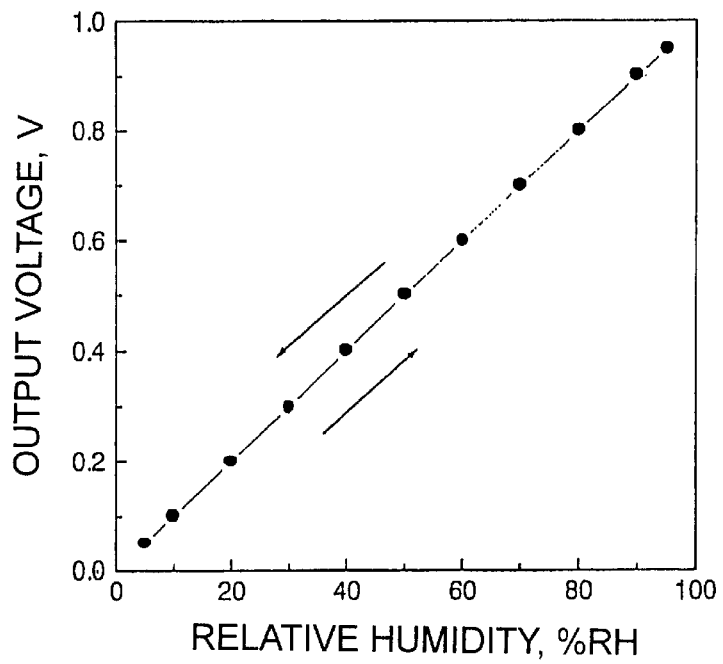
FIG. 4 is a graph showing the measured results of output of the humidity sensor device of Example 2.
Figure 5:
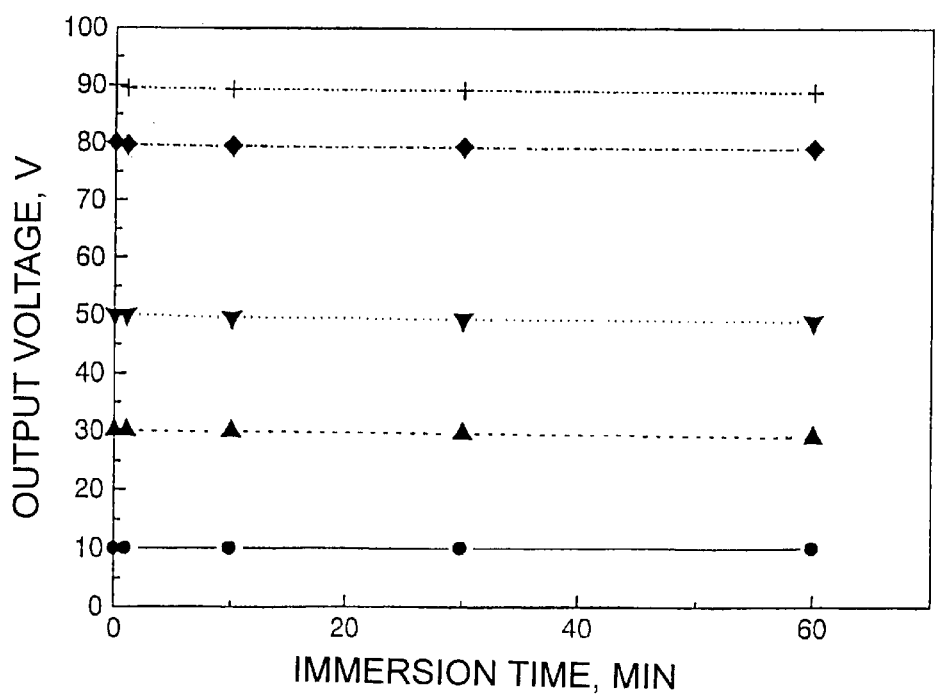
FIG. 5 is a graph showing the measured results of a water resistance test on the humidity sensor device of Example 2.

It is evident from FIGS. 4 and 5 that the inventive humidity sensor develops satisfactory humidity response performance and water resistance. The water resistance is improved over Example 1.

Also a gas resistance test was carried out as in Example 1, obtaining satisfactory results as in Example 1.

Example 3

First, a monomer of formula (2) was synthesized.

In 23 g of methanol were dissolved 6.30 g (36.6 mmol) of N,N,N',N'-tetramethyl-1,12-dodecane diamine and 9.62 g (40.2 mmol) of 1,12-dichlorododecane. The solution was refluxed in an eggplant-shaped flask. The oil bath temperature was 110° C. at this point. It was observed after 36 hours of reaction that the solution turned white turbid. After 48 hours, the reaction was stopped, and 40 ml of methanol was added to the white turbid viscous solution. Though no insolubles were present, the solution was once filtered, followed by reverse re-precipitation, obtaining a white precipitate. The amount of acetone used was 500 ml. The dry weight was 6.04 g. Subsequently, 5.07 g of the white precipitate was dissolved in 9 g of methanol. Dimethylaminopropylmethacrylamide, 2.98 g, was added to the solution and reaction was effected at an oil bath temperature of 90° C. for 24 hours. The solution was in a dark orange viscous state. Methanol, 20 ml, was added to the solution, followed by reverse re-precipitation, obtaining a pale yellow precipitate. The yield was 2.47 g. An analysis by gel permeation chromatography (GPC) showed a number average molecular weight (Mn) of 2734.

Then, a monomer of formula (1) was synthesized.

In 20 ml of acrylonitrile were dissolved 9.63 g (67.2 mmol) of 2-dimethylaminoethyl acrylate and 3.79 g (33.6 mmol) of 1,3-dichloropropane. To the solution was added 0.35 g of 4-methoxyphenol. In an eggplant-shaped flask, the solution was stirred at 60° C. for 5 days (precisely, 128 hours) by means of a magnetic stirrer. It was observed that the solution remained unchanged after 3 days, but a white precipitate settled out on the fifth day. The quaternary salt was completely precipitated out. After the termination of reaction, 50 ml of methanol was added thereto for dissolving the white precipitate. Since 0.112 g of insolubles (weighed after drying) was present at this point, the solution was once filtered. By adding 500 ml of acetone to the filtrate to effect reverse re-precipitation, the quaternary salt was completely precipitated out. The quaternary salt was separated and dried in vacuum, obtaining the end product. The yield was 5.131 g.

The monomer of formula (2) and the monomer of formula (1) thus obtained were weighed in 0.3 g and 0.6 g, respectively, and dissolved in 18 ml of water to prepare an aqueous solution of about 5% by weight. To the aqueous solution, 0.2% by weight of KAYACURE ABQ (Nippon Kayaku Co., Ltd., benzophenone compound) was added as a polymerization initiator, giving a coating solution (humidity sensitive thin film-forming monomer solution).

Using the coating solution, a humidity sensor device 1 as shown in FIG. 1 was fabricated. A porous ceramic substrate of alumina was used as the insulating substrate 2. Interdigital electrodes 4 were formed on the substrate by screen printing paste containing $RuO_2$ and glass frit and firing at high temperature. The gap between the electrodes 4 was about 225 μm.

The coating solution was coated onto the insulating substrate 2 by dipping and dried at 50° C. for 5 minutes, forming a coating. Then the coating on the electrode side was exposed to UV radiation in a nitrogen atmosphere for one minute for crosslinking, yielding a humidity sensitive thin film 3. At this point, the exposure of UV radiation was 1,000 mJ/cm$^2$. The humidity sensitive thin film 3 had a thickness of about 5 μm. The humidity sensor device thus fabricated was subjected to output evaluation and a water resistance test as in Example 1. The measured results of output are shown in FIG. 6, and the measured results of the water resistance test are shown in FIG. 7.

Figure 6:
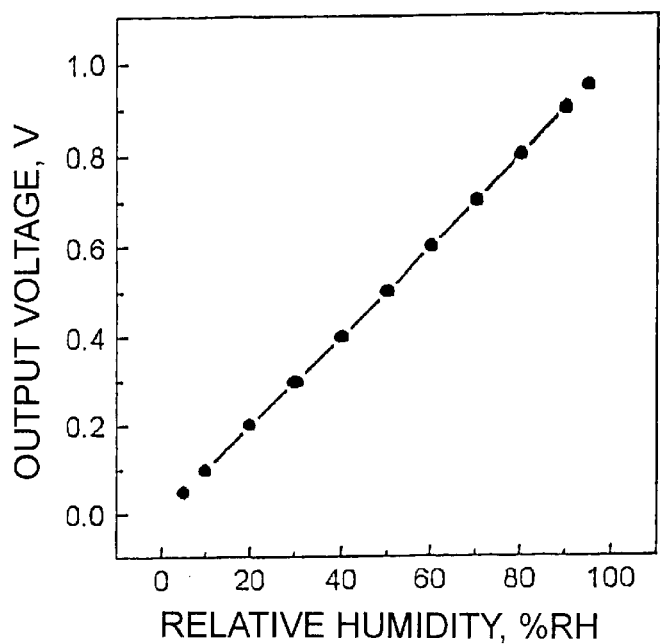
FIG. 6 is a graph showing the measured results of output of the humidity sensor device of Example 3.
Figure 7:
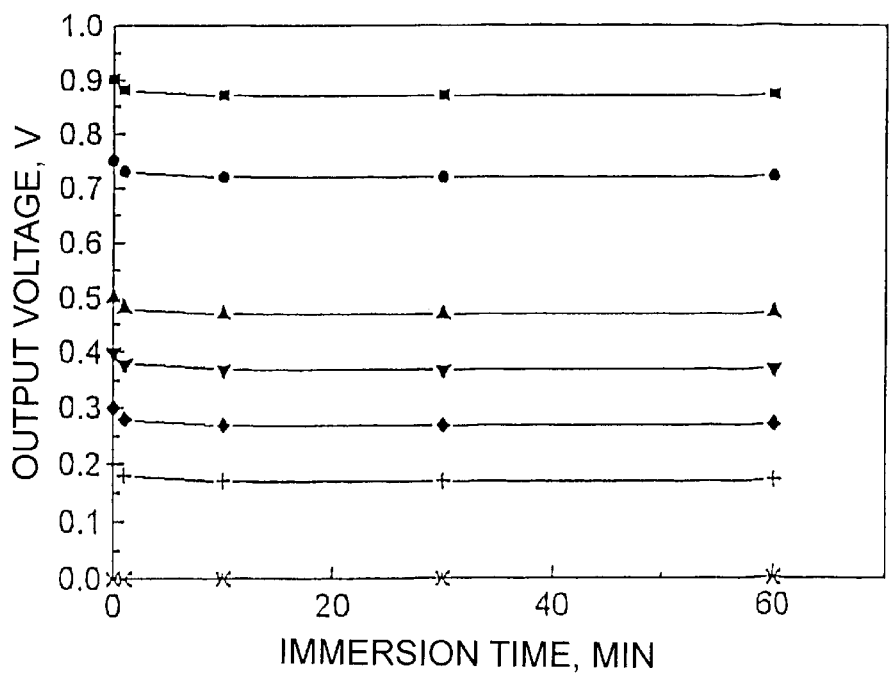
FIG. 7 is a graph showing the measured results of a water resistance test on the humidity sensor device of Example 3.

It is evident from FIG. 6 that the inventive humidity sensor develops a good response curve without hysteresis. It is evident from FIG. 7 that the inventive humidity sensor is fully resistant to water.

Also a gas resistance test was carried out as in Example 1, with the results shown in Table 1 together with the results of Example 1. The gas resistance was found satisfactory.

Example 4

An interdigital electrode-bearing alumina substrate which was prepared by the same procedure as in Example 3 was previously treated with an aqueous acetic acid solution of 1 wt % γ-methacryloxypropyltrimethoxysilane (KBM503 by Shin-Etsu Chemical Co., Ltd.), dried, and held at 120° C. for 20 minutes for thereby introducing acryloyl groups into the substrate surface. Thereafter, the substrate was dipped in the same humidity sensitive thin film-forming monomer solution as in Example 3 forming a coating. As in Example 3, UV radiation was irradiated to the coating for polymerization and crosslinking, obtaining a humidity sensor device.

The humidity sensor device thus fabricated was subjected to output evaluation and a water resistance test as in Example 1. The measured results of output are shown in FIG. 8, and the measured results of the water resistance test are shown in FIG. 9.

Figure 8:
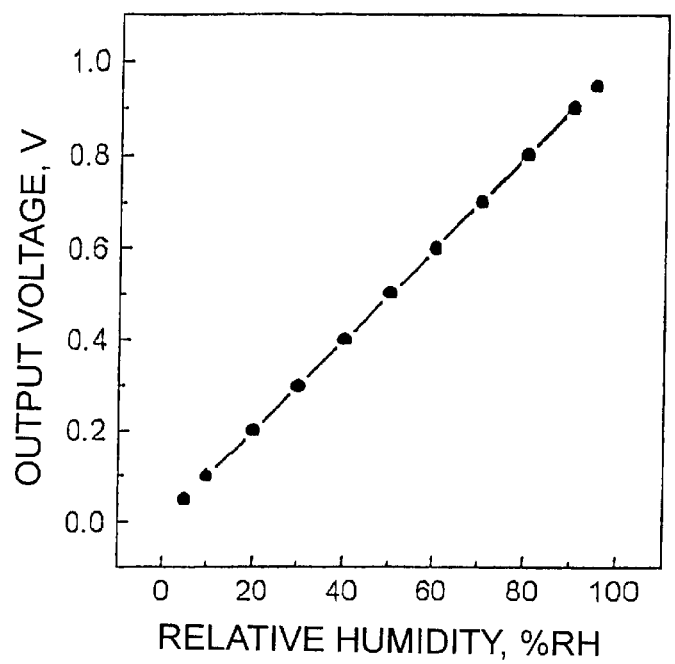
FIG. 8 is a graph showing the measured results of output of the humidity sensor device of Example 4.
Figure 9:
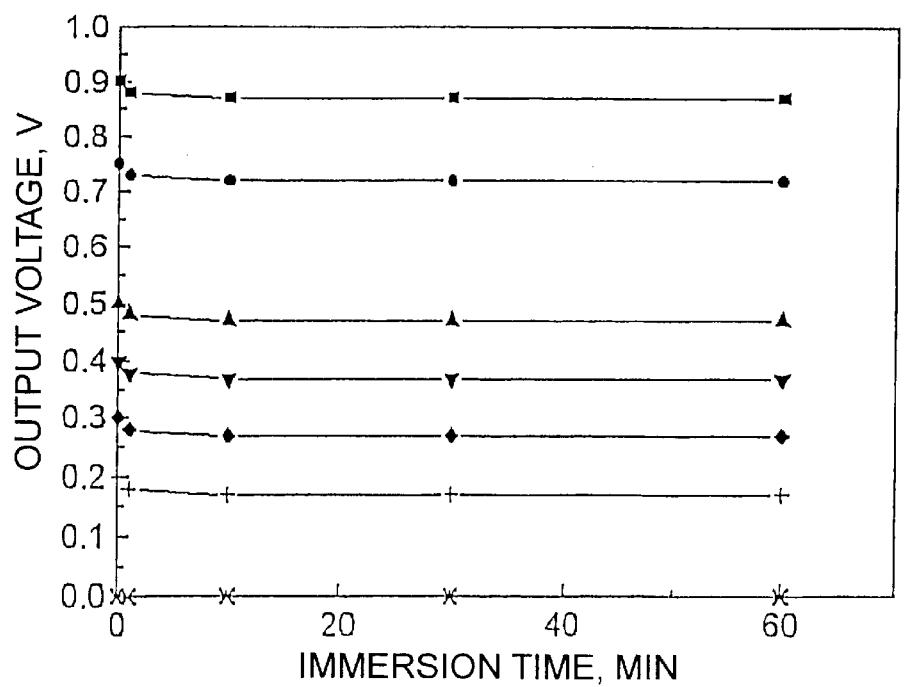
FIG. 9 is a graph showing the measured results of a water resistance test on the humidity sensor device of Example 4.

It is evident from FIGS. 8 and 9 that the inventive humidity sensor develops satisfactory humidity response performance and water resistance. The water resistance is improved over Example 3.

Also a gas resistance test was carried out as in Example 1, obtaining satisfactory results as in Example 3.

Example 5

A monomer of formula (1) was synthesized by the same procedure as in Example 3 using 5.04 g (25.6 mmol) of N,N,N',N'-tetramethyl-1,12-dodecane diamine and 9.91 g (30.2 mmol) of 1,12-dibromododecane as the starting reactants.

A monomer of formula (2) was synthesized by the same procedure as in Example 1 using 9.88 g (66.9 mmol) of 2-dimethylaminoethyl methacrylate and 3.68 g (33.3 mmol) of 1,3-dichloropropane as the starting reactants.

The monomer of formula (2) and the monomer of formula (1) thus obtained were weighed in 0.1 g and 0.5 g, respectively, and dissolved in 12 ml of water to prepare an aqueous solution of about 5% by weight. A humidity sensor device was fabricated by the same procedure as in Example 1.

The humidity sensor device thus fabricated was subjected to output evaluation and a water resistance test as in Example 1. The measured results of output are shown in FIG. 10, and the measured results of the water resistance test are shown in FIG. 11.

Figure 10:
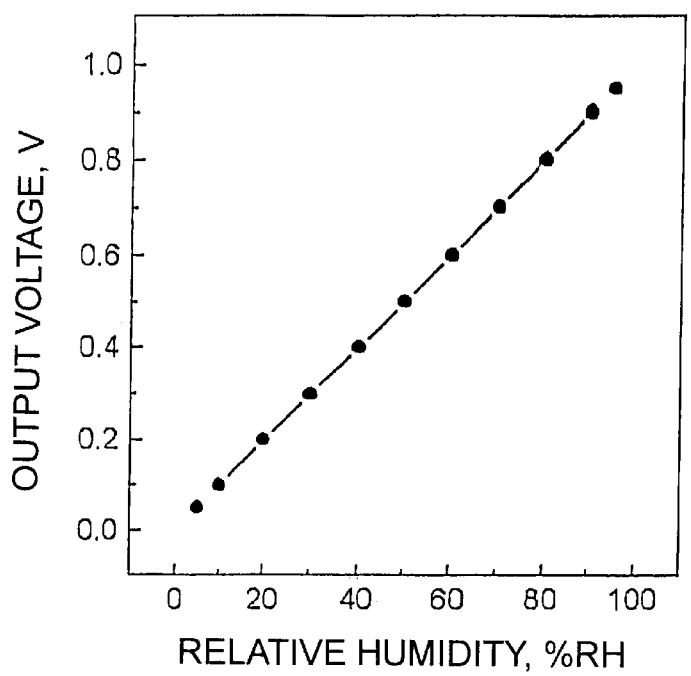
FIG. 10 is a graph showing the measured results of output of the humidity sensor device of Example 5.
Figure 11:
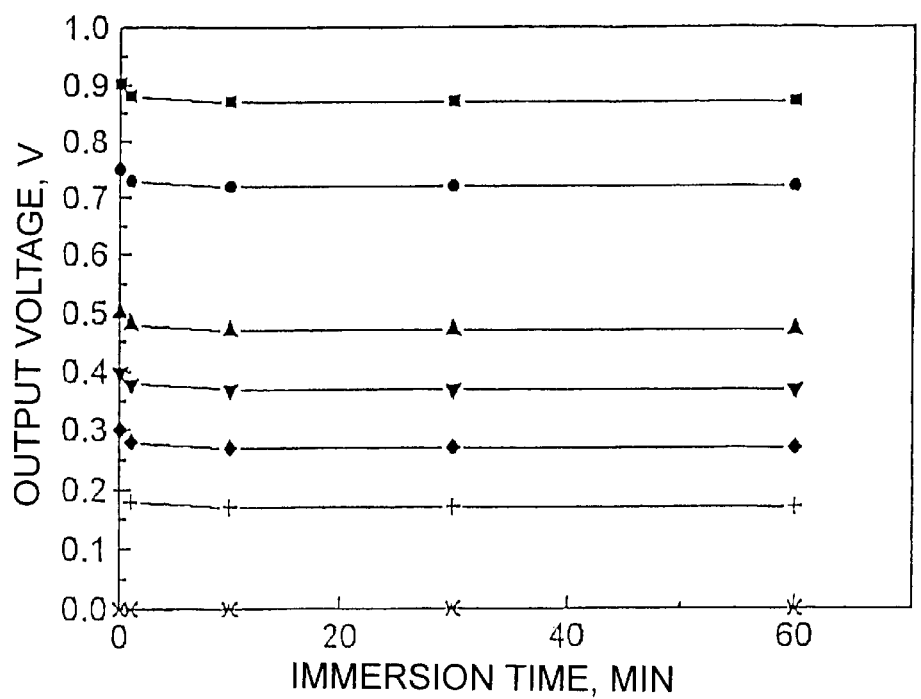
FIG. 11 is a graph showing the measured results of a water resistance test on the humidity sensor device of Example 5.

It is evident from FIGS. 10 and 11 that the inventive humidity sensor develops satisfactory humidity response performance and water resistance.

Also a gas resistance test was carried out as in Example 1, obtaining satisfactory results as in Example 3.

Comparative Example 1

Humidity sensor devices were fabricated as in Example 3 aside from using the monomer of formula (2) and the monomer of formula (1) separately. The measured results of output from the device using the monomer of formula (1) are shown in FIG. 12, and the measured results of a water resistance test from the device using the monomer of formula (2) are shown in FIG. 13.

Figure 12:
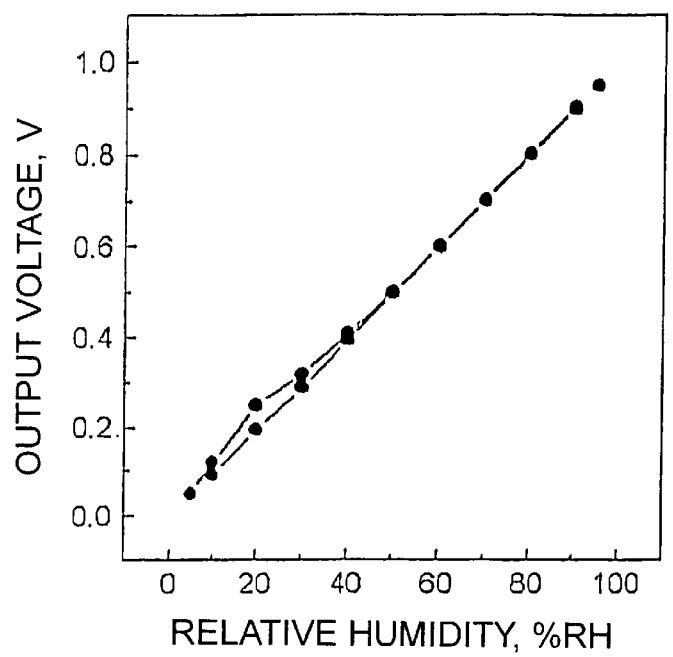
FIG. 12 is a graph showing the measured results of output of the humidity sensor device of Comparative Example 1.
Figure 13:
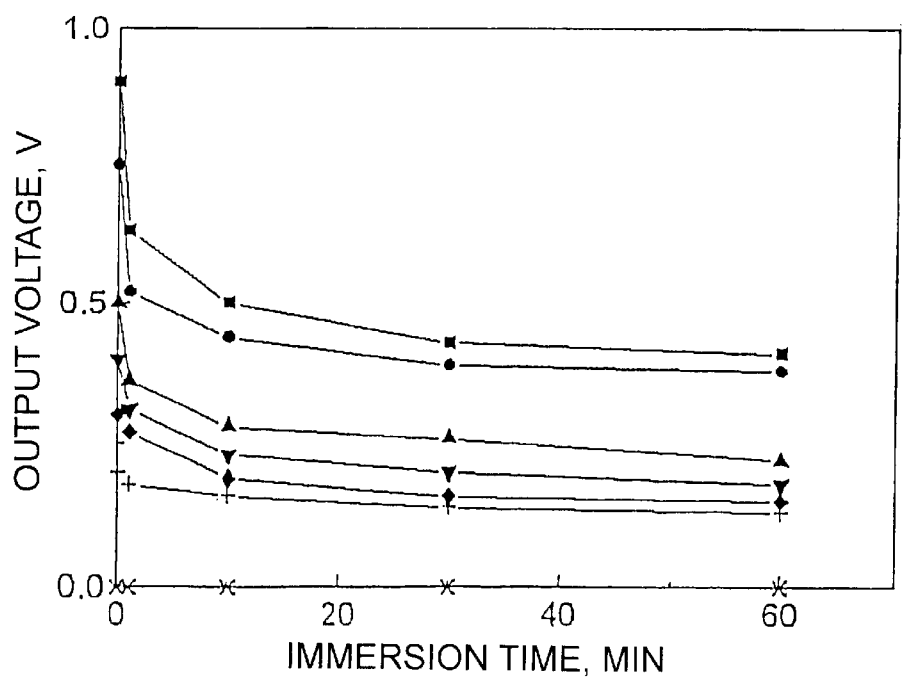
FIG. 13 is a graph showing the measured results of a water resistance test on the humidity sensor device of Comparative Example 1.

With respect to the humidity response performance, the device using the monomer of formula (2) developed substantially equivalent performance to Example 3, but the device using the monomer of formula (1) produced low outputs over the entire range, with hysteresis observed in the low-humidity region as shown in FIG. 12. Both the devices were satisfactory in the gas resistance test. In the water resistance test, however, the device using the monomer of formula (2) produced somewhat reduced outputs as shown in FIG. 13, and the device using the monomer of formula (1) was poorly resistant to water.

Comparative Example 2

A humidity sensor device was fabricated as in Example 3 except that on an alumina substrate on which interdigital electrodes were formed as in Example 3, a humidity sensitive thin film of 0.1 μm thick was formed by applying and crosslinking a copolymer (number average molecular weight 110,000) in the form of an ionene polymer having an acrylamide group introduced at either end which was obtained by reacting 8.6 g of N,N,N',N'-tetramethyldiaminohexane with 6.8 g of 1,3-dichloropropane as described in JP-A 7-318526.

The device was evaluated as in Example 1, finding nearly satisfactory results with respect to the humidity response performance and water resistance. The results of a gas resistance test are shown in Table 1 together with the results of Examples 1 and 3, indicating poor gas resistance.

Comparative Example 3

A humidity sensor device was fabricated as in Example 3 except that 0.015 g of divinyl benzene was used instead of the monomer of formula (1). The device was similarly evaluated. No problems were found with respect to the water resistance and gas resistance. The device produced low outputs because of an increased impedance.

Example 6

Four humidity sensor devices were fabricated as in Examples 1 to 4 except that during the synthesis of the monomer of formula (1), 1,6-dichlorohexane or 1,10-dichlorodecane was used instead of 1,3-dichloropropane. The devices were similarly evaluated. In accordance with the device construction of Examples 1 to 4, all the devices produced satisfactory results as in Examples 1 to 4.

Example 7

Four humidity sensor devices were fabricated as in Examples 3 and 4 except that during the synthesis of the monomer of formula (2), a combination of N,N,N',N'-tetramethyl-1,6-hexane diamine with 1,3-dichloropropane or a combination of N,N,N',N'-tetramethyl-1,6-hexane diamine with 1,12-dichlorododecane was employed. The devices were similarly evaluated. In accordance with the device construction of Examples 3 and 4, all the devices produced satisfactory results as in Examples 3 and 4.

Example 8

Using the monomer of formula (2) obtained from 6.30 g (36.6 mmol) of N,N,N',N'-tetramethyl-1,12-dodecane diamine and 9.62 g (40.2 mmol) of 1,12-dichlorododecane and the monomer of formula (1) obtained from 9.63 g (67.2 mmol) of 2-dimethylaminoethyl acrylate and 3.79 g (33.6 mmol) of 1,3-dichloropropane, 10 ml of a humidity sensitive thin film-forming monomer solution (coating solution) having the same compositional ratio as in Example 3 was prepared.

Next, a humidity sensor device 1 as shown in FIG. 1 was fabricated. A porous ceramic substrate of alumina was used as the insulating substrate 2. Interdigital electrodes 4 were formed on the substrate by screen printing paste containing $RuO_2$ and glass frit and firing at high temperature. The gap between the electrodes 4 was about 225 μm.

The interdigital electrode-bearing substrate was placed in 100 ml of isopropyl alcohol, immersed therein for 10 minutes for cleaning, and allowed to stand for drying.

A plasma treatment was carried out using a plasma dry cleaner model PDC200 by Yamato Science Co., Ltd. After 100 samples to be treated were placed, the chamber was evacuated to vacuum by operating a vacuum pump EC-403 by ULVAC Co. for 10 minutes. Oxygen gas was fed to the chamber at a flow rate of 300 sccm (0.51 Pa·m$^3$·s$^{-1}$) while a vacuum of 55 Pa was maintained. A plasma was generated at an RF power of 200 W, with which the samples were treated for one minute. The distance between electrodes was 10 cm.

Immediately after the treatment, a humidity sensitive thin film was formed as in Example 3.

The humidity sensor device thus fabricated was subjected to output evaluation and a water resistance test as in Example 1.

Figure 14:
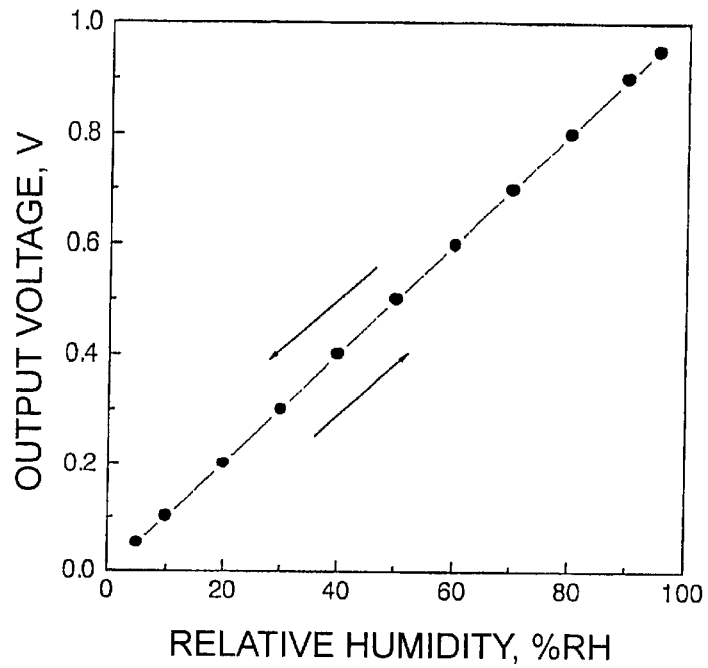
FIG. 14 is a graph showing the measured results of output of the humidity sensor device of Example 8.
Figure 15:
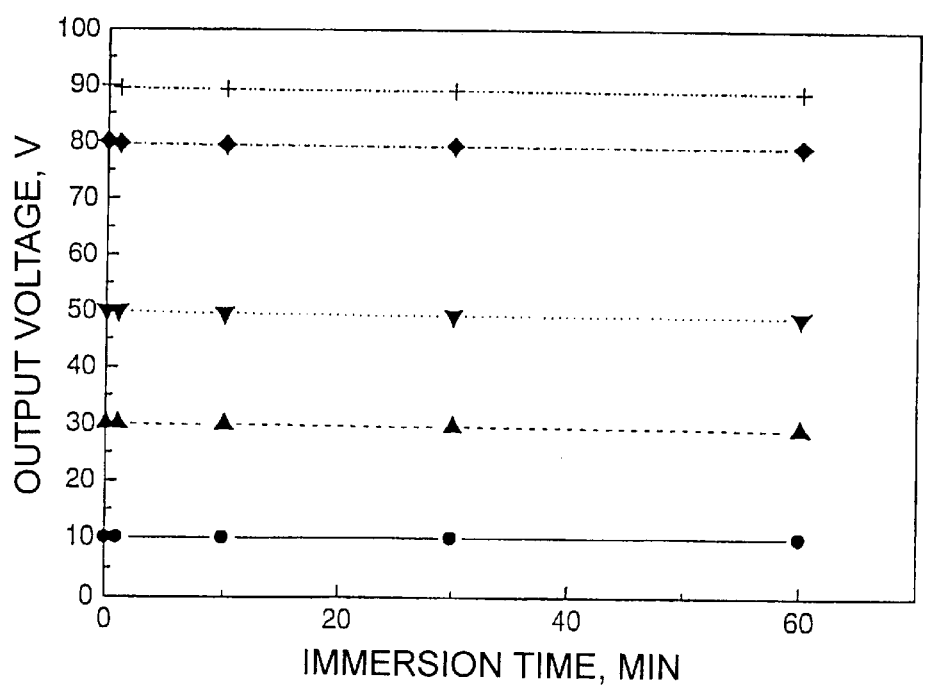
FIG. 15 is a graph showing the measured results of a water resistance test on the humidity sensor device of Example 8.

The measured results of output are shown in FIG. 14, and the measured results of the water resistance test are shown in FIG. 15.

It is evident from FIG. 14 that the inventive humidity sensor develops a good response curve without hysteresis. It is evident from FIG. 15 that the inventive humidity sensor is fully resistant to water. Also a gas resistance test was carried out as in Example 1, obtaining satisfactory results as in Example 3.

Example 9

A humidity sensor device was fabricated as in Example 8 except that the interdigital electrode-bearing substrate was plasma treated under atmospheric pressure. The device was similarly evaluated for performance, obtaining likewise satisfactory results.

The plasma treatment in this Example used an atmospheric pressure plasma cleaning apparatus by Matsushita Electric Machine & Vision Co., Ltd. Treatment was carried out by applying an oxygen plasma at a power of 700 W, an irradiation distance of 5 mm, and a head moving speed of 10 mm/sec and then a hydrogen plasma under the same conditions.

Example 10

In 10 ml of acetonitrile were dissolved 4.73 g (0.030 mol) of dimethylaminoethyl acrylate and 2.3 g (0.0148 mol) of 1,6-dichlorohexane. The solution was stirred below 50° C. for 80 hours, effecting quaternization reaction according to the scheme shown below. Some white precipitate formed, and 30 ml of acetone was further added for completely precipitating out the quaternary salt. The white precipitate was filtered, washed with acetone and dried at 80° C. for one hour. There was obtained 2.77 g (yield 39.6%) of the quaternary salt. 0.47 g (0.001 mol) of the quaternary salt and 0.025 g (0.0001 mol) of γ-methacryloxypropyltrimethoxysilane (KBM503 by Shin-Etsu Chemical Co., Ltd.) were dissolved in 10 ml of water to prepared an aqueous solution of about 5% by weight. To the aqueous solution, 0.2% by weight of KAYACURE ABQ (Nippon Kayaku Co., Ltd.) was added as a polymerization initiator, giving a coating solution.

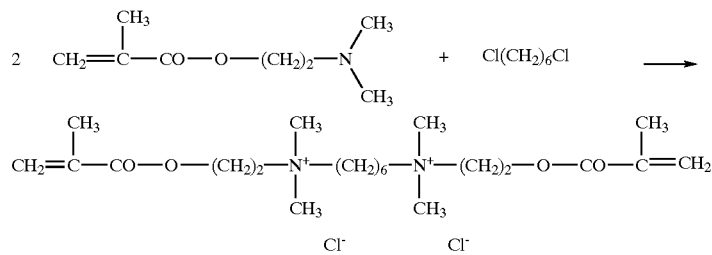

Using the coating solution, a humidity sensor device 1 as shown in FIG. 1 was fabricated. A porous ceramic substrate of alumina was used as the insulating substrate 2. Interdigital electrodes 4 were formed on the substrate by screen printing paste containing $RuO_2$ and glass frit and firing at high temperature. The gap between the electrodes 4 was about 225 μm.

The coating solution was coated onto the insulating substrate 2 by dipping and dried at 50° C. for 5 minutes, forming a coating. Then the coating both on the electrode side and the back side was exposed to UV radiation in a nitrogen atmosphere for one minute on each side for crosslinking, yielding a humidity sensitive thin film 3. At this point, the exposure of UV radiation was 1,000 $mJ/cm^2$. The humidity sensitive thin film 3 had a thickness of 8 μm.

The thus obtained film was treated for 2 hours in an atmosphere of 60° C. and RH 80% for causing hydroxyl groups on the substrate and electrode surface to react with alkoxysilyl or silanol groups. The humidity sensor device thus fabricated was evaluated for output and examined by a water resistance test.

For evaluating the output, a divided flow humidity generating machine model SRH-1 (manufactured by Shinei K.K.) was used. The humidity sensor was incorporated in the circuit described and shown in JP-A 3-123843. The humidity sensor incorporated in the circuit was set in the humidity generating machine where the relative humidity was changed stepwise from a low level to a high level and then from the high level to the low level both at 25° C. During the humidity cycling process, the humidity sensor which was allowed to stand at a selected relative humidity for 10 minutes was measured for output voltage. The selected relative humidity levels were RH 0%, RH 10%, RH 20%, RH 30%, RH 50%, RH 70% and RH 90%. The results are plotted in FIG. 16.

In the water resistance test, the humidity sensor having undergone output voltage monitoring as mentioned above was immersed in distilled water for 1 minute, dried in air, and measured for output voltage again for comparison. Subsequently, the time duration when the humidity sensor was immersed in distilled water was prolonged to 10 minutes, 30 minutes and 60 minutes whereupon the output voltage was similarly measured for comparison. The results are plotted in FIG. 17.

Figure 16:
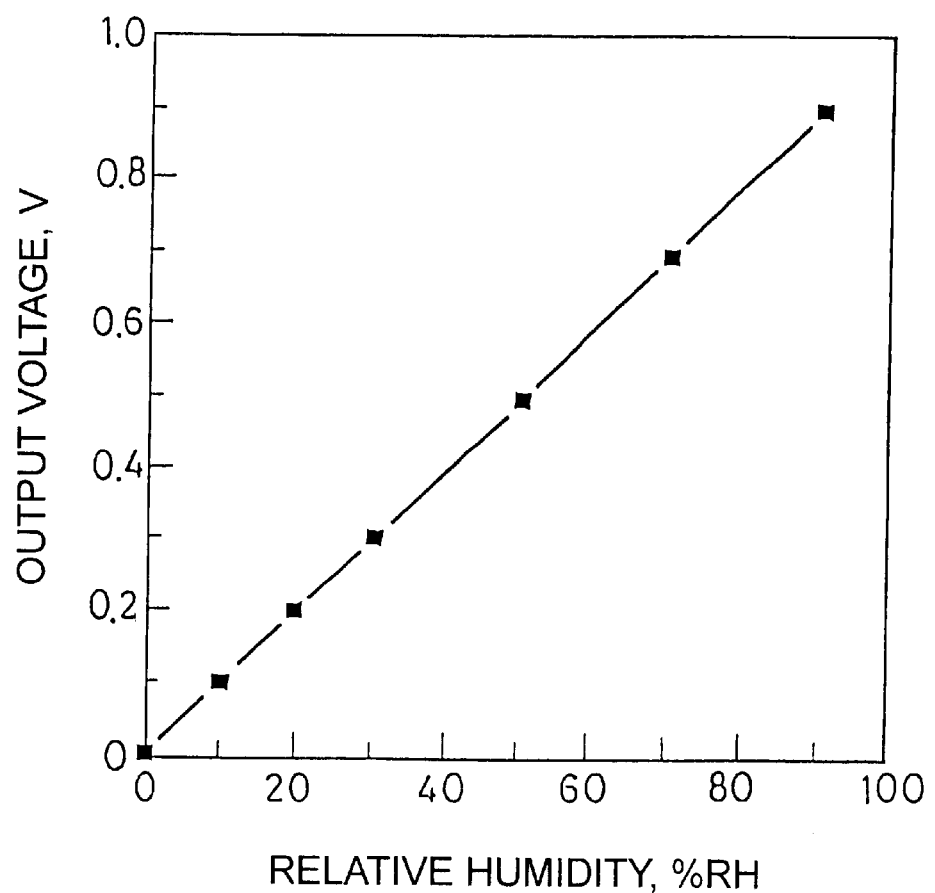
FIG. 16 is a graph showing the measured results of output of the humidity sensor device of Example 10.

It is evident from FIG. 16 that the inventive humidity sensor develops no hysteresis and can measure a low humidity, especially in the region of not higher than RH 10%.

Figure 17:
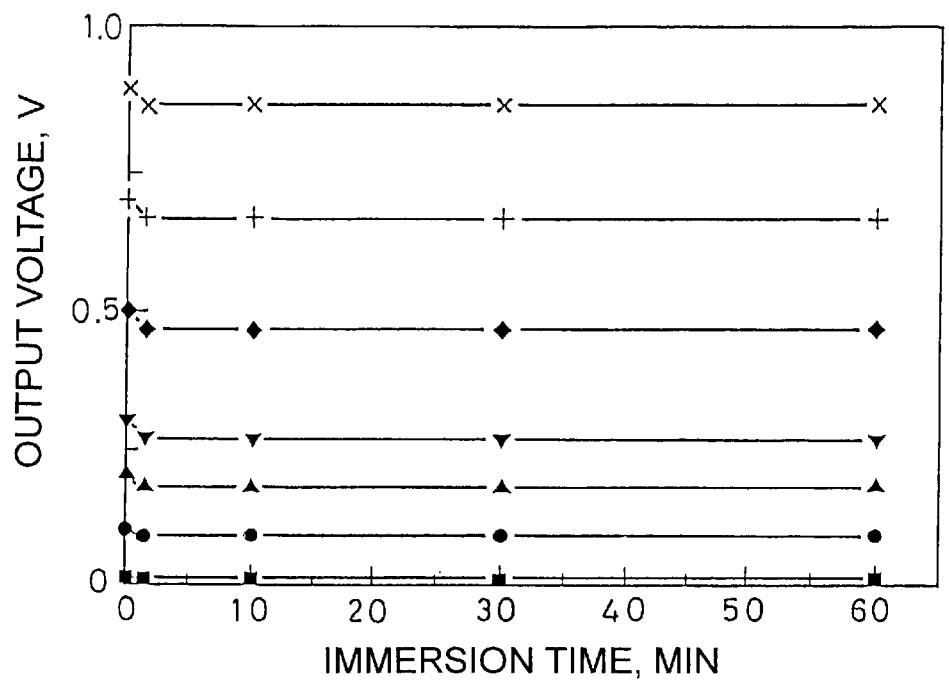
FIG. 17 is a graph showing the measured results of a water resistance test on the humidity sensor device of Example 10.

It is evident from FIG. 17 that the inventive humidity sensor is fully resistant to water.

Additionally, a gas resistance test was carried out. Gas resistance was tested by measuring outputs of the humidity sensor at different relative humidity levels, confirming a linear response thereof, then holding the sensor under conditions: temperature 40° C. and humidity RH 70 to 80% for 100 hours while flowing nitrogen dioxide gas, hydrogen chloride gas, ammonia gas, sulfur dioxide gas, chlorine gas and hydrogen sulfide gas each in a concentration of 5 ppm, measuring again a humidity representing output (HRH) of the humidity sensor at a preset relative humidity level (HRH), and determining a maximum change (HRH). The results are shown in Table 2 together with the results of Comparative Example 2.

TABLE 2

| | Maximum change of humidity (% RH) | |
|---|---|---|
| Gas exposed | Example 10 | Comparative Example 2 |
| $Cl_2$ | −1.2 | −15.5 |
| $H_2S$ | −0.4 | −2.4 |
| $SO_2$ | −4.8 | −29.7 |
| $NO_2$ | −3.8 | −14.1 |
| HCl | −3 | −22.3 |
| $NH_3$ | 0.2 | 2.5 |

Minimal changes indicate that the inventive humidity sensor is fully resistant to gases.

The advantages of the present invention are thus demonstrated.

Example 11

An interdigital electrode-bearing alumina substrate which was prepared by the same procedure as in Example 10 was previously treated with an aqueous acetic acid solution of 1 wt % γ-methacryloxypropyltrimethoxysilane (KBM503) for introducing acryloyl groups into the substrate surface. After a solution was prepared by dissolving the quaternary salt obtained in Example 1 in water to form a 5 wt % aqueous solution and adding a polymerization initiator thereto, the substrate was dipped in the solution, forming a coating.

As in Example 10, UV radiation was irradiated to the coating for polymerization and crosslinking, obtaining a humidity sensor device.

The humidity sensor device thus fabricated was subjected to output evaluation and a water resistance test as in Example 10. The measured results of output are shown in FIG. 18, and the measured results of the water resistance test are shown in FIG. 19.

Figure 18:
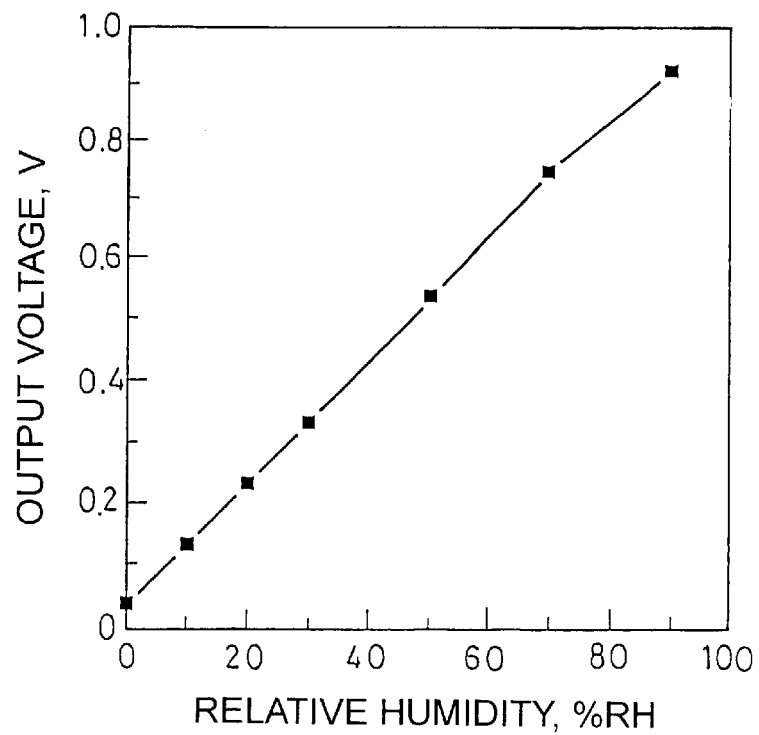
FIG. 18 is a graph showing the measured results of output of the humidity sensor device of Example 11.
Figure 19:
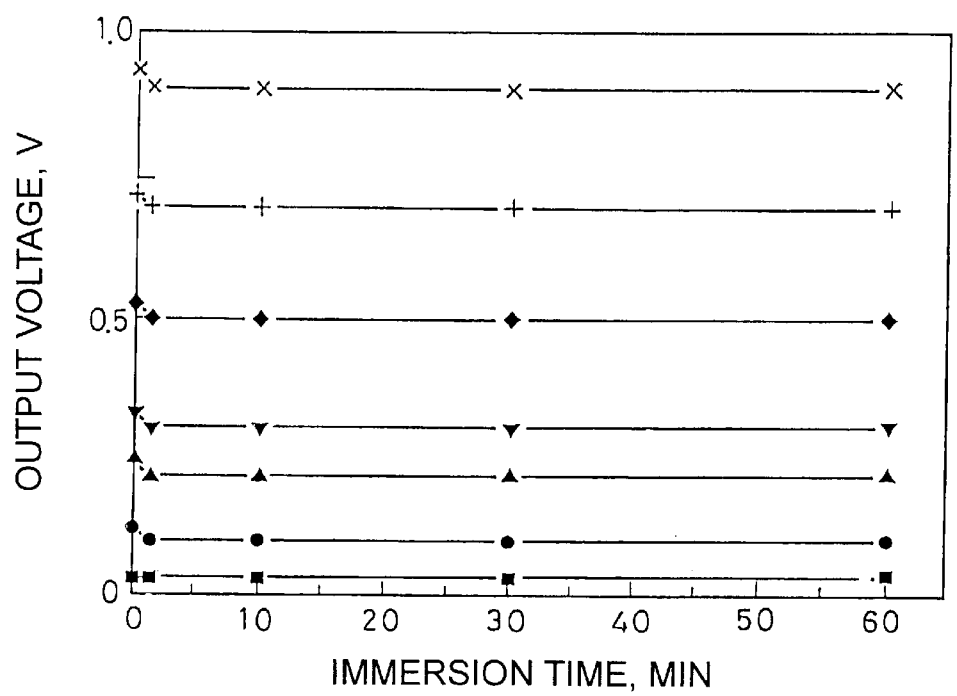
FIG. 19 is a graph showing the measured results of a water resistance test on the humidity sensor device of Example 11.

It is evident from FIGS. 18 and 19 that the inventive humidity sensor develops satisfactory humidity response performance and water resistance.

Also a gas resistance test was carried out as in Example 10, obtaining satisfactory results as in Example 10.

Comparative Example 4

A device was fabricated as in Example 10 except that the silane coupling agent was omitted.

Figure 20:
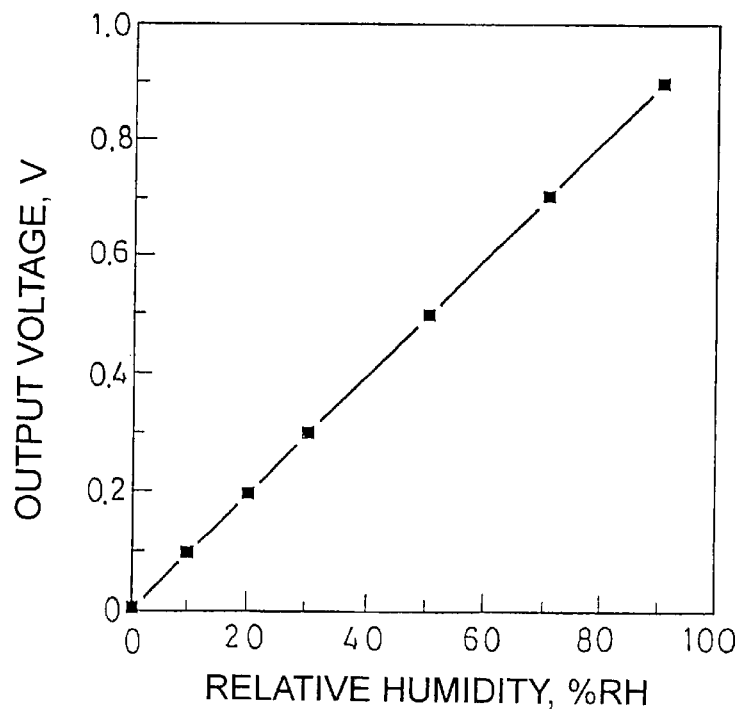
FIG. 20 is a graph showing the measured results of output of the humidity sensor device of Comparative Example 4.

The humidity response performance was substantially equivalent as shown in FIG. 20. No problem was found with respect to the gas resistance test. In the water resistance test, however, the humidity sensitive thin film immediately peeled as a whole, and outputs were no longer produced.

Example 12

In 14.8 g of acetonitrile were dissolved 14.21 g (90.4 mmol) of dimethylaminoethyl methacrylate and 5.11 g (45.2 mmol) of 1,3-dichloropropane. As a polymerization inhibitor, 0.35 g of 4-methoxyphenol was added. The solution was stirred at 60° C. for 96 hours, effecting quaternization reaction of the same type as in Example 10. A white precipitate formed, and 20 ml of methanol was added thereto to dissolve the precipitate. Once the solution was filtered, re-precipitation from 1000 ml of acetone was effected, causing the quaternary salt to precipitate. The white precipitate was filtered, washed with 30 ml of acetone, and dried at 40° C. for one hour and then in vacuum. There was obtained 17.52 g of the quaternary salt. The yield was 90%.

Next, a humidity sensor device as shown in FIG. 1 was fabricated. A porous ceramic substrate of alumina was used as the insulating substrate. Interdigital electrodes 4 were formed on the substrate by screen printing paste containing $RuO_2$ and glass frit and firing at high temperature. The gap between the electrodes 4 was about 225 μm.

The interdigital electrode-bearing substrate was placed in 100 ml of isopropyl alcohol, immersed therein for 10 minutes for cleaning, and allowed to stand for drying.

A plasma treatment was carried out using a plasma dry cleaner model PDC200 by Yamato Science Co., Ltd. After 100 samples to be treated were placed, the chamber was evacuated to vacuum by operating a vacuum pump EC-403 by ULVAC Co. for 10 minutes. Oxygen gas was fed to the chamber at a flow rate of 300 sccm (0.51 $Pa \cdot m^3 \cdot s^{-1}$) while a vacuum of 55 Pa was maintained. A plasma was generated at an RP power of 700 W, with which the samples were treated for one minute. The distance between electrodes was 10 cm.

Immediately after the treatment, the humidity sensitive thin film-forming monomer solution was applied to the substrate by dispensing an aliquot of 2.2 μl per device. By holding at 25° C. for 15 minutes for drying, a coating was formed. Then the coating was exposed to UV radiation in a nitrogen atmosphere for one minute for polymerization, yielding a humidity sensitive thin film. At this point, the exposure of UV radiation was 1,000 $mJ/cm^2$. The humidity sensitive thin film had a thickness of about 4 μm.

The humidity sensor device thus fabricated was evaluated for output and examined by a water resistance test.

For evaluating the output, a divided flow humidity generating machine model SRH-1 (manufactured by Shinei K.K.) was used. The humidity sensor was incorporated in the circuit described and shown in JP-A 3-123843. The humidity sensor incorporated in the circuit was set in the humidity generating machine where the relative humidity was changed stepwise from a low level to a high level and then from the high level to the low level both at 25° C. During the humidity cycling process, the humidity sensor which was allowed to stand at a selected relative humidity for 30 minutes was measured for output voltage. The selected relative humidity levels were RH 5%, RH 10%, RH 20%, RH 30%, RH 40%, RH 50%, RH 60%, RH 70%, RH 80%, RH 90% and RH 95%. The results are plotted in FIG. 21.

Figure 22:
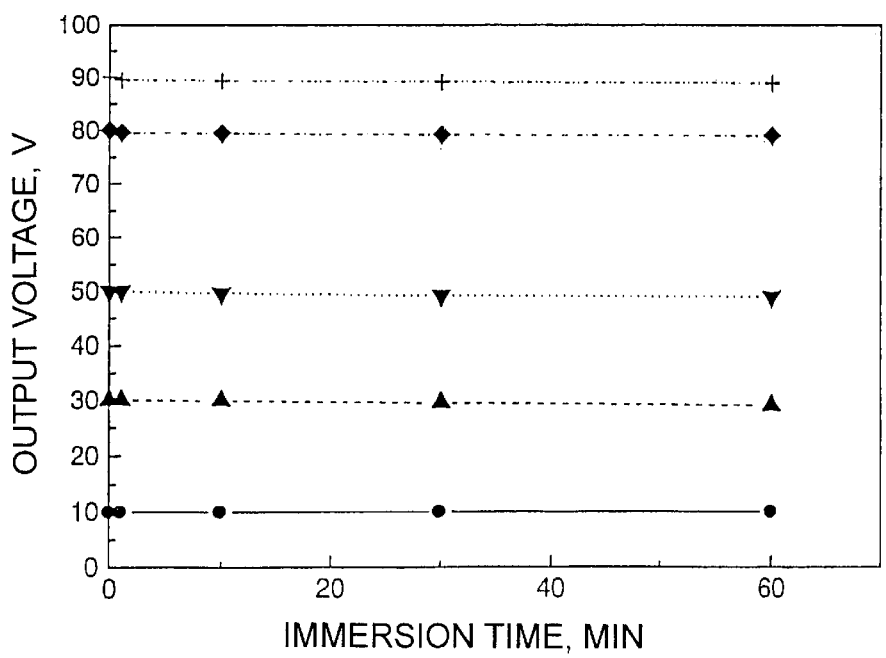
FIG. 22 is a graph showing the measured results of a water resistance test on the humidity sensor device of Example 12.

In the water resistance test, the humidity sensor having undergone output voltage monitoring as mentioned above was immersed in distilled water for 1 minute, dried in air, and measured for output voltage again. Subsequently, the time duration when the humidity sensor was immersed in distilled water was prolonged to 10 minutes, 30 minutes and 60 minutes whereupon the output voltage was similarly measured at relative humidity levels of RH 10%, RH 30%, RH 50%, RH 80% and RH 90% for comparison. The results are plotted in FIG. 22.

Figure 21:
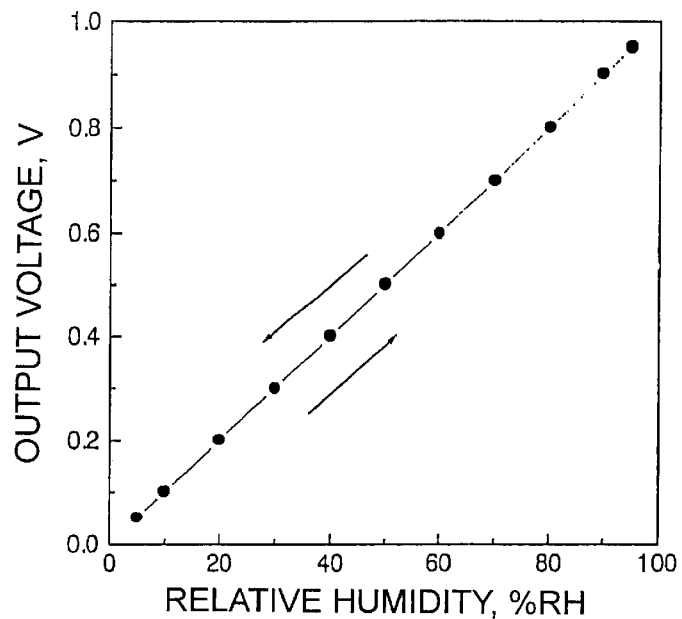
FIG. 21 is a graph showing the measured results of output of the humidity sensor device of Example 12.

It is evident from FIG. 21 that the inventive humidity sensor develops a good response curve without hysteresis. It is evident from FIG. 22 that the inventive humidity sensor is fully resistant to water.

Also a gas resistance test was carried out as in Example 10, obtaining satisfactory results as in Example 10.

Example 13

A humidity sensor device was fabricated as in Example 12 except that the interdigital electrode-bearing substrate was plasma treated under atmospheric pressure. The device was similarly evaluated for performance, obtaining likewise satisfactory results.

The plasma treatment in this Example used an atmospheric pressure plasma cleaning apparatus by Matsushita Electric Machine & Vision Co., Ltd. Treatment was carried out by applying an oxygen plasma at a power of 700 W, an irradiation distance of 5 mm, and a head moving speed of 10 mm/sec and then a hydrogen plasma under the same conditions.

Example 14

In 23 g of methanol, 6.30 g (36.6 mmol) of N,N,N',N'-tetramethyldiamino-1,12-dodecane and 9.62 g (40.2 mmol) of 1,12-dichlorododecane were reacted at 110° C. for 48 hours. Re-precipitation from acetone gave 6.04 g of a white precipitate. Subsequently, 5.07 g of the white precipitate was reacted with 2.98 g of dimethylaminopropylmethacrylamide in methanol at 90° C. for 24 hours. Reverse re-precipitation from acetone gave 2.47 g of a pale yellow precipitate. It had a number average molecular weight of 2734. This substance corresponds to a monomer of formula (2).

The monomer of formula (2) was dissolved in ethyl cellosolve to form 10 ml of a 5 wt % solution, to which 0.2% by weight of KAYACURE ABQ (Nippon Kayaku Co., Ltd.) was added as a polymerization initiator, giving a solution of the humidity sensitive thin film-forming monomer. The solution was held at 4° C. for storage.

Then a humidity sensor device 1 as shown in FIG. 1 was fabricated. A porous ceramic substrate of alumina was used as the insulating substrate 2. Interdigital electrodes 4 were formed on the substrate by screen printing paste containing $RuO_2$ and glass frit and firing at high temperature. The gap between the electrodes 4 was about 225 μm.

The interdigital electrode-bearing substrate was submerged in 100 ml of isopropyl alcohol, immersed therein for cleaning for 10 minutes, and allowed to stand for drying.

A plasma treatment was carried out using a plasma dry cleaner model PDC200 by Yamato Science Co., Ltd. After 100 samples to be treated were placed, the chamber was evacuated to vacuum by operating a vacuum pump EC-403 by ULVAC Co. for 10 minutes. Oxygen gas was fed to the chamber at a flow rate of 300 sccm (0.51 $Pa \cdot m^3 \cdot s^{-1}$) while a vacuum of 55 Pa was maintained. A plasma was generated at an RF power of 700 W, with which the samples were treated for one minute. The distance between electrodes was 10 cm.

Immediately after the treatment, the humidity sensitive thin film-forming monomer solution was applied to the substrate by dispensing an aliquot of 2.75 μl per device. By holding at 25° C. for 15 minutes for drying, a coating was formed. Then the coating was exposed to UV radiation in a nitrogen atmosphere for one minute for polymerization, yielding a humidity sensitive thin film. At this point, the exposure of UV radiation was 1,000 $mJ/cm^2$. The humidity sensitive thin film had a thickness of 5 μm.

The humidity sensor device thus fabricated was evaluated for output and examined by a water resistance test.

For evaluating the output, a divided flow humidity generating machine model SRH-1 (manufactured by Shinei K.K.) was used. The humidity sensor was incorporated in the circuit described and shown in JP-A 3-123843. The humidity sensor incorporated in the circuit was set in the humidity generating machine where the relative humidity was changed stepwise from a low level to a high level and then from the high level to the low level both at 25° C. During the humidity cycling process, the humidity sensor which was allowed to stand at a selected relative humidity for 30 minutes was measured for output voltage. The selected relative humidity levels were RH 5%, RH 10%, RH 20%, RH 30%, RH 40%, RH 50%, RH 60%, RH 70%, RH 80%, RH 90% and RH 95%. The results are plotted in FIG. 23.

Figure 24:
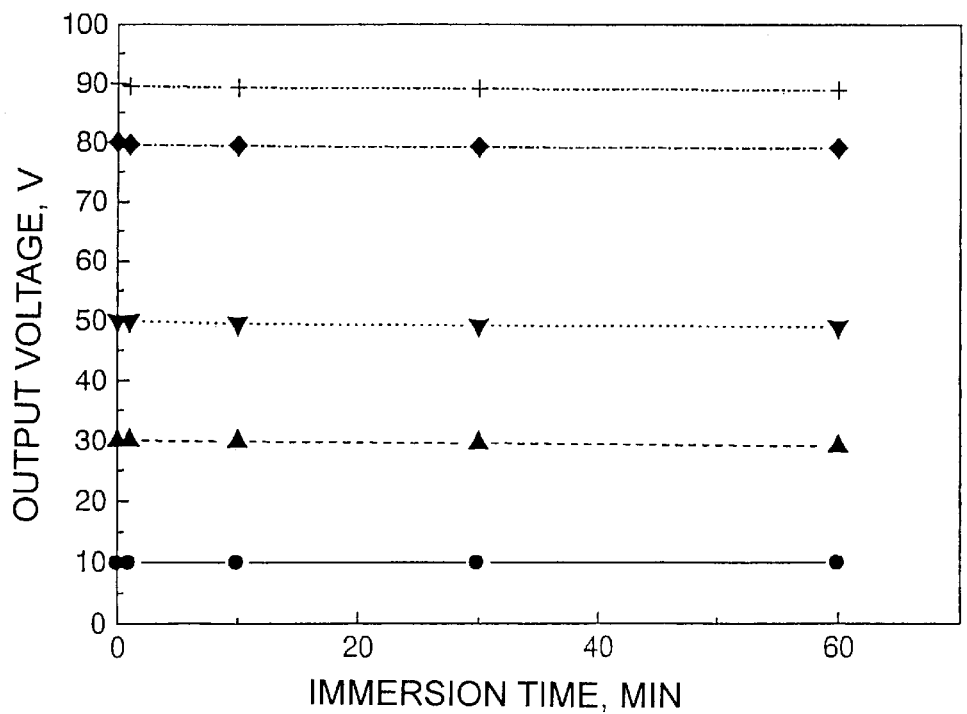
FIG. 24 is a graph showing the measured results of a water resistance test on the humidity sensor device of Example 14.

In the water resistance test, the humidity sensor having undergone output voltage monitoring as mentioned above was immersed in distilled water for 1 minute, dried in air, and measured for output voltage again. Subsequently, the time duration when the humidity sensor was immersed in distilled water was prolonged to 10 minutes, 30 minutes and 60 minutes whereupon the output voltage was similarly measured at relative humidity levels of RH 10%, RH 30%, RH 50%, RH 80% and RH 90% for comparison. The results are plotted in FIG. 24.

Figure 23:
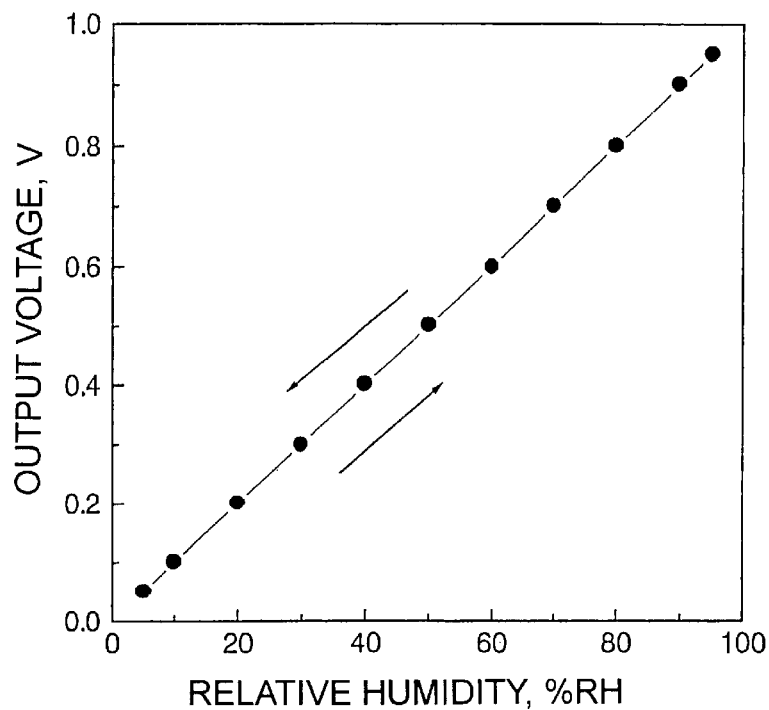
FIG. 23 is a graph showing the measured results of output of the humidity sensor device of Example 14.

It is evident from FIG. 23 that the inventive humidity sensor develops a good response curve without hysteresis. It is evident from FIG. 24 that the inventive humidity sensor is fully resistant to water.

Additionally, a gas resistance test was carried out. Gas resistance was tested by measuring outputs of the humidity sensor at different relative humidity levels, confirming a linear response thereof, then holding the sensor under conditions: temperature 40° C. and humidity RH 70 to 80% for 100 hours while flowing nitrogen dioxide gas, hydrogen chloride gas, ammonia gas, sulfur dioxide gas, chlorine gas and hydrogen sulfide gas each in a concentration of 5 ppm, measuring again a humidity-representing output (HRH) of the humidity sensor at a preset relative humidity level (HRH), and determining a maximum change (HRH). In all the tests, the percent change, though somewhat varied depending on the type of gas, fell within the range between −5% and +5%, indicating satisfactory gas resistance.

Example 15

In 20 ml of acetonitrile, 9.63 g (67.2 mmol) of methylaminoethyl acrylate was reacted with 3.79 g (33.6 mmol) of 1,3-dichloropropane at 60° C. for 128 hours. Re-precipitation from acetone gave 5.131 g of a white precipitate. This substance corresponds to a monomer of formula (1) wherein one of $R_{11}$ and $R_{12}$ is hydrogen and one of $R_{13}$ and $R_{14}$ is hydrogen.

There was prepared 10 ml of a humidity sensitive thin film-forming monomer solution having the same compositional ratio as in Example 14.

A plasma treatment was carried out using an atmospheric pressure plasma cleaning apparatus by Matsushita Electric Machine & Vision Co., Ltd. Treatment was carried out by applying an oxygen plasma at a power of 700 W, an irradiation distance of 5 mm, and a head moving speed of 10 mm/sec and then a hydrogen plasma under the same conditions.

Thereafter, as in Example 14, a humidity sensitive thin film was formed and a humidity sensor device fabricated.

The humidity sensor device thus fabricated was subjected to output evaluation and a water resistance test as in Example 1. The measured results of output are shown in FIG. 25, and the measured results of the water resistance test are shown in FIG. 26.

Figure 25:
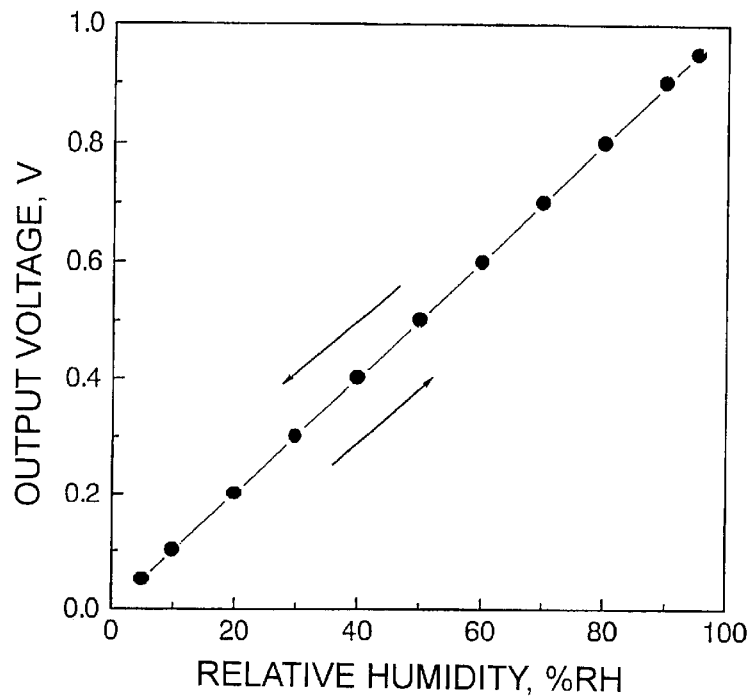
FIG. 25 is a graph showing the measured results of output of the humidity sensor device of Example 15.
Figure 26:
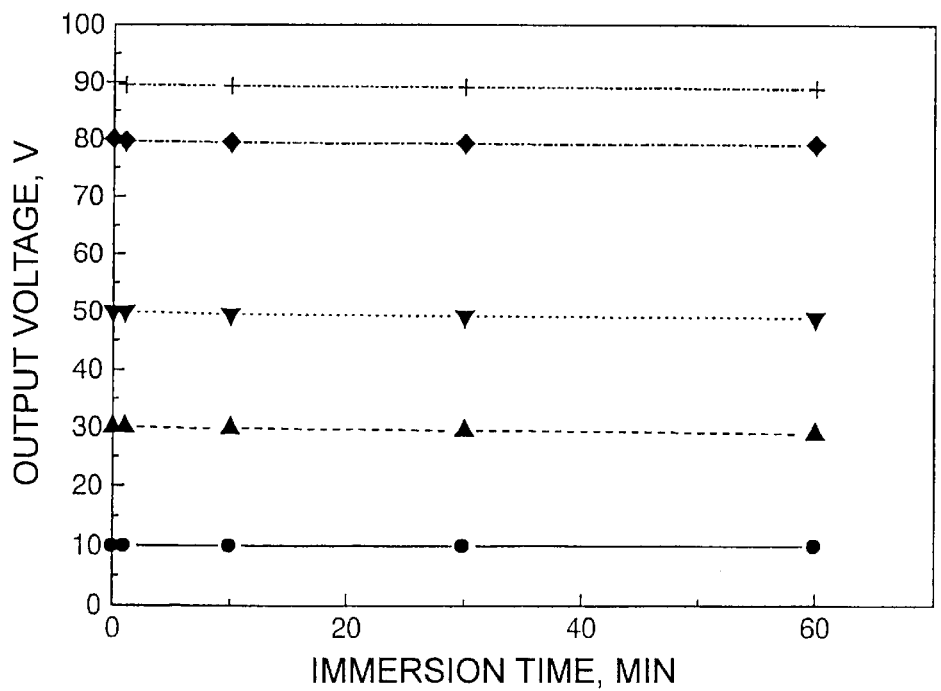
FIG. 26 is a graph showing the measured results of a water resistance test on the humidity sensor device of Example 15.

It is evident from FIGS. 25 and 26 that the inventive humidity sensor develops satisfactory humidity response performance and water resistance.

Also a gas resistance test was carried out as in Example 14. The percent change fell within the range between −5% and +5%, with no problems found with respect to the gas resistance.

Example 16

In methanol, 8.52 g of dimethylaminopropyl methacrylamide was reacted with 7.58 g of n-propyl chloride at 70° C. for 24 hours. Re-precipitation from acetone gave 13.28 g of a white precipitate. This substance corresponds to a monomer of formula (5).

A humidity sensitive thin film-forming monomer solution was prepared from this substance by the same procedure as in Example 14. After plasma treatment was carried out under the same conditions as in Example 14, a humidity sensitive thin film was formed, and a humidity sensor device fabricated.

The humidity sensor device thus fabricated was subjected to output evaluation and a water resistance test as in Example 14. The measured results of output are shown in FIG. 27, and the measured results of the water resistance test are shown in FIG. 28.

Figure 27:
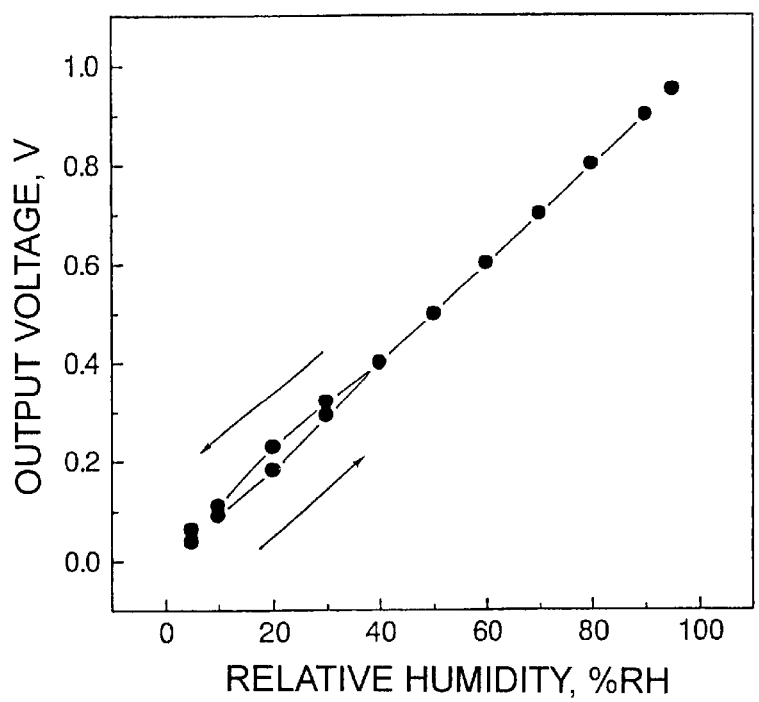
FIG. 27 is a graph showing the measured results of output of the humidity sensor device of Example 16.
Figure 28:
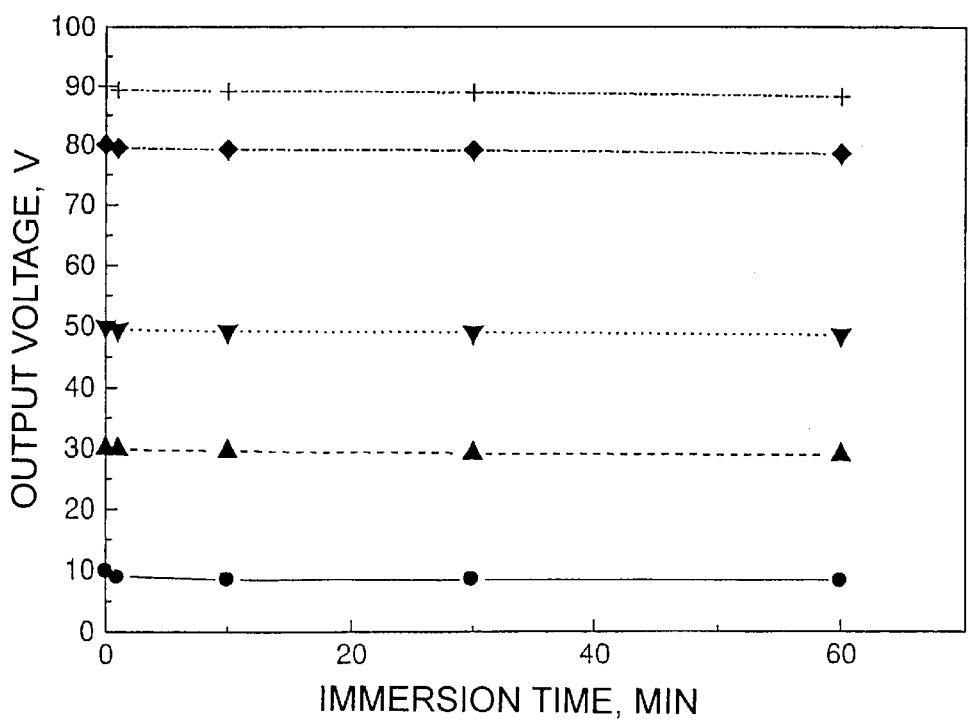
FIG. 28 is a graph showing the measured results of a water resistance test on the humidity sensor device of Example 16.

A little hysteresis is observed in FIG. 27, but water resistance is satisfactory as seen from FIG. 28.

Also a gas resistance test was carried out as in Example 14. The percent change fell within the range between −5% and +5%, with no problems found with respect to the gas resistance.

Example 17

A humidity sensor device was fabricated as in Example 14 except that the time of plasma treatment was 10 minutes, and the interdigital electrode-bearing substrate after the plasma treatment was vacuum held in a desiccator for 24 hours.

The humidity sensor device thus fabricated was subjected to output evaluation and a water resistance test as in Example 14. The measured results of output are shown in FIG. 29, and the measured results of the water resistance test are shown in FIG. 30.

Figure 29:
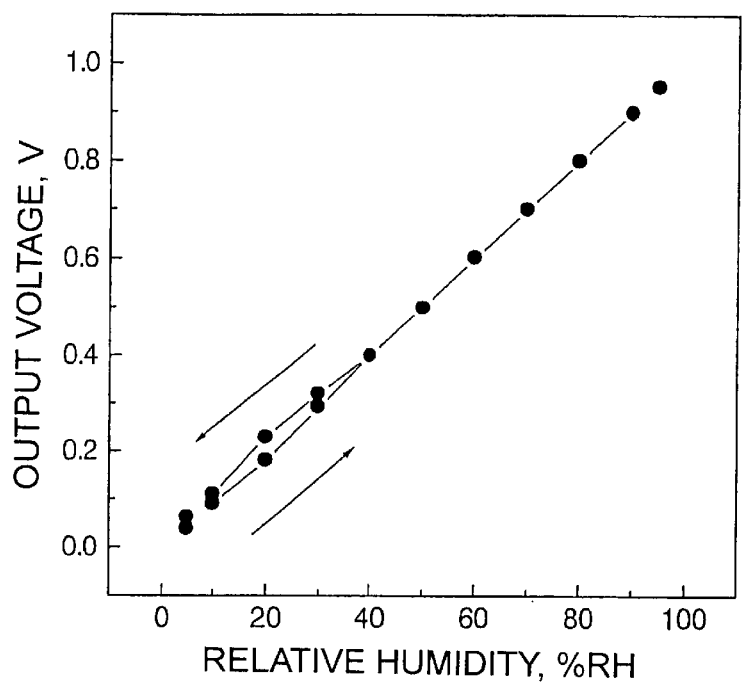
FIG. 29 is a graph showing the measured results of output of the humidity sensor device of Example 17.
Figure 30:
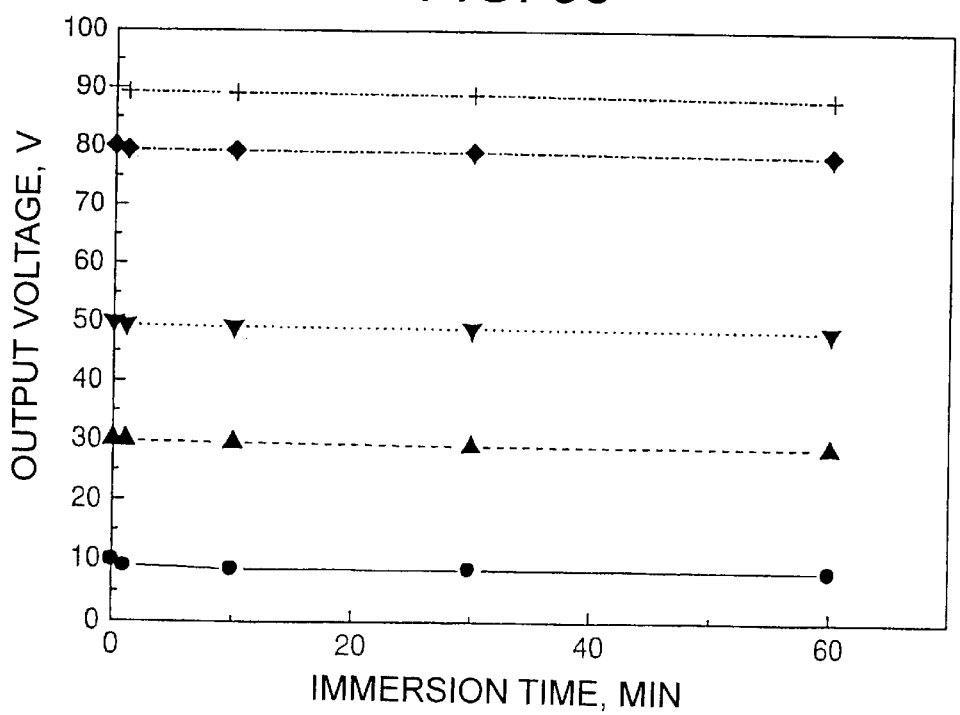
FIG. 30 is a graph showing the measured results of a water resistance test on the humidity sensor device of Example 17.

A little hysteresis is observed in FIG. 29, but water resistance is satisfactory as seen from FIG. 30.

Also a gas resistance test was carried out as in Example 14. The percent change fell within the range between −5% and +5%, with no problems found with respect to the gas resistance.

Example 18

A humidity sensor device was fabricated as in Example 14 except that some plasma treatment conditions were changed to an Ar gas flow rate of 15 sccm (0.0255 Pa·m$^3$·s$^{-1}$) and a time of 2 minutes.

The humidity sensor device thus fabricated was subjected to output evaluation and a water resistance test as in Example 14. The measured results of output are shown in FIG. 31, and the measured results of the water resistance test are shown in FIG. 32.

Figure 31:
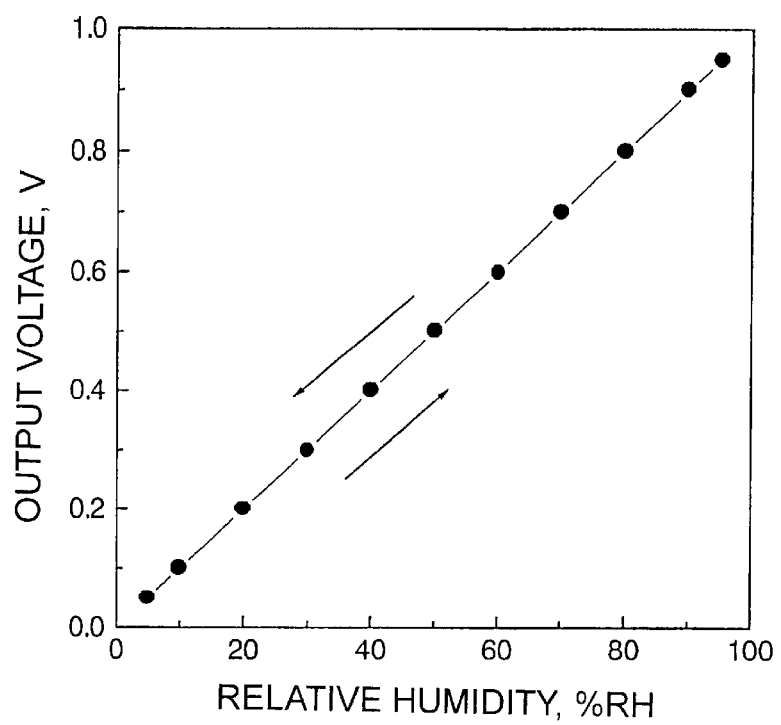
FIG. 31 is a graph showing the measured results of output of the humidity sensor device of Example 18.
Figure 32:
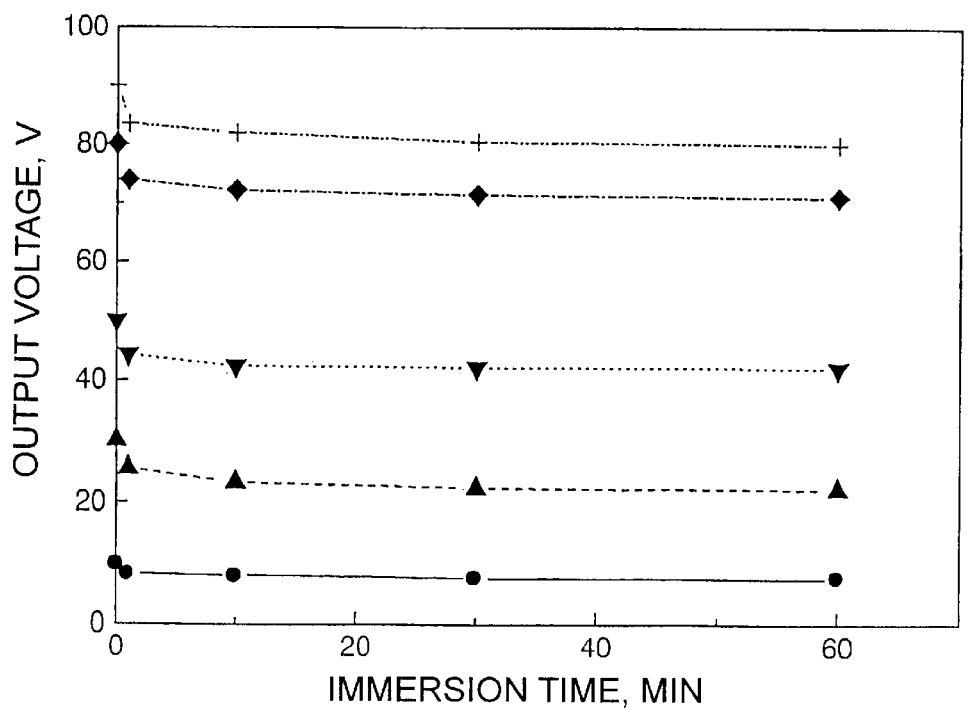
FIG. 32 is a graph showing the measured results of a water resistance test on the humidity sensor device of Example 18.

It is seen from FIG. 31 that the output performance was substantially the same as in Example 14. In the water resistance test, however, the water resistance somewhat declined as seen from FIG. 32.

Also a gas resistance test was carried out as in Example 14. The percent change fell within the range between −5% and +5%, with no problems found with respect to the gas resistance.

Example 19

A humidity sensor device was fabricated as in Example 14 except that UV/ozone treatment was carried out instead of the plasma treatment.

The UV/ozone treatment was carried out for 10 minutes under conditions of 4.5 W×2 using a UV ozone cleaner NL-UV252 by Nippon Laser Electron Co., Ltd.

Figure 33:
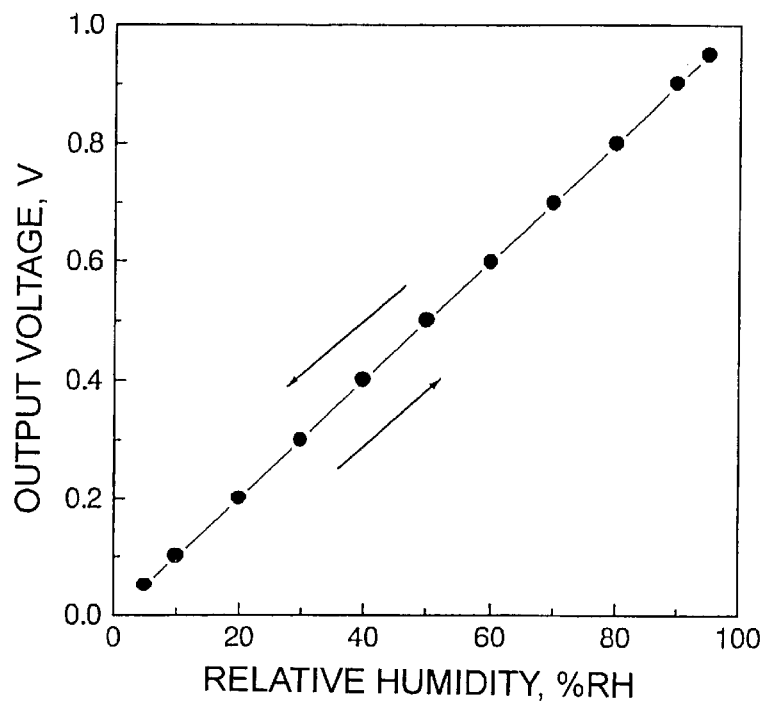
FIG. 33 is a graph showing the measured results of output of the humidity sensor device of Example 19.
Figure 34:
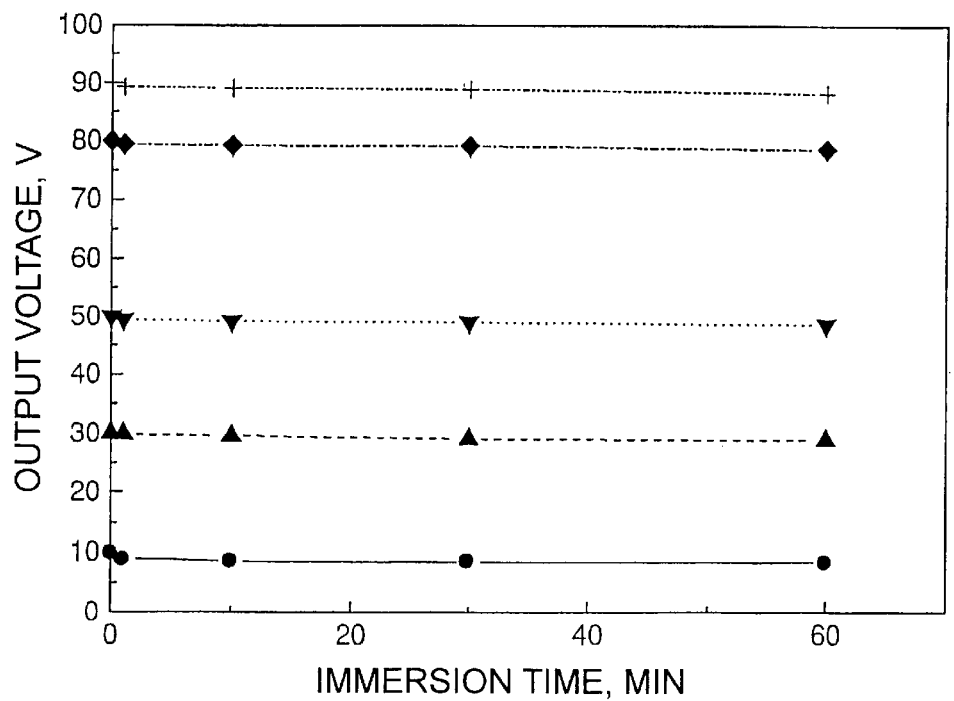
FIG. 34 is a graph showing the measured results of a water resistance test on the humidity sensor device of Example 19.

The humidity sensor device thus fabricated was subjected to output evaluation and a water resistance test as in Example 14. The measured results of output are shown in FIG. 33, and the measured results of the water resistance test are shown in FIG. 34.

Both the output performance and water resistance were substantially equivalent to those of Example 14, but the alumina substrate was colored pale yellow.

Also a gas resistance test was carried out as in Example 14. The percent change fell within the range between −5% and +5%, with no problems found with respect to the gas resistance.

Comparative Example 5

Prior to the fabrication of a humidity sensor device, the interdigital electrode-bearing substrate was submerged in 100 ml of isopropyl alcohol, immersed therein for cleaning for 10 minutes while applying ultrasonic waves, and allowed to stand for drying. This operation was repeated three cycles.

The interdigital electrode-bearing substrate, without plasma treatment, was coated with the humidity sensitive thin film-forming monomer solution as in Example 14, and a humidity sensor device fabricated as in Example 14.

The humidity sensor device thus fabricated was subjected to output evaluation and a water resistance test as in Example 14. The measured results of output are shown in FIG. 35, and the measured results of the water resistance test are shown in FIG. 36.

Figure 35:
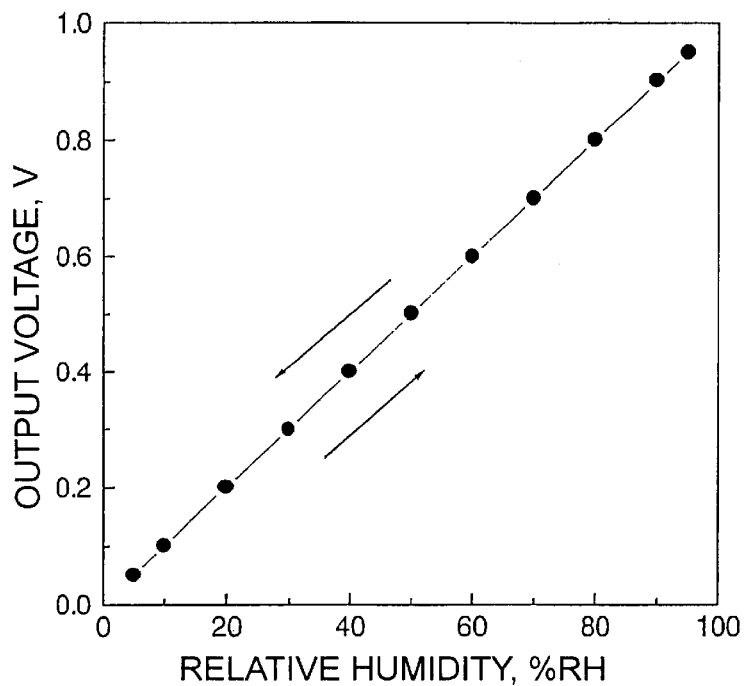
FIG. 35 is a graph showing the measured results of output of the humidity sensor device of Comparative Example 5.
Figure 36:
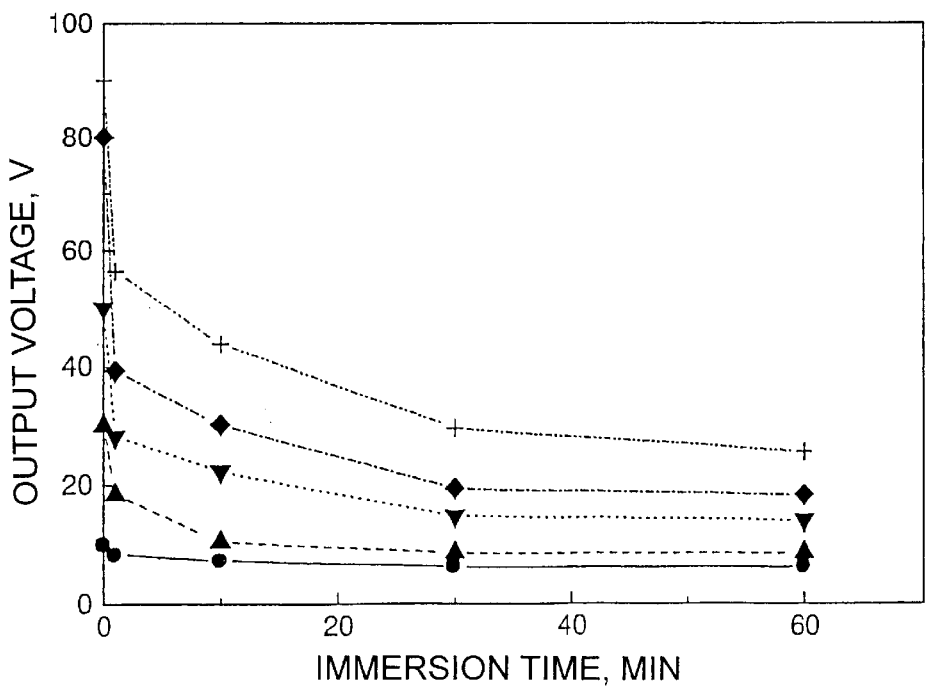
FIG. 36 is a graph showing the measured results of a water resistance test on the humidity sensor device of Comparative Example 5.

It is seen from FIG. 35 that the output performance was substantially equivalent to that of Example 14. In the water resistance test, however, water resistance was lost as shown in FIG. 36. No problems were found with respect to the gas resistance.

Benefits of the Invention

There has been described a humidity sensor device which has improved water resistance, minimized gas influence, and improved solvent resistance, and exhibits stable output performance in a wide humidity region. When an insulating substrate which has been treated by physical means such as plasma treatment is used, the manufacturing process is simplified.

What is claimed is:

1. A humidity sensor device comprising an insulating substrate, a pair of opposed electrodes disposed on the substrate to define a gap therebetween, and a humidity sensitive thin film lying on the gap, said humidity sensitive thin film comprising a copolymer of at least one monomer of the following formula (1) with at least one monomer of the following formula (2):

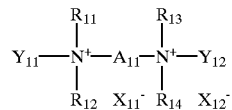

(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an ethylenically unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion,

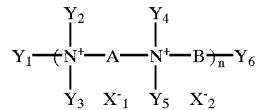

(2)

wherein each of A and B is a divalent group, each of $Y_1$, $Y_2$, $Y_3$, $Y_4$, $Y_5$ and $Y_6$ which may be the same or different is a monovalent group, at least one of Y's is a group terminated with an ethylenically unsaturated reactive group, any two or more of $Y_1$, $Y_2$, $Y_3$, $Y_4$, $Y_5$, A and portions thereof adjoining the nitrogen (N) atom or any two or more of $Y_4$, $Y_5$, $Y_6$, B and portions thereof adjoining the nitrogen (N) atom may bond together to form a ring with the nitrogen (N) atom, each of $X_1^-$ and $X_2^-$ which may be the same or different is an anion, and n is a number of 2 to 5,000.

2. The humidity sensor device of claim 1 wherein the anions represented by $X_1^-$ and $X_2^-$ in formula (2) and the anions represented by $X_{11}^-$ and $X_{12}^-$ in formula (1) are halide ions.

3. The humidity sensor device of claim 2 wherein chloride ions or bromide ions are contained as the halide ions.

4. The humidity sensor device of claim 1 wherein the divalent groups represented by A and B in formula (2) and the divalent group represented by $A_{11}$ in formula (1) each are an alkylene, alkenylene or arylene group or a mixture thereof.

5. The humidity sensor device of claim 1 wherein the monovalent groups represented by $Y_{11}$ and $Y_{12}$ in formula (1) each are an alkylene acrylate or methacrylate group or alkylene acrylate or methacrylate amide group.

6. The humidity sensor device of claim 1 wherein the monomer of formula (1) is a difunctional monomer obtained by reacting a dialkylaminoethyl acrylate or methacrylate or a dialkylaminoethyl acrylate or methacrylate amide with a dihalogen compound.

7. The humidity sensor device of claim 1 wherein the monomer of formula (1) is obtained by reacting an acrylic unsaturated compound having a dialkylamino group with a dihalogen compound of the divalent group represented by $A_{11}$ in formula (1).

8. The humidity sensor device of claim 1 wherein the copolymer further includes an acrylic monomer having an alkoxysilyl group.

9. The humidity sensor device of claim 1 wherein the insulating substrate is an insulating substrate from which contaminants and/or oxides on its uppermost surface layer have been removed by physical means.

10. A method for preparing a humidity sensor device comprising an insulating substrate, a pair of opposed electrodes disposed on the substrate to define a gap therebetween, and a humidity sensitive thin film lying on the gap, said method comprising the steps of coating a coating solution containing a monomer of the following formula (1) and a monomer of the following formula (2) onto the insulating substrate and causing the monomers to copolymerize to form the humidity sensitive thin film,

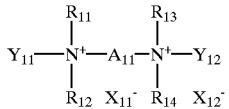
(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an ethylenically unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion,

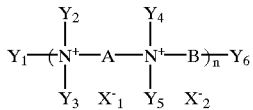
(2)

wherein each of A and B is a divalent group, each of $Y_1$, $Y_2$, $Y_3$, $Y_4$, $Y_5$ and $Y_6$ which may be the same or different is a monovalent group, at least one of Y's is a group terminated with an ethylenically unsaturated reactive group, any two or more of $Y_1$, $Y_2$, $Y_3$, $Y_4$, $Y_5$, A and portions thereof adjoining the nitrogen (N) atom or any two or more of $Y_4$, $Y_5$, $Y_6$, B and portions thereof adjoining the nitrogen (N) atom may bond together to form a ring with the nitrogen (N) atom, each of $X_1^-$ and $X_2^-$ which may be the same or different is an anion, and n is a number of 2 to 5,000.

11. The method for preparing a humidity sensor device of claim 10 wherein the humidity sensitive thin film is formed by previously treating the insulating substrate with an acrylic monomer having an alkoxysilyl group for joining acrylic functional groups to the insulating substrate, then coating said coating solution, or by previously incorporating an acrylic monomer having an alkoxysilyl group into said coating solution.

12. The method for preparing a humidity sensor device of claim 10, further comprising the step of removing contaminants and/or oxides on the uppermost surface layer of the insulating substrate by physical means, prior to the step of coating said coating solution.

13. The method for preparing a humidity sensor device of claim 12 wherein said physical means is plasma surface treatment.

14. The method for preparing a humidity sensor device of claim 10 wherein the copolymerization is carried out by irradiation of ultraviolet radiation.

15. A humidity sensor device comprising an insulating substrate, a pair of opposed electrodes disposed on the substrate to define a gap therebetween, and a humidity sensitive thin film lying on the gap, said humidity sensitive thin film comprising a copolymer of a monomer of the following formula (1) with an acrylic monomer having an alkoxysilyl group,

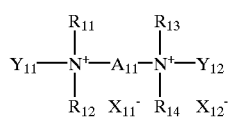
(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion.

16. The humidity sensor device of claim 15 wherein the humidity sensitive thin film is secured to the substrate through reaction of alkoxysilyl groups in the copolymer in the humidity sensitive thin film with functional groups on the surface of the insulating substrate and/or the electrodes.

17. The humidity sensor device of claim 15 wherein at least 30 mol % of the anions represented by $X_{11}^-$ and $X_{12}^-$ in the copolymer are chloride ions.

18. The humidity sensor device of claim 15 wherein the divalent group represented by $A_{11}$ in formula (1) is an alkylene, alkenylene or arylene group or a mixture thereof.

19. The humidity sensor device of claim 15 wherein the monovalent groups represented by $Y_{11}$ and $Y_{12}$ in formula (1) each are an alkylene acrylate or methacrylate group or alkylene acrylate or methacrylate amide group.

20. The humidity sensor device of claim 15 wherein the monomer of formula (1) is a difunctional monomer obtained by reacting a dialkylaminoethyl acrylate or methacrylate or a dialkylaminoethyl acrylate or methacrylate amide with a dihalogen compound.

21. The humidity sensor device of claim 15 wherein the monomer of formula (1) is obtained by reacting an acrylic unsaturated compound having a dialkylamino group with a dihalogen compound of the divalent group represented by $A_{11}$ in formula (1).

22. A method for preparing a humidity sensor device comprising an insulating substrate, a pair of opposed electrodes disposed on the substrate to define a gap therebetween, and a humidity sensitive thin film lying on the gap, said method comprising the steps of previously treating the insulating substrate with an acrylic monomer having an alkoxysilyl group for joining acrylic functional groups to the insulating substrate, coating a monomer of the following formula (1), then causing the monomer to polymerize to form the humidity sensitive thin film,

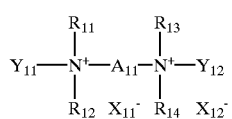
(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion.

23. The method for preparing a humidity sensor device of claim 22 wherein the polymerization is carried out by irradiation of ultraviolet radiation.

24. A method for preparing a humidity sensor device comprising an insulating substrate, a pair of opposed electrodes disposed on the substrate to define a gap therebetween, and a humidity sensitive thin film lying on the gap, said method comprising the steps of coating a monomer of the following formula (1) and an acrylic monomer having an alkoxysilyl group onto the insulating substrate, causing the monomers to copolymerize into a copolymer, and causing the alkoxysilyl groups to react with functional groups on the surface of the insulating substrate in the presence of water vapor to secure the copolymer to the insulating substrate, for thereby forming the humidity sensitive thin film,

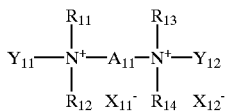
(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion.

25. The method for preparing a humidity sensor device of claim 24 wherein the polymerization is carried out by irradiation of ultraviolet radiation.

26. A humidity sensor device comprising an insulating substrate, a pair of opposed electrodes disposed on the substrate to define a gap therebetween, and a humidity sensitive thin film lying on the gap, wherein said insulating substrate is an insulating substrate from which contaminants and/or oxides on its uppermost surface layer have been removed by physical means, and said humidity sensitive thin film comprises a polymer resulting from a monomer of the following formula (1):

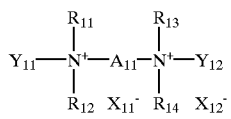
(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, each of $X_{11}^-$ and $X_{12}^-$ which may be the same or different is an anion.

27. The humidity sensor device of claim 26 wherein at least 30 mol % of the anions represented by $X_{11}^-$ and $X_{12}^-$ in the copolymer are chloride ions.

28. The humidity sensor device of claim 26 wherein the divalent group represented by $A_{11}$ in formula (1) is an alkylene, alkenylene or arylene group or a mixture thereof.

29. The humidity sensor device of claim 26 wherein the monovalent groups represented by $Y_{11}$ and $Y_{12}$ in formula (1) each are an alkylene acrylate or methacrylate group or alkylene acrylate or methacrylate amide group.

30. The humidity sensor device of claim 26 wherein the monomer of formula (1) is a difunctional monomer obtained by reacting a dialkylaminoethyl acrylate or methacrylate or a dialkylaminoethyl acrylate or methacrylate amide with a dihalogen compound.

31. The humidity sensor device of claim 26 wherein the monomer of formula (1) is obtained by reacting an acrylic unsaturated compound having a dialkylamino group with a dihalogen compound of the divalent group represented by $A_{11}$ in formula (1).

32. A method for preparing a humidity sensor device comprising an insulating substrate, a pair of opposed electrodes disposed on the substrate to define a gap therebetween, and a humidity sensitive thin film lying on the gap, said method comprising the steps of removing contaminants and/or oxides on the uppermost surface layer of the insulating substrate by physical means, then coating a monomer of the following formula (1) onto the insulating substrate, and causing the monomer to copolymerize on the insulating substrate for thereby forming the humidity sensitive thin film:

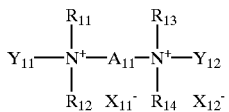
(1)

wherein $A_{11}$ is a divalent group, each of $R_{11}$, $R_{12}$, $R_{13}$ and $R_{14}$ which may be the same or different is an alkyl group, each of $Y_{11}$ and $Y_{12}$ which may be the same or different is a monovalent group terminated with an unsaturated reactive group, any two or more of $R_{11}$ to $R_{14}$, $Y_{11}$, $Y_{12}$, $A_{11}$ and portions thereof adjoining the nitrogen (N) atom may bond together to form a ring with the nitrogen (N) atom, and each of $X_{11}^-$ and $X_{12}^-$ which may be the same or different is an anion.

33. The method for preparing a humidity sensor device of claim 32 wherein said physical means is plasma surface treatment.

34. The method for preparing a humidity sensor device of claim 32 wherein the polymerization is carried out by irradiation of ultraviolet radiation.

35. A method for preparing a humidity sensor device comprising an insulating substrate, a pair of opposed electrodes disposed on the substrate to define a gap therebetween, and a humidity sensitive thin film lying on the gap, said method comprising the steps of removing oxides and optionally contaminants on the uppermost surface layer of the insulating substrate by physical means, then coating a monomer having an ethylenically unsaturated reactive group onto the insulating substrate, and causing the monomer to copolymerize on the insulating substrate for thereby forming the humidity sensitive thin film.

36. The method for preparing a humidity sensor device of claim 35 wherein said physical means is plasma surface treatment.

37. The method for preparing a humidity sensor device of claim 35 wherein the monomer having an ethylenically unsaturated reactive group contains a quaternary ammonium salt.

38. A humidity sensor device comprising an insulating substrate, a pair of opposed electrodes disposed on the substrate to define a gap therebetween, and a humidity sensitive thin film lying on the gap, wherein said the insulating substrate is an insulating substrate from which oxides and optionally contaminants on its uppermost surface layer have been removed by physical means, and said humidity sensitive thin film comprises a polymer resulting from a monomer having an ethylenically unsaturated reactive group.

* * * * *